(12) United States Patent
Chang et al.

(10) Patent No.: US 10,502,707 B1
(45) Date of Patent: Dec. 10, 2019

(54) DIFFERENTIAL SENSING WITH BIOFET SENSORS

(71) Applicant: Taiwan Semiconductor Manufacturing Co., Ltd., Hsinchu (TW)

(72) Inventors: Allen Timothy Chang, Hsinchu (TW); Jui-Cheng Huang, Hsinchu (TW); Tung-Tsun Chen, Hsinchu (TW); Yu-Jie Huang, Kaohsiung (TW); Penny Hsiao, Hsinchu (TW)

(73) Assignee: Taiwan Semiconductor Manufacturing Co., Ltd. (TW)

( * ) Notice: Subject to any disclaimer, the term of this patent is extended or adjusted under 35 U.S.C. 154(b) by 0 days.

(21) Appl. No.: 15/994,802

(22) Filed: May 31, 2018

(51) Int. Cl.
*G01N 27/414* (2006.01)
*H01L 21/8234* (2006.01)
*H01L 21/768* (2006.01)
*H01L 21/8238* (2006.01)
*H01L 21/762* (2006.01)

(52) U.S. Cl.
CPC ..... *G01N 27/4145* (2013.01); *G01N 27/4141* (2013.01); *G01N 27/4146* (2013.01); *G01N 27/4148* (2013.01); *H01L 21/762* (2013.01); *H01L 21/76802* (2013.01); *H01L 21/823412* (2013.01); *H01L 21/823418* (2013.01); *H01L 21/823807* (2013.01); *H01L 21/823814* (2013.01)

(58) Field of Classification Search
CPC ............... H01L 21/752; H01L 21/6802; H01L 21/76802; G01N 27/4145; G01N 27/4141; G01N 27/4146; G01N 27/4148
See application file for complete search history.

(56) References Cited

U.S. PATENT DOCUMENTS

| | | | | |
|---|---|---|---|---|
| 5,726,026 A | * | 3/1998 | Wilding | B01D 67/0062 366/DIG. 3 |
| 8,728,844 B1 | * | 5/2014 | Liu | H01L 29/66477 438/49 |
| 9,976,982 B2 | | 5/2018 | Cheng et al. | |
| 2004/0170530 A1 | * | 9/2004 | Hefti | B01L 3/5025 422/82.02 |

(Continued)

FOREIGN PATENT DOCUMENTS

| | | |
|---|---|---|
| TW | 201124722 A | 7/2011 |
| TW | 201436237 A | 9/2014 |

*Primary Examiner* — Matthew L Reames
(74) *Attorney, Agent, or Firm* — Sterne, Kessler, Goldstein & Fox P.L.L.C.

(57) ABSTRACT

A microfluidic system includes a semiconductor substrate having a first surface and an opposite, parallel second surface, a first bioFET sensor and a second bioFET sensor. An isolation layer is disposed on the second surface of the semiconductor substrate and has a first opening over the first bioFET sensor and a second opening over the second bioFET sensor. An interface layer is disposed in at least each of the first opening and the second opening. The system includes a readout circuit having a differential amplifier designed to measure a difference between signals associated with the first bioFET sensor and the second bioFET sensor. The system also includes a microfluidic network designed to deliver fluid to the interface layer disposed in each of the first opening and the second opening.

20 Claims, 21 Drawing Sheets

(56) References Cited

U.S. PATENT DOCUMENTS

2005/0156207 A1* 7/2005 Yazawa ................ G01N 27/414
                                                    257/288
2007/0138028 A1    6/2007 Chodavarapu et al.
2011/0031118 A1* 2/2011 Machida ............ G01N 27/3272
                                                    204/403.14

* cited by examiner

DIFFERENTIAL SENSING WITH BIOFET SENSORS

BACKGROUND

Biosensors are devices for sensing and detecting biomolecules and operate on the basis of electronic, electrochemical, optical, and/or mechanical detection principles. Biosensors that include transistors are sensors that electrically sense charges, photons, and/or mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes and can be easily applied to integrated circuits (ICs) and microelectromechanical systems (MEMS).

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
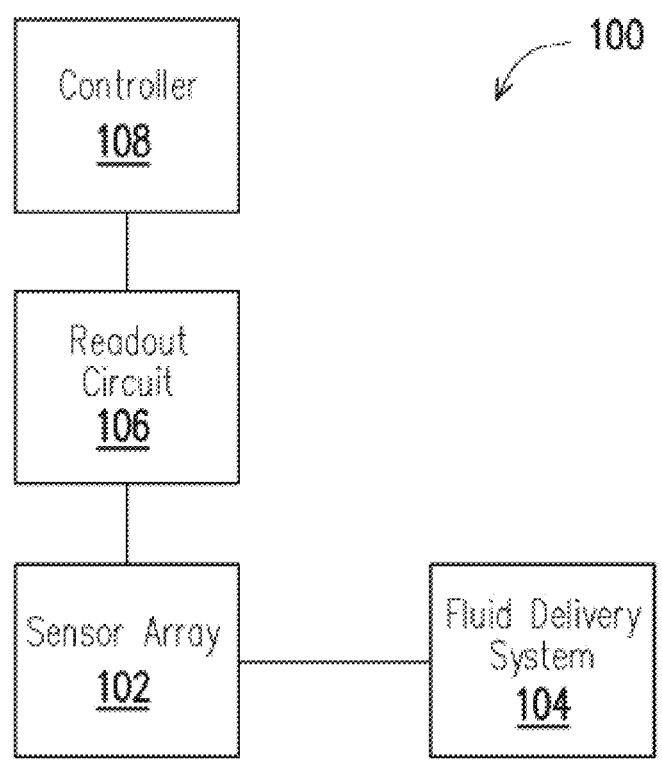
FIG. 1 illustrates components of a sensing device, according to some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over a second feature in the description that follows may include embodiments in which the first and second features are formed in direct contact, and may also include embodiments in which additional features may be formed and/or disposed between the first and second features, such that the first and second features may not be in direct contact. In addition, the present disclosure may repeat reference numerals and/or letters in the various examples. This does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (e.g., rotated 90 degrees or at other orientations) and the spatially relative descriptors used herein may likewise be interpreted accordingly.

Terminology

Unless defined otherwise, all technical and scientific terms used herein have the same meanings as commonly understood by one of ordinary skill in the art to which this disclosure belongs. Although any methods and materials similar or equivalent to those described herein can be used in the practice or testing of embodiments in accordance with the disclosure; the methods, devices, and materials are now described. All patents and publications mentioned herein are incorporated herein by reference for the purpose of describing and disclosing the materials and methodologies that are reported in the publications may be used in connection with the present disclosure.

The acronym "FET," as used herein, refers to a field effect transistor. A type of FET is referred to as a "metal oxide semiconductor field effect transistor" (MOSFET). MOSFETs can be planar structures built in and on the planar surface of a substrate such as a semiconductor wafer. MOSFETs can also have a three-dimensional, fin-based structures.

The term "bioFET" refers to a FET that includes a layer of immobilized probe molecules that act as surface receptors to detect the presence of a target analyte of biological origin. A bioFET is a field-effect sensor with a semiconductor transducer, according to some embodiments. One advantage of bioFETs is the prospect of label-free operation, Specifically, bioFETs enable the avoidance of costly and time-consuming labeling operations such as the labeling of an analyte with, for instance, fluorescent or radioactive probes. One specific type of bioFET described herein is a "dual-gate back-side sensing bioFET." The analytes for detection by a bioFET can be of biological origin such as, for example and without limitation, proteins, carbohydrates, lipids, tissue fragments, or portions thereof. A bioFET can be part of a broader genus of FET sensors that may also detect a chemical compound; this type of bioFET is known as a "ChemFET" or any other element. A bioFET can also detect ions such as protons or metallic ions; this type of bioFET is known as an "ISFET." The present disclosure applies to all types of FET-based sensors ("FET Sensors"). One specific type of FET Sensor described herein is a "Dual-Gate Back Side Sensing FET Sensor" (DG BSS FET Sensor).

"S/D" refers to the source/drain junctions that form two of the four terminals of a FET.

The expression "high-k" refers to a high dielectric constant. In the field of semiconductor device structures and manufacturing processes, high-k refers to a dielectric constant that is greater than the dielectric constant of $SiO_2$ (i.e., greater than 3.9).

The term "vertical," as used herein, means nominally perpendicular to the surface of a substrate.

The term "analysis" generally refers to a process or step involving physical, chemical, biochemical, or biological analysis that includes, but is not limited to, characterization, testing, measurement, optimization, separation, synthesis, addition, filtration, dissolution, or mixing.

The term "assay" generally refers to a process or step involving the analysis of a chemical or a target analyte and includes, but is not limited to, cell-based assays, biochemical assays, high-throughput assays and screening, diagnostic assays, pH determination, nucleic acid hybridization assays, polymerase activity assays, nucleic acid and protein sequencing, immunoassays (e.g., antibody-antigen binding assays, ELISAs, and iqPCR), bisulfite methylation assays for detecting methylation pattern of genes, protein assays, protein binding assays (e.g., protein-protein, protein-nucleic acid, and protein-ligand binding assays), enzymatic assays, coupled enzymatic assays, kinetic measurements (e.g., kinetics of protein folding and enzymatic reaction kinetics), enzyme inhibitor and activator screening, chemiluminescence and electrochemiluminescence assays, fluorescent assays, fluorescence polarization and anisotropy assays, absorbance and colorimetric assays (e.g., Bradford assay, Lowry assay, Hartree-Lowry assay, Biuret assay, and BCA assay), chemical assays (e.g., for the detection of environmental pollutants and contaminants, nanoparticles, or polymers), drug discovery assays, whole genome analysis, genome typing analysis, genomic-exome analysis, microbiome analysis, and clinical analysis including, but not limited to, cancer analysis, non-invasive prenatal testing (NIPT) analysis, and/or universal carrier screening (UCS) analysis. The apparatus, systems, and methods described herein may use or adopt one or more of these assays to be used with any of the FET Sensor described designs.

The term "liquid biopsy" generally refers to a biopsy sample obtained from a subject's bodily fluid as compared to a subject's tissue sample. The ability to perform assays using a body fluid sample is oftentimes more desirable than using a tissue sample. The less invasive approach using a body fluid sample has wide ranging implications in terms of patient welfare, the ability to conduct longitudinal disease monitoring, and the ability to obtain expression profiles even when tissue cells are not easily accessible, for example, in the prostate gland. Assays used to detect target analytes in liquid biopsy samples include, but are not limited to, those described above. As a non-limiting example, a circulating tumor cell (CTC) assay can be conducted on a liquid biopsy sample.

For example, a capture reagent (e.g., an antibody) immobilized on a FET Sensor may be used for detection of a target analyte (e.g., a tumor cell marker) in a liquid biopsy sample using a CTC assay. CTCs are cells that have shed into the vasculature from a tumor and circulate, for example, in the bloodstream. Generally CTCs are present in circulation in low concentrations. To assay the CTCs, CTCs are enriched from patient blood or plasma by various techniques known in the art. CTCs may be stained for specific markers using methods known in the art including, but not limited to, cytometry (e.g., flow cytometry)-based methods and IHC-based methods. For the apparatus, systems, and methods described herein, CTCs may be captured or detected using a capture reagent; or the nucleic acids, proteins, or other cellular milieu from the CTCs may be targeted as target analytes for binding to or detection by a capture reagent.

When a target analyte is detected on or from a CTC, for example, an increase in target analyte expressing or containing CTCs may help identify the subject as having a cancer that is likely to respond to a specific therapy (e.g., one associated with a target analyte) or allow for optimization of a therapeutic regimen with, for example, an antibody to the target analyte. CTC measurement and quantitation can provide information on, for example, the stage of tumor, response to therapy, disease progression, or a combination thereof. The information obtained from detecting the target analyte on the CTC can be used, for example, as a prognostic, predictive, or pharmacodynamic biomarker. In addition, CTCs assays for a liquid biopsy sample may be used either alone or in combination with additional tumor marker analysis of solid biopsy samples.

The term "identification" generally refers to the process of determining the identity of a target analyte based on its binding to a capture reagent whose identity is known.

The term "measurement" generally refers to the process of determining the amount, quantity, quality, or property of a target analyte based on its binding to a capture reagent.

The term "quantitation" generally refers to the process of determining the quantity or concentration of a target analyte based on its binding to a capture reagent.

The term "detection" generally refers to the process of determining the presence or absence of a target analyte based on its binding to a capture reagent. Detection includes but is not limited to identification, measurement, and quantitation.

The term "chemical" refers to a substance, compound, mixture, solution, emulsion, dispersion, molecule, ion, dimer, macromolecule such as a polymer or protein, biomolecule, precipitate, crystal, chemical moiety or group, particle, nanoparticle, reagent, reaction product, solvent, or fluid. Any one of these references may exist in the solid, liquid, or gaseous state, and can be the subject of an analysis.

The term "reaction" refers to a physical, chemical, biochemical, or biological transformation that involves at least one chemical and that generally involves (in the case of chemical, biochemical, and biological transformations) the breaking or formation of one or more bonds such as covalent, noncovalent, van der Waals, hydrogen, or ionic bonds. The term includes chemical reactions such as, for example, synthesis reactions, neutralization reactions, decomposition reactions, displacement reactions, reduction-oxidation reactions, precipitation, crystallization, combustion reactions, and polymerization reactions, as well as covalent and non-covalent binding, phase change, color change, phase formation, crystallization, dissolution, light emission, changes of light absorption or emissive properties, temperature change or heat absorption or emission, conformational change, and folding or unfolding of a macromolecule such as a protein.

"Capture reagent" as used herein, is a molecule or compound capable of binding the target analyte. The capture reagent can be directly or indirectly attached to a substantially solid material. The capture reagent can be a chemical, and specifically any substance for which there exists a naturally occurring target analyte (e.g., an antibody, polypeptide, DNA, RNA, cell, virus, etc.) or for which a target analyte can be prepared, and the capture reagent can bind to one or more target analytes in an assay. The capture reagent may be non-naturally occurring or naturally-occurring, and if naturally-occurring may be synthesized in vivo or in vitro.

"Target analyte" as used herein, is the substance to be detected in the test sample using embodiments of the present disclosure. The target analyte can be a chemical, and specifically any substance for which there exists a naturally occurring capture reagent (e.g., an antibody, polypeptide, DNA, RNA, cell, virus, etc.) or for which a capture reagent can be prepared, and the target analyte can bind to one or more capture reagents in an assay. "Target analyte" also includes any antigenic substances, antibodies, and combinations thereof. The target analyte can include a protein, a peptide, an amino acid, a carbohydrate, a hormone, a steroid, a vitamin, a drug including those administered for therapeutic purposes as well as those administered for illicit purposes, a bacterium, a virus, and metabolites of or antibodies to any of the above substances.

"Test sample" as used herein, means the composition, solution, substance, gas, or liquid containing the target analyte to be detected and assayed using embodiments of the present disclosure. The test sample can contain other components besides the target analyte, can have the physical attributes of a liquid, or a gas, and can be of any size or volume, including for example, a moving stream of liquid or gas. The test sample can contain any substances other than the target analyte as long as the other substances do not interfere with the binding of the target analyte with the capture reagent or the specific binding of the first binding member to the second binding member. Examples of test samples include, but are not limited to, naturally-occurring and non-naturally occurring samples or combinations thereof. Naturally-occurring test samples can be synthetic or synthesized. Naturally-occurring test samples include body or bodily fluids isolated from anywhere in or on the body of a subject including, but not limited to, blood, plasma, serum, urine, saliva or sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, intra-organ system fluid, ascitic fluid, tumor cyst fluid, amniotic fluid and combinations thereof, and environmental samples such as ground water or waste water, soil extracts, air, and pesticide residues or food-related samples.

Detected substances can include, for example, nucleic acids (including DNA and RNA), hormones, different pathogens (including a biological agent that causes disease or illness to its host, such as a virus (e.g., H7N9 or HIV), a protozoan (e.g., *Plasmodium*-causing malaria), or a bacteria (e.g., *E. coli* or *Mycobacterium tuberculosis*)), proteins, antibodies, various drugs or therapeutics or other chemical or biological substances, including hydrogen or other ions, non-ionic molecules or compounds, polysaccharides, small chemical compounds such as chemical combinatorial library members, and the like. Detected or determined parameters may include but are not limited to, for example, pH changes, lactose changes, changing concentration, particles per unit time where a fluid flows over the device for a period of time to detect particles, for example, particles that are sparse, and other parameters.

As used herein, the term "immobilized," when used with respect to, for example, a capture reagent, includes substantially attaching the capture reagent at a molecular level to a surface. For example, a capture reagent may be immobilized to a surface of the substrate material using adsorption techniques including non-covalent interactions (e.g., electrostatic forces, van der Waals, and dehydration of hydrophobic interfaces) and covalent binding techniques where functional groups or linkers facilitate attaching the capture reagent to the surface. Immobilizing a capture reagent to a surface of a substrate material may be based upon the properties of the substrate surface, the medium carrying the capture reagent, and the properties of the capture reagent. In some cases, a substrate surface may be first modified to have functional groups bound to the surface. The functional groups may then bind to biomolecules or biological or chemical substances to immobilize them thereon.

The term "nucleic acid" generally refers to a set of nucleotides connected to each other via phosphodiester bond and refers to a naturally occurring nucleic acid to which a naturally occurring nucleotide existing in nature is connected, such as DNA including deoxyribonucleotides having any of adenine, guanine, cytosine, and thymine connected to each other and/or RNA including ribonucleotides having any of adenine, guanine, cytosine, and uracil connected to each other. Naturally-occurring nucleic acids include, for example, DNA, RNA, and microRNA (miRNA). In addition, non-naturally occurring nucleotides and non-naturally occurring nucleic acids are within the scope of the nucleic acids of the present disclosure. Examples include cDNA, peptide nucleic acids (PNA), peptide nucleic acids with phosphate groups (PHONA), bridged nucleic acids/locked nucleic acids (BNA/LNA), and morpholino nucleic acids. Further examples include chemically-modified nucleic acids and nucleic acid analogues, such as methylphosphonate DNA/RNA, phosphorothioate DNA/RNA, phosphoramidate DNA/RNA, and 2'-O-methyl DNA/RNA. Nucleic acids include those that may be modified. For example, a phosphoric acid group, a sugar, and/or a base in a nucleic acid may be labeled as necessary. Any substances for nucleic acid labeling known in the art can be used for labeling. Examples thereof include but are not limited to radioactive isotopes (e.g., 32P, 3H, and 14C), DIG, biotin, fluorescent dyes (e.g., FITC, Texas, cy3, cy5, cy7, FAM, HEX, VIC, JOE, Rox, TET, Bodipy493, NBD, and TAMRA), and luminescent substances (e.g., acridinium ester).

Aptamer as used herein refers to oligonucleic acids or peptide molecules that bind to a specific target molecule. The concept of using single-stranded nucleic acids (aptamers) as affinity molecules for protein binding was initially disclosed in Ellington, Andrew D., and Jack W. Szostak, "Selection in vitro of single-stranded DNA molecules that fold into specific ligand-binding structures." *Nature* 355 (1992): 850-852; Tuerk, Craig, and Larry Gold, "Systematic evolution of ligands by exponential enrichment: RNA ligands to bacteriophage T4 DNA polymerase." *Science* 249.4968 (1990): 505-510) and is based on the ability of short sequences to fold, in the presence of a target, into unique, three-dimensional structures that bind the target with high affinity and specificity. Ng, Eugene W M, et al. "Pegaptanib, a targeted anti-VEGF aptamer for ocular vascular disease." *Nature Reviews, Drug Discovery* 5.2. (2006): 123, discloses that aptamers are oligonucleotide ligands that are selected for high-affinity binding to molecular targets.

The term "protein" generally refers to a set of amino acids linked together usually in a specific sequence. A protein can be either naturally-occurring or non-naturally occurring. As used herein, the term "protein" includes amino acid sequences, as well as amino acid sequences that have been modified to contain moieties or groups such as sugars, polymers, metalloorganic groups, fluorescent or light-emitting groups, moieties or groups that enhance or participate in a process such as intramolecular or intermolecular electron transfer, moieties or groups that facilitate or induce a protein into assuming a particular conformation or series of conformations, moieties or groups that hinder or inhibit a protein from assuming a particular conformation or series of conformations, moieties or groups that induce, enhance, or inhibit protein folding, or other moieties or groups that are incorporated into the amino acid sequence and that are intended to modify the sequence's chemical, biochemical, or biological properties. As used herein, proteins include, but are not limited to, enzymes, structural elements, antibodies, antigen-binding antibody fragments, hormones, receptors, transcription factors, electron carriers, and other macromolecules that are involved in processes such as cellular processes or activities. Proteins can have up to four structural levels that include primary, secondary, tertiary, and quaternary structures.

The term "antibody" as used herein refers to a polypeptide of the immunoglobulin family that is capable of binding a corresponding antigen non-covalently, reversibly, and in a specific manner. For example, a naturally occurring IgG antibody is a tetramer including at least two heavy (H) chains and two light (L) chains inter-connected by disulfide bonds. Each heavy chain includes a heavy chain variable region (abbreviated herein as VH) and a heavy chain constant region. The heavy chain constant region includes three domains, CH1, CH2 and CH3 Each light chain includes a light chain variable region (abbreviated herein as VL) and a light chain constant region. The light chain constant region includes one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The three CDRs constitute about 15-20% of the variable domains. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. (Kuby, Immunology, 4th ed., Chapter 4. W.H. Freeman & Co., New York, 2000).

The term "antibody" includes, but is not limited to, monoclonal antibodies, human antibodies, humanized antibodies, chimeric antibodies, and anti-idiotypic (anti-Id) antibodies (including, for example, anti-Id antibodies to antibodies of the present disclosure). The antibodies can be of any isotype/class (e.g., IgG, IgE, IgM, IgD, IgA, and IgY), or subclass (e.g., IgG1, IgG2, IgG3, IgG4, IgA1 and IgA2).

The term "antigen binding fragment", as used herein, refers to one or more portions of an antibody that retain the ability to specifically interact with (e.g., by binding, steric hindrance, stabilizing/destabilizing, and spatial distribution) an epitope of an antigen. Examples of binding fragments include, but are not limited to, single-chain Fvs (scFv), camelid antibodies, disulfide-linked Fvs (sdFv), Fab fragments, F(ab') fragments, a monovalent fragment consisting of the VL, VH, CL, and CH1 domains; a F(ab)2 fragment, a bivalent fragment including two Fab fragments linked by a disulfide bridge at the hinge region; a Fd fragment consisting of the VH and CH1 domains; a Fv fragment consisting of the VL and VH domains of a single arm of an antibody; a dAb fragment (Ward, E. Sally, et "Binding activities of a repertoire of single immunoglobulin variable domains secreted from *Escherichia coli.*" *Nature* 341.6242 (1989): 544-546), which consists of a VH domain; and an isolated complementarity determining region (CDR), or other epitope-binding fragments of an antibody.

Furthermore, although the two domains of the Fv fragment (VL, and VH) are coded for by separate genes, they can be joined (using recombinant methods) by a synthetic linker that enables them to be made as a single protein chain, in which the VL and VH regions pair to form monovalent molecules (known as single chain Fv ("scFv"); see, e.g., Bird; Robert E., et al., "Single-chain antigen-binding proteins." *Science* 242.4877 (1988): 423-427; and Huston, James S., et al., "Protein engineering of antibody binding sites: recovery of specific activity in an anti-digoxin single-chain Fv analogue produced in *Escherichia coli.*" *Proceedings of the National Academy of Sciences* 85.16 (1988): 5879-5883). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies; maxibodies, minibodies, single domain antibodies, intrabodies, diabodies, triabodies, tetrabodies, v-NAR, and bis-scFv (see, e.g., Holliger, Philipp, and Peter J. Hudson, "Engineered antibody fragments and the rise of single domains." *Nature Biotechnology* 23.9 (2005): 1126), Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules including a pair of tandem Fv segments (VH—CH1-VH—CH1) which, together with complementary light chain polypeptides, form a pair of antigen binding regions (Zapata, Gerardo, et al., "Engineering linear F(ab')2 fragments for efficient production in *Escherichia coli* and enhanced antiproliferative activity." *Protein Engineering, Design and Selection* 8.10 (1995): 1057-1062 and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "nanoparticles" refers to atomic, molecular or macromolecular particles in the length scale, for example, of approximately 1 to 100 nm. Novel and differentiating properties and functions of nanoparticles are observed or developed at a critical length scale of matter such as, for example, under 100 nm. Nanoparticles may be used in constructing nanoscale structures and may be integrated into larger material components, systems, and architectures. In some embodiments, the critical length scale for novel properties and phenomena involving nanoparticles may be under 1 nm (e.g., manipulation of atoms at approximately 0.1 nm) or it may be larger than 100 nm (e.g., nanoparticle reinforced polymers have the unique feature at approximately 200 to 300 nm as a function of the local bridges or bonds between the nanoparticles and the polymer).

The term "nucleation composition" refers to a substance or mixture that includes one or more nuclei capable of growing into a crystal under conditions suitable for crystal formation. A nucleation composition may, for example, be induced to undergo crystallization by evaporation, changes in reagent concentration, adding a substance such as a precipitant, seeding with a solid material, mechanical agitation, or scratching of a surface in contact with the nucleation composition.

The term "particulate" refers to a cluster or agglomeration of particles such as atoms, molecules, ions, dimers, polymers, or biomolecules. Particulates may include solid matter or be substantially solid, but they may also be porous or partially hollow. They may contain a liquid or gas. In addition, particulates may be homogeneous or heterogeneous; that is, they may include one or more substances or materials.

The term "polymer" means any substance or compound that is composed of two or more building blocks ('mers') that are repetitively linked to each other. For example, a "dimer" is a compound in which two building blocks have been joined together. Polymers include both condensation and addition polymers. Examples of condensation polymers include polyamide, polyester, protein, wool, silk, polyurethane, cellulose, and polysiloxane. Examples of addition polymers are polyethylene, polyisobutylene, polyacrylonitrile, poly(vinyl chloride), and polystyrene. Other examples include polymers having enhanced electrical or optical properties (e.g., a nonlinear optical property) such as electroconductive or photorefractive polymers. Polymers include both linear and branched polymers.

Overview of Exemplary Biosensing Device

FIG. 1 illustrates an overview of components that may be included in a biosensor system 100. Biosensor system 100 includes a sensor array 102 having at least one sensing element for detecting a biological or chemical analyte and a fluid delivery system 104 designed to deliver one or more fluid samples to sensor array 102. Fluid delivery system 104 may be a microfluidic well positioned above sensor array 102 to contain a fluid over sensor array 102. Fluid delivery system 104 may also include microfluidic channels for delivering various fluids to sensor array 102. Fluid delivery system 104 may include any number of valves, pumps, chambers, and/or channels designed to deliver fluid to sensor array 102.

A readout circuit 106 is provided to measure signals from the sensors in sensor array 102 and to generate a quantifiable sensor signal indicative of the amount of a certain analyte that is present in a target solution, according to some embodiments. Different embodiments of readout circuit 106 described herein utilize digital components to reduce power consumption and die area.

A controller 108 may be used to send and receive electrical signals to both sensor array 102 and readout circuit 106 to perform bio- or chemical-sensing measurements. Controller 108 may also be used to send electrical signals to fluid delivery system 104 to, for example, actuate one or more valves, pumps, or motors.

Sensor array 102 may include an array of bioFETs, where one or more of the bioFETs in the array are functionalized to detect a particular target analyte. Different ones of the sensors may be functionalized using different capture reagents for detecting different target analytes. Further details regarding an example design of particular bioFETs are provided below. The bioFETs may be arranged in a plurality of rows and columns, forming a 2-dimensional array of sensors. In some embodiments, each row of bioFETs is functionalized using a different capture reagent. In some embodiments, each column of bioFETs is functionalized using a different capture reagent.

Controller 108 may include one or more processing devices, such as a microprocessor, and may be programmable to control the operation of readout circuit 106 and/or sensor array 102. The details of controller 108 itself are not important for the understanding of the embodiments described herein. However, the various electrical signals that may be sent and received from sensor array 102 will be discussed in more detail below.

Dual Gate Back-Side FET Sensors

Embodiments described herein relate to measuring signals from one or more bioFET sensors, or arrays of bioFET sensors, in a differential manner to reduce common noise between the bioFET sensors. Accomplishing this goal involves controlling the fluid delivery to two separate bioFET sensors, or arrays of bioFET sensors, and differentially reading out the measured signals from each of the bioFET sensors, or arrays of bioFET sensors. This particular section describes an example bioFET sensor design that may be used in the embodiments of the present application.

One example type of bioFET sensor that may be used in sensor array 102 is the dual gate back-side FET sensor. Dual gate back-side FET sensors utilize semiconductor manufacturing techniques and biological capture reagents to form arrayed sensors. While MOSFETs can have a single gate electrode connected to a single electrical node, the dual gate back-side sensing FET sensor has two gate electrodes, each of which is connected to a different electrical node. A first one of the two gate electrodes is referred to herein as a "front-side gate," and the second one of the two gate electrodes is referred to herein as a "back-side gate." Both the front-side gate and the back-side gate are configured such that, in operation, each one may be electrically charged and/or discharged and thereby each influences the electric field between the source/drain terminals of the dual gate back-side sensing FET sensor. The front-side gate is electrically conductive, separated from a channel region by a front-side gate dielectric, and configured to be charged and discharged by an electrical circuit to which it is coupled. The back-side gate is separated from the channel region by a back-side gate dielectric and includes a bio-functionalized sensing layer disposed on the back-side gate dielectric. The amount of electric charge on the back-side gate is a function of whether a bio-recognition reaction has occurred. In the operation of dual gate back-side sensing FET sensors, the front-side gate is charged to a voltage within a predetermined range of voltages. The voltage on the front-side gate determines a corresponding conductivity of the FET sensor's channel region. A relatively small amount of change to the electric charge on the back-side gate changes the conductivity of the channel region. It is this change in conductivity that indicates a bio-recognition reaction.

One advantage of FET sensors is the prospect of label-free operation. Specifically, FET sensors enable the avoidance of costly and time-consuming labeling operations such as the labeling of an analyte with, for instance, fluorescent or radioactive probes.

Figure 2:
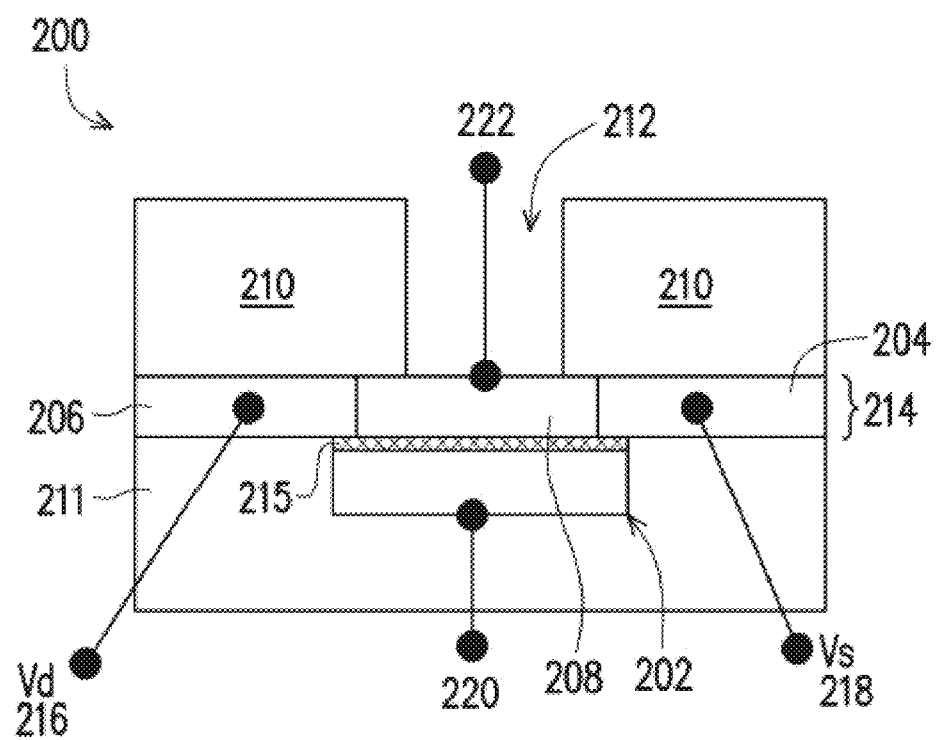
FIG. 2 illustrates a cross-sectional view of an exemplary dual-gate back-side sensing FET sensor, according to some embodiments.

FIG. 2 illustrates an exemplary dual gate back-side sensing FET sensor 200, according to some embodiments. Dual gate back-side sensing FET sensor 200 includes a control gate 202 formed on a surface of substrate 214 and separated therefrom by an intervening dielectric 215 disposed on substrate 214. An interconnect region 211 including a plurality of interconnect layers may be provided over one side of substrate 214. Substrate 214 includes a source region 204, a drain region 206, and a channel region 208 between source region 204 and drain region 206. In some embodiments, substrate 214 has a thickness between about 100 nm and about 130 nm. Gate 202, source region 204, drain region 206, and channel region 208 may be formed using suitable CMOS process technology. Gate 202, source region 204, drain region 206, and channel region 208 form a FET. An isolation layer 210 is disposed on the opposing side of substrate 214 from gate 202. In some embodiments, isolation layer 210 has a thickness of about 1 µm. In this disclosure the side of substrate 214 over which gate 202 is disposed is referred to as the "front-side" of substrate 214. Similarly, the side of substrate 214 on which isolation layer 210 is disposed is referred to as the "back-side."

An opening 212 is provided in isolation layer 210. Opening 212 may be substantially aligned with gate 202. In some embodiments, opening 212 is larger than gate 202 and may extend over multiple dual gate back-side sensing FET sensors. An interface layer (not shown) may be disposed in opening 212 on the surface of channel region 208. The interface layer may be operable to provide an interface for positioning and immobilizing one or more receptors for detection of biomolecules or bio-entities. Further details regarding the interface layer are provided herein.

Dual gate back-side sensing FET sensor 200 includes electrical contacts 216 and 218 to drain region 206 and source region 204, respectively. A front-side gate contact 220 may be made to gate 202, while a back-side gate contact 222 may be made to channel region 208, It should be noted that back-side gate contact 222 does not need to physically contact substrate 214 or any interface layer over substrate 214, Thus, while a FET can use a gate contact to control conductance of the semiconductor between the source and drain (e.g., the channel), dual gate back-side sensing FET sensor 200 allows receptors formed on a side opposing gate 202 of the FET device to control the conductance, while gate 202 provides another region to control the conductance. Therefore, dual gate back-side sensing FET sensor 200 may be used to detect one or more specific biomolecules or bio-entities in the environment around and/or in opening 212, as discussed in more detail using various examples herein.

Dual gate back-side sensing FET sensor 200 may be connected to additional passive components such as resistors, capacitors, inductors, and/or fuses; other active components, including p-channel field effect transistors (PFETs), n-channel field effect transistors (NFETs), metal-oxide-semiconductor field effect transistors (MOSFETs), high voltage transistors, and/or high frequency transistors; other suitable components; or combinations thereof. It is further understood that additional features can be added in dual gate back-side sensing FET sensor 200, and some of the features described can be replaced or eliminated, for additional embodiments of dual gate back-side sensing FET sensor 200.

Figure 3:
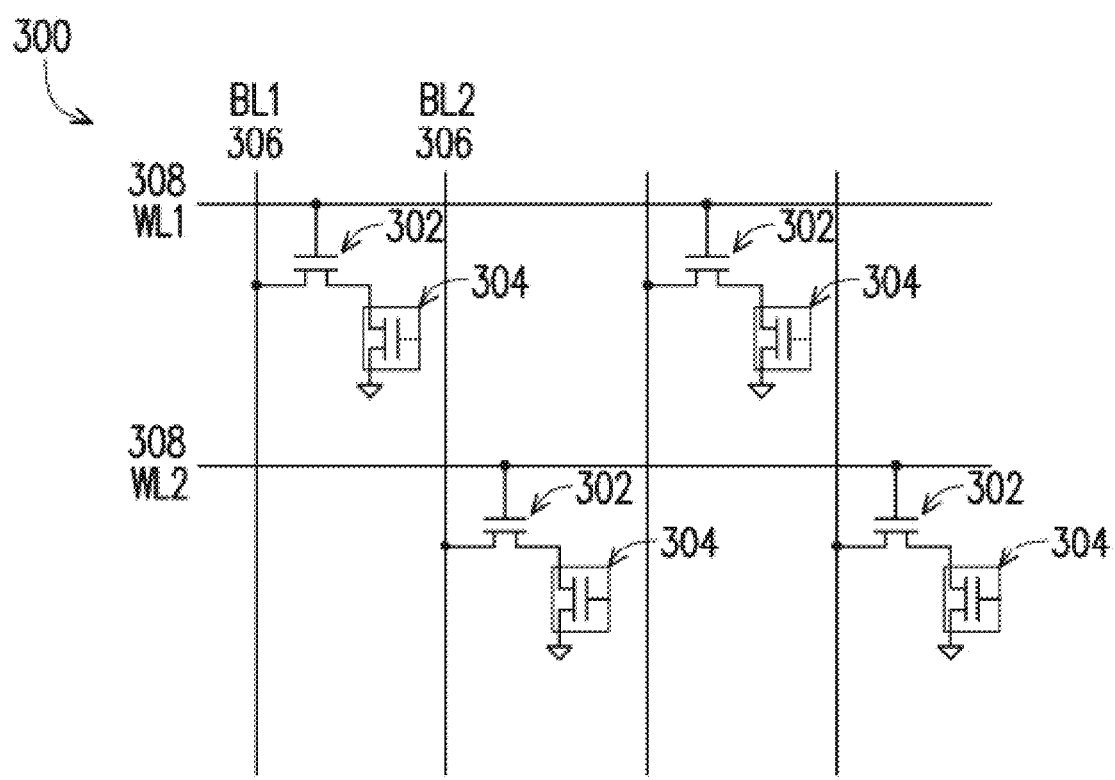
FIG. 3 is a circuit diagram of a plurality of FET sensors configured in an exemplary addressable array, according to some embodiments.

FIG. 3 illustrates a schematic of a portion of an exemplary addressable array 300 of bioFET sensors 304 connected to bit lines 306 and word lines 308. It is noted that the terms bit lines and word lines are used herein to indicate similarities to array construction in memory devices; however, there is no implication that memory devices or a storage array necessarily be included in the array. Addressable array 300 may have similarities to that employed in other semiconductor devices such as dynamic random access memory (DRAM) arrays. For example, dual gate back-side sensing FET sensor 200, described above with reference to FIG. 2; may be formed in a position that a capacitor would be found in a DRAM array. Schematic 300 is exemplary only and one would recognize other configurations are possible.

BioFET sensors 304 may each be substantially similar to dual gate back-side sensing bioFET sensor 200 according to some embodiments. FETs 302 are configured to provide an electrical connection between a drain terminal of bioFET sensor 304 and bit line 306. In this way, FETs 302 are analogous to access transistors in a DRAM array. In some embodiments, bioFET sensors 304 are dual gate back-side sensing FET sensors and each include a sensing gate provided by a receptor material disposed on a dielectric layer overlying a FET channel region disposed at a reaction site, and a control gate provided by a gate electrode (e.g., polysilicon) disposed on a dielectric layer overlying the FET channel region.

Addressable array 300 shows an array formation designed to detect small signal changes provided by biomolecules or bio-entities introduced to bioFET sensors 304. The arrayed format using bit lines 306 and word lines 308 allows for a smaller number of input/output pads since common terminals of different FETs in the same row or column are tied together. Amplifiers may be used to enhance the signal strength to improve the detection ability of the device having the circuit arrangement of schematic 300. In some embodiments, when voltage is applied to particular word lines 308 and bit lines 306, the corresponding access transistors 302 will be turned ON (e.g., like a switch). When the gate of the associated bioFET sensor 304 (e.g., such as back-side gate 222 of the dual gate back-side sensing FET sensor 200) has its charge affected by the bio-molecule presence, a threshold voltage of bioFET sensor 304 is changed, thereby modulating the current (e.g., $I_{ds}$) for a given voltage applied to back-side gate 222. The change of the current (e.g., $I_{ds}$) or threshold voltage ($V_t$) can serve to indicate detection of the relevant biomolecules or bio-entities.

Figure 4:
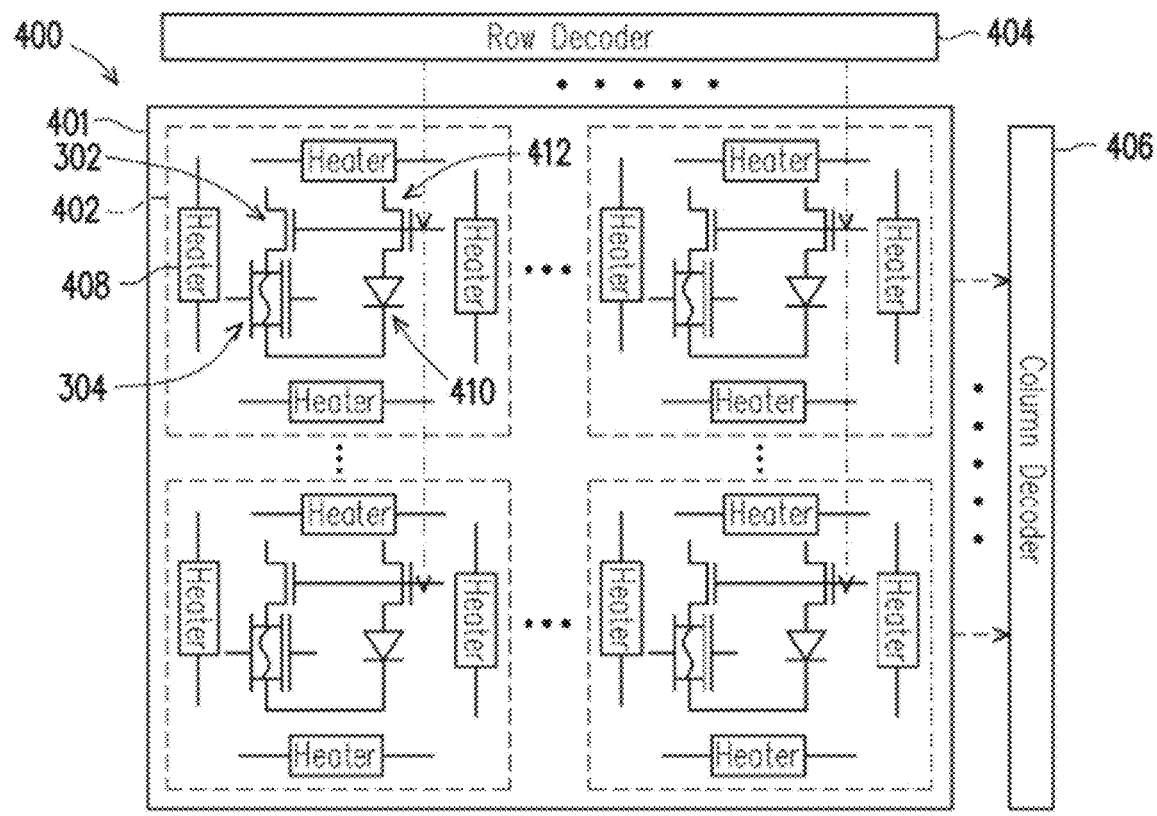
FIG. 4 is a circuit diagram of an exemplary addressable array of dual gate FET sensors and heaters, according to some embodiments.

Referring to FIG. 4, an exemplary schematic 400 is presented. Exemplary schematic 400 includes access transistor 302 and bioFET sensor 304 arranged as an array 401 of individually addressable pixels 402. Array 401 may include any number of pixels 402. For example, array 401 may include 128×128 pixels. Other arrangements may include 256×256 pixels or non-square arrays such as 128× 256 pixels.

Each pixel 402 includes access transistor 302 and bioFET sensor 304 along with other components that may include one or more heaters 408 and a temperature sensor 410. In this example, access transistor 302 is an n-channel FET. An n-channel FET 412 may also act as an access transistor for temperature sensor 410. In some embodiments, the gates of FETs 302 and 412 are connected, though this is not required. Each pixel 402 (and its associated components) may be individually addressed using row decoder 404 and column decoder 406. In some embodiments, each pixel 402 has a size of about 10 micrometers by about 10 micrometers. In some embodiments, each pixel 402 has a size of about 5 micrometers by about 5 micrometers or has a size of about 2 micrometers by about 2 micrometers.

Column decoder 406 and row decoder 404 may be used to control the ON/OFF state of both n-channel FETs 302 and 412 (e.g., voltage is applied to the gates of FETs 302 and 412 together, and voltage is applied to the drain regions of FETs 302 and 412 together). Turning ON n-channel FET 302 provides a voltage to an S/D region of bioFET sensor 304. When bioFET sensor 304 is ON, a current $I_{ds}$ flows through bioFET sensor 304 and may be measured.

Heater 408 may be used to locally increase a temperature around bioFET sensor 304. Heater 408 may be constructed using any known technique, such as forming a metal pattern with a high current running through it. Heater 408 may also be a thermoelectric heater/cooler, like a Peltier device. Heater 408 may be used during certain biological tests such as to denature DNA or RNA or to provide a binding environment for certain biomolecules. Temperature sensor 410 may be used to measure the local temperature around bioFET sensor 304. In some embodiments, a control loop may be created to control the temperature using heater 408 and the feedback received from temperature sensor 410. In some embodiments, heater 408 may be a thermoelectric heater cooler that allows for local active cooling of the components within pixel 402.

Figure 5:
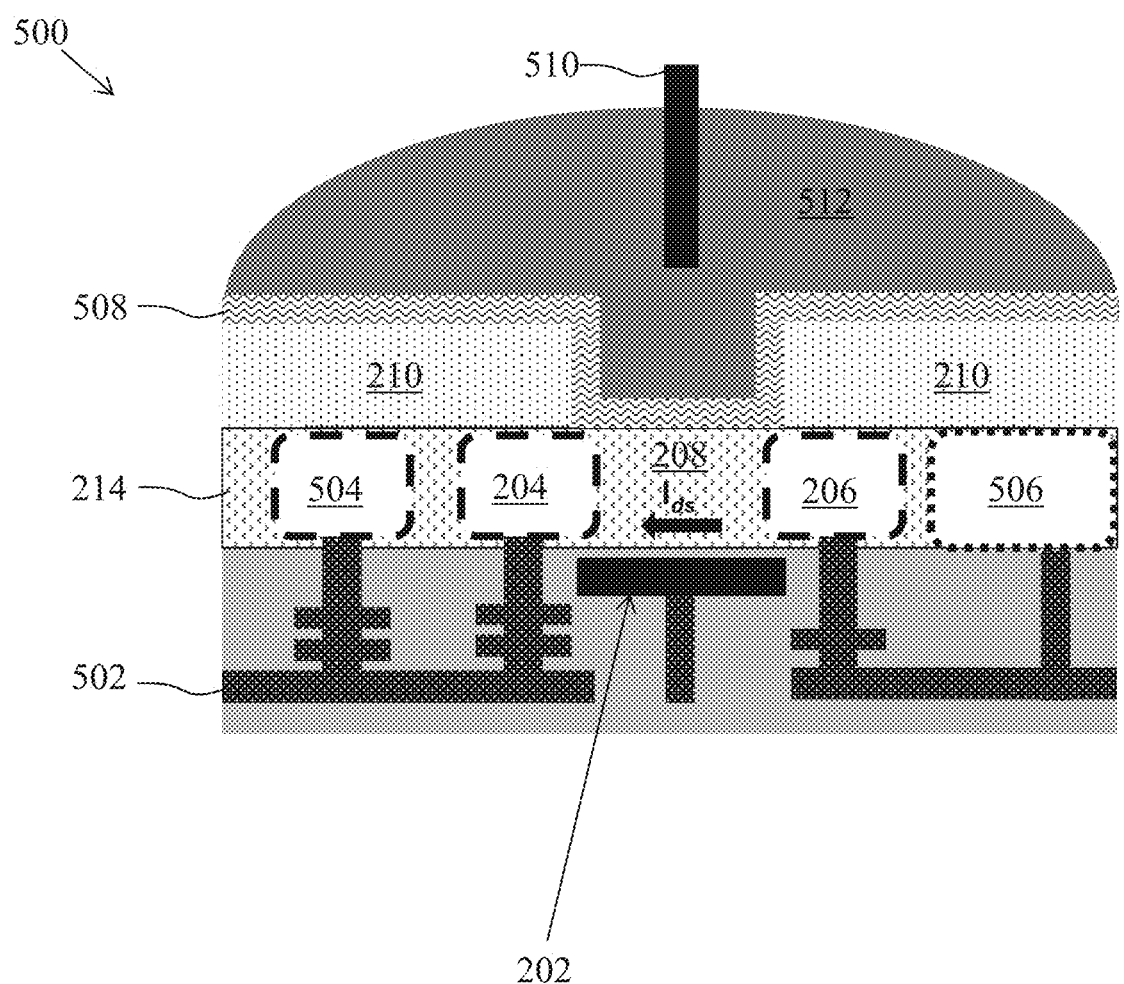
FIG. 5 illustrates a cross-sectional view of an exemplary dual gate back-side sensing FET sensor, according to some embodiments.

Referring to FIG. 5, a cross section of an example dual gate back-side sensing FET sensor 500 is provided, according to some embodiments. The dual gate back-side sensing FET sensor 500 is one implementation of dual gate back-side sensing FET sensor 200. Thus previously described elements from FIG. 2 are labeled with element numbers from FIG. 2 and their descriptions are not repeated here. Dual gate back-side sensing FET sensor 500 includes gate 202, source region 204, drain region 206, and channel region 208, where source region 204 and drain region 206 are formed within substrate 214. Gate 202, source region 204, drain region 206, and channel region 208 form a FET. It should be noted that the various components of FIG. 5 are not intended to be drawn to scale and are exaggerated for visual convenience, as would be understood by a person skilled in the relevant art.

In some embodiments, dual gate back-side sensing FET sensor 500 is coupled to various layers of metal interconnects 502 that make electrical connection with the various doped regions and other devices formed within substrate 214. Metal interconnects 502 may be manufactured using fabrication processes well known to a person skilled in the relevant art.

Dual gate back-side PET sensor 500 may include a body region 504 separate from source region 204 and drain region 206. Body region 504 may be used to bias the carrier concentration in channel region 208 between source region 204 and drain region 206. In some embodiments, a voltage bias may be applied to body region 504 to improve the sensitivity of dual gate back-side PET sensor 500. In some embodiments, body region 504 is electrically connected to source region 204. In some embodiments, body region 504 is electrically grounded.

Dual gate back-side PET sensor 500 may be coupled to additional circuitry 506 fabricated within substrate 214. Circuitry 506 may include any number of MOSFET devices, resistors, capacitors, and/or inductors to form circuitry to aid in the operation of dual gate back-side sensing PET sensor 500. Circuitry 506 may represent a readout circuit used to measure a signal from dual gate back-side PET sensor 500 that is indicative of analyte detection. Circuitry 506 may include amplifiers, analog to digital converters (ADCs), digital to analog converters (DACs), voltage generators, logic circuitry, and/or DRAM memory, to name a few examples. In some embodiments, circuitry 506 includes digital components and does not measure an analog signal from dual gate back-side PET sensor 500. All or some of the components of additional circuitry 506 may be integrated in the same substrate 214 as dual gate back-side PET sensor 500. It should be understood that many PET sensors, each substantially similar to dual gate back-side PET sensor 500, may be integrated in substrate 214 and coupled to additional circuitry 506. In another example, all or some of the components of additional circuitry 506 are provided on another semiconductor substrate separate from substrate 214. In yet another example, some components of additional circuitry 506 are integrated in the same substrate 214 as dual gate back-side PET sensor 500, and some components of additional circuitry 506 are provided on another semiconductor substrate separate from substrate 214.

Still referring to the illustrative example of FIG. 5, dual gate back-side sensing PET sensor 500 includes an interface layer 508 deposited over isolation layer 210 and within the opening over channel region 208. In some embodiments, interface layer 508 has a thickness between about 20 Å and about 40 Å. Interface layer 508 may be a high-K dielectric material, such as hafnium silicate, hafnium oxide, zirconium oxide, aluminum oxide, tantalum pentoxide, hafnium dioxide-alumina ($HfO_2$—$Al_2O_3$) alloy, or any combinations thereof. Interface layer 508 may act as a support for the attachment of capture reagents as will be discussed in more detail later in the section directed to biological sensing. A solution 512 is provided over the reaction site of dual gate back-side sensing FET sensor 500, and a fluid gate 510 is placed within solution 512. Solution 512 may be a buffer solution containing capture reagents, target analytes, wash solution, or any other biological or chemical species.

Figure 6:
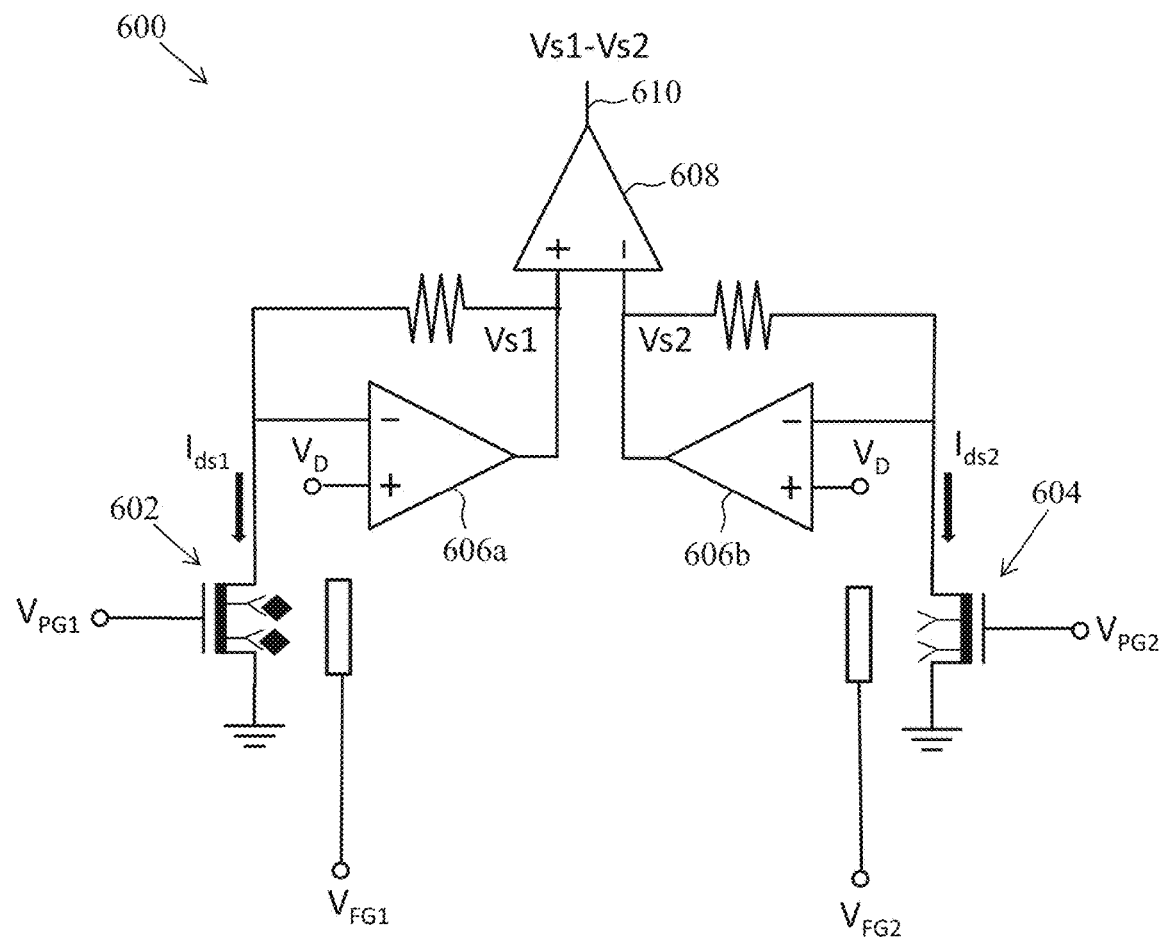
FIG. 6 illustrates a circuit diagram for providing differential sensing between bioFET sensors, according to some embodiments.

FIG. 6 illustrates a differential read out circuit 600 designed to provide a measurement signal 610 that represents a differential measurement between a first bioFET sensor 602 and a second bioFET sensor 604, according to an embodiment. In some examples, each of bioFET sensors 602 and 604 represent distinct arrays of bioFET sensors.

According to an embodiment, both bioFET sensors/arrays 602 and 604 are fabricated together using the same materials for like-elements. For example, each of bioFET sensor/array 602 and 604 use the same material for at least the gate electrode $V_{PG1}$ and $V_{PG2}$) and the same interface layer material upon which the same capture molecules are bound to each bioFET sensor/array 602 and 604. In an embodiment, bioFET sensors/arrays 602 and 604 are designed to be as similar as possible, with the only difference being that bioFET sensor/array 602 is exposed to target analytes while bioFET sensor/array 604 is not.

The differential circuit configuration uses a set of trans-impedance amplifiers 606a and 606b to convert currents from each bioFET/array into a voltage to be compared at differential amplifier 608, according to an embodiment. For example, trans-impedance amplifier 606a converts current $I_{ds1}$ into a corresponding voltage $V_{s1}$. Current $I_{ds1}$ has a magnitude that is dependent on the threshold voltage of bioFET sensor/array 602. The threshold voltage will change if binding with target analytes occurs. Trans-impedance amplifier 606b converts current $I_{ds2}$ into a corresponding voltage $V_{s2}$. Current $I_{ds2}$ has a magnitude that is dependent on the threshold voltage of bioFET sensor/array 604, This threshold voltage is not expected to vary significantly during testing, as bioFET sensor/array 604 is designed to not be exposed to the target analytes. Current $I_{ds1}$ may be generated by applied voltage to either, or both, of gate $V_{PG1}$ and fluid gate $V_{PG2}$ of bioFET sensor/array 602. Similarly, Current $I_{ds2}$ may be generated by applied voltage to either, or both, of gate $V_{PG2}$ and fluid gate $V_{FG2}$ of bioFET sensor/array 604.

According to an embodiment, differential amplifier 608 receives as input a voltage $V_{s1}$ associated with a measurement from bioFET sensor/array 602 and a voltage $V_{s2}$ associated with a measurement from bioFET sensor/array 604. An output signal 610 from differential amplifier 608 provides the difference between voltage $V_{s1}$ and voltage $V_{s2}$. The magnitude of output signal 610 may be used to identify if binding of target analytes occurred, and the concentration of target analytes present. For example, if the magnitude of output signal 610 is zero, or substantially zero, the threshold voltages of bioFET sensors/arrays 602 and 604 are about the same and thus no binding of target analytes has occurred. However, if the magnitude of output signal 610 is some value greater or less than zero, than the absolute magnitude of output signal 610 may be correlated with a concentration of target analytes bound to bioFET sensor/array 602. In some embodiments, differential amplifier 608 has a unity gain. In some embodiments, differential amplifier 608 has a gain greater than one, such as, for example, a gain of 5, 10, 20, 30, 40, 50, or 100.

In an embodiment, each of bioFET sensor/array 602 and 604 represents an array of sensors, such as a 2-dimensional array having rows and columns of connected bioFET sensors. In one example, each bioFET sensor of the bioFET array 602 is electrically coupled to an input of differential amplifier 608 represented by $V_{s1}$ and each bioFET sensor of the bioFET array 604 is electrically coupled to an input of differential amplifier 608 represented by $V_{s2}$. In another example, each bioFET sensor of bioFET array 602 is connected with a corresponding bioFET sensor of bioFET array 604 to its own differential readout circuit. In another example, there is a single differential readout circuit, and each bioFET sensor of bioFET array 602 is connected with a corresponding bioFET sensor of bioFET array 604 to the differential readout circuit at a particular moment in time using a time multiplexing scheme.

Trans-impendence amplifiers 606a and 606b and differential amplifier 608 may each be standard components as would be well known to a person skilled in the relevant art. Trans-impendence amplifiers 606a and 606b may have the same configuration with the same applied gain. According to an embodiment, trans-impendence amplifiers 606a and 606b are provided to maintain a consistent drain voltage of each of bioFET sensor/array 602 and 604. The voltage at terminal VD of either trans-impendence amplifier 606a or 606b may be chosen such that the bioFET sensor/array 602 and 604 are either in linear or saturation mode. In one example, $V_D$=0.2 volts and each of bioFET sensor/array 602 and 604 are in linear mode. In another example, $V_D$=2 volts and each of bioFET sensor/array 602 and 604 are in saturation mode.

Figure 7A:
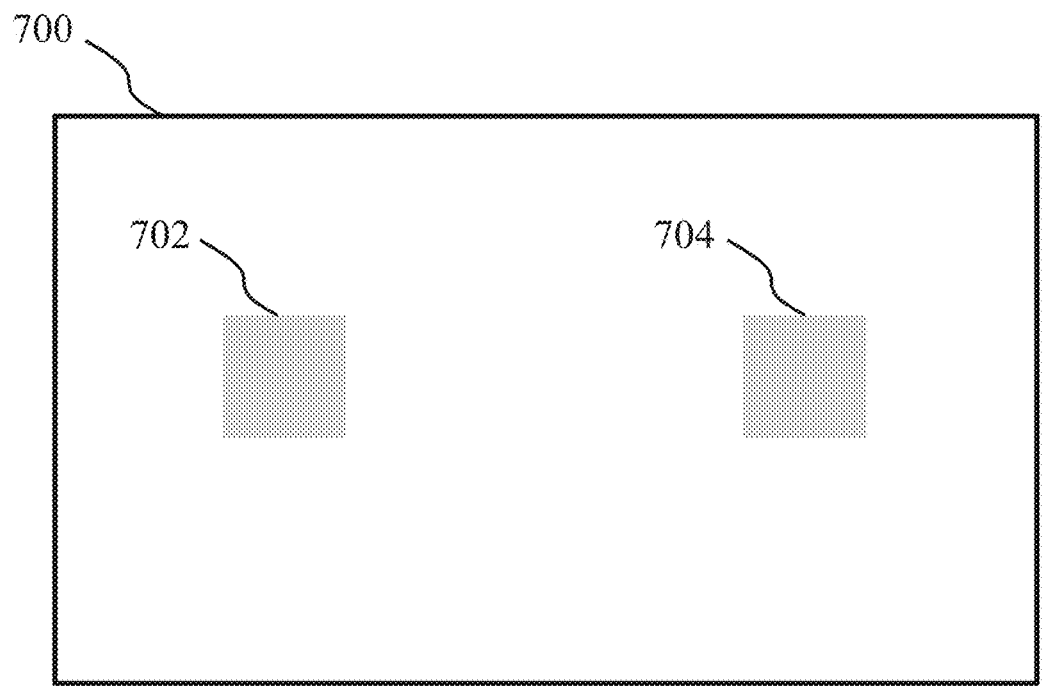
FIGS. 7A and 7B illustrate an arrangement of bioFET sensors, according to some embodiments.

FIG. 7A illustrates a top-down view of a semiconductor device 700 that includes at least two sensing regions 702 and 704, according to an embodiment. Sensing regions 702 and 704 may each include a bioFET sensor. In other examples, sensing regions 702 and 704 each include an array of bioFET sensors, Each of the bioFET sensors may be a dual gate back-side FET sensor like the one illustrated in FIG. 5. Sensing regions 702 and 704 may be separated by a distance sufficiently large to reliably control liquid flow individually over each of sensing regions 702 and 704, as will be discussed in more detail herein.

Figure 7B:
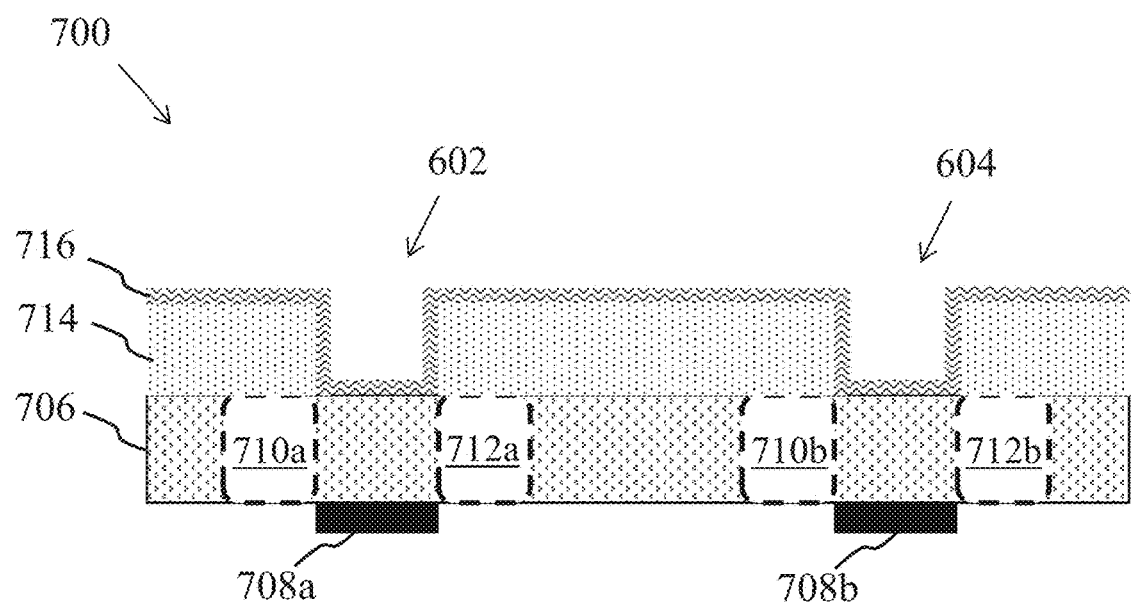

FIG. 7B illustrates a cross-section view of semiconductor device 700, according to an embodiment. For the sake of simplicity, the cross-section view of FIG. 7B illustrates a single bioFET sensor 602 in sensing region 702 and a single bioFET sensor 604 in sensing region 704. However, it should be understood that each of bioFET sensor 602 and bioFET sensor 604 may also represent an array of bioFET sensors.

BioFET sensors 602 and 604 are each dual gate back-side FET sensors, according to an embodiment. BioFET sensors 602 and 604 are formed in the same substrate 706 and are fabricated together using the same processes. Accordingly, bioFET sensors 602 and 604 each have a gate 708a and 708b, respectively, that is formed from the same material and preferably patterned using the same mask. BioFET sensor 602 includes a doped source region 710a and a doped drain region 712a. BioFET sensor 604 also includes a doped source region 710b and a doped drain region 712b having the same doping concentration and profile as doped source region 710a and doped drain region 712a, according to some embodiments. In some embodiments, each of source region 710a, drain region 712a, source region 710b, and drain region 712b is formed at the same time. An isolation layer 714 is disposed over a backside of substrate 706 and openings are formed to expose a channel region of each of bioFET sensors 602 and 604. An interface layer 716 is also deposited within each of the openings and over each channel region of bioFET sensors 602 and 604. In an embodiment, the material used for interface layer 716 is the same over each of bioFET sensors 602 and 604. In an embodiment, interface layer 716 is deposited at the same time over each of bioFET sensors 602 and 604.

Figure 8A:
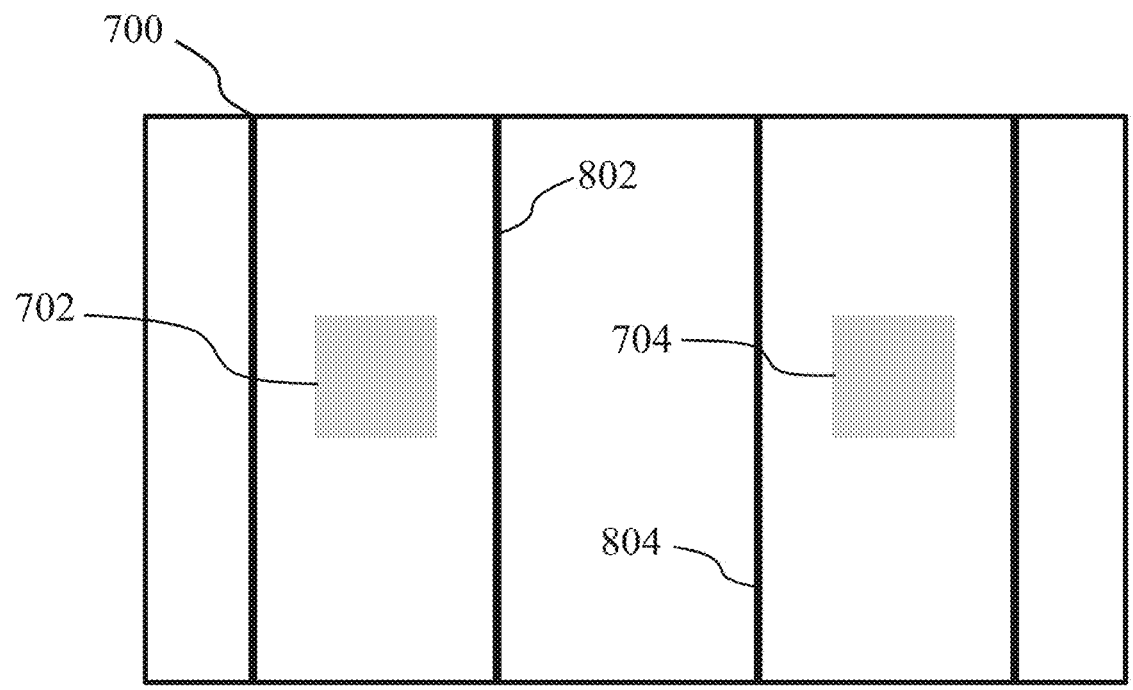
FIGS. 8A and 8B illustrate an arrangement of bioFET sensors with fluidic channels, according to some embodiments.
Figure 8B:
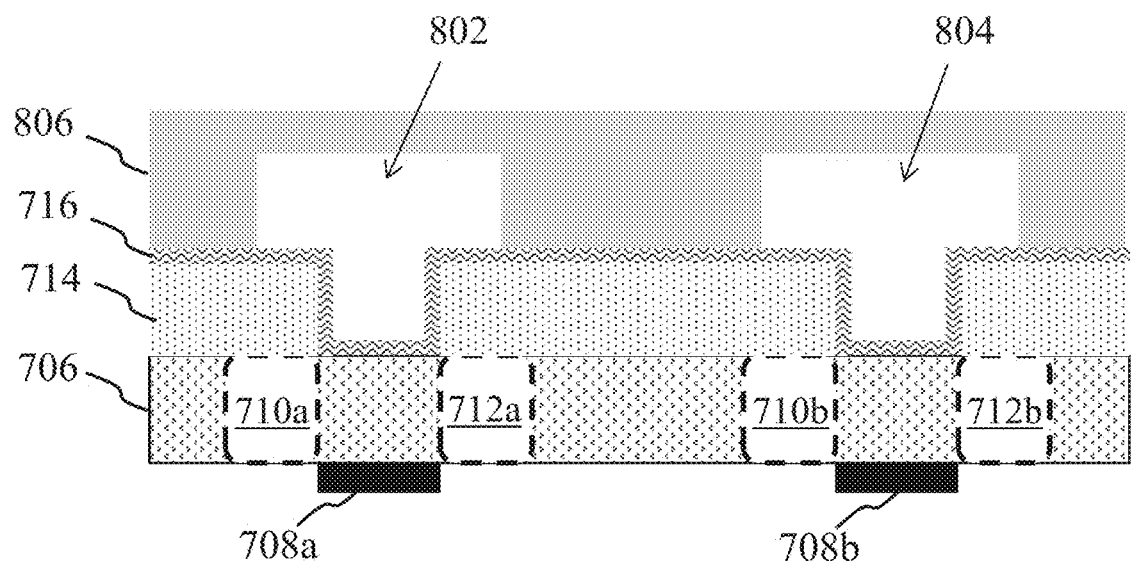

FIGS. 8A and 8B illustrate a top-down view and cross-section view, respectively, of semiconductor device 700 having a microfluidic network positioned over the device, according to an embodiment. The microfluidic network includes at least a first channel 802 and a second channel 804. First channel 802 may be positioned to substantially enclose sensing region 702. Second channel 804 may be positioned to substantially enclose sensing region 704. The fluidic network may be molded in a fluidic layer 806. In some embodiments, fluidic layer 806 is a polymer material such as, for example, polyethylene glycol (PEG) or polydimethylsiloxane (PDMS). In other examples, fluidic layer 806 is a rigid material such as glass or quartz and first channel 802 and second channel 804 are etched into fluidic layer 806. Fluidic layer 806 may be bonded directly on interface layer 716. In some other embodiments, fluidic layer 806 is bonded to interface layer 716 via an adhesion layer disposed between fluidic layer 806 and interface layer 716. In other embodiments, fluidic layer 806 is exposed to an oxygen plasma treatment to enhance its bond strength to interface layer 716. Each of first channel 802 and second channel 804 may be generally any size, however, each channel preferably has a height between about 5 μm and about 500 μm.

In some embodiments, a fluid gate (not shown) may be patterned within each of first channel 802 and second channel 804. The fluid gate may be any conductive material. A potential may be applied to the fluid gate to enhance the charge built up at the backside surface of bioFET sensors 602 or 604.

Figure 9A:
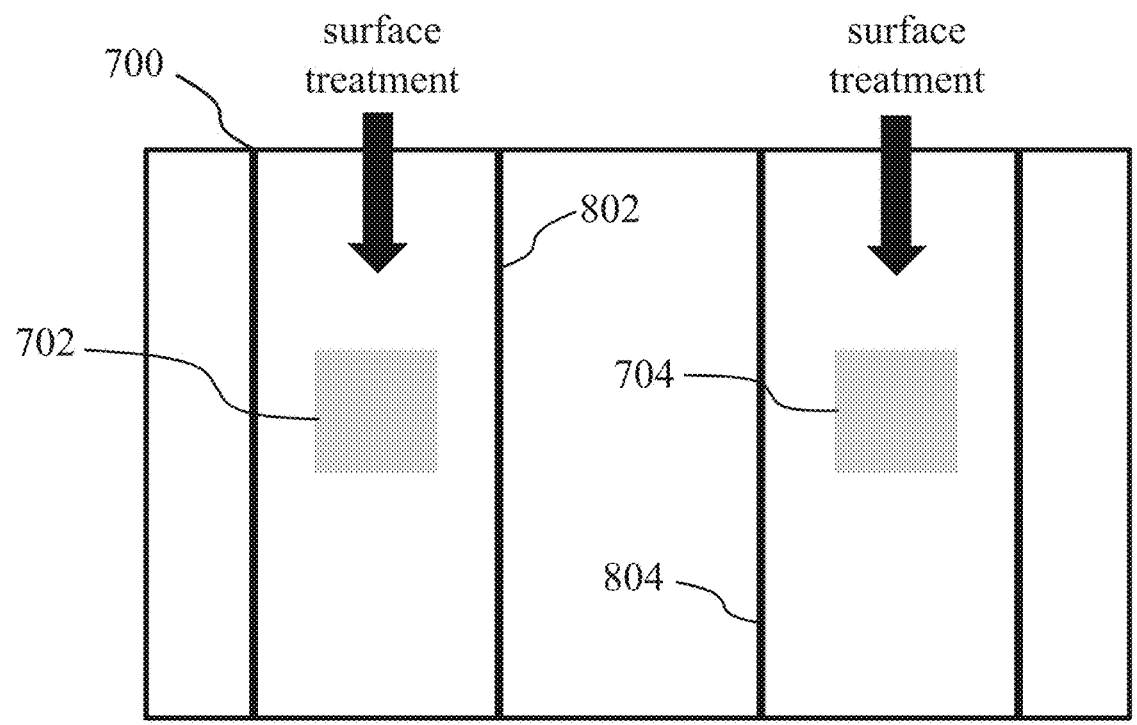
FIGS. 9A and 9B illustrate an arrangement of bioFET sensors with fluidic channels, according to some embodiments.
Figure 9B:
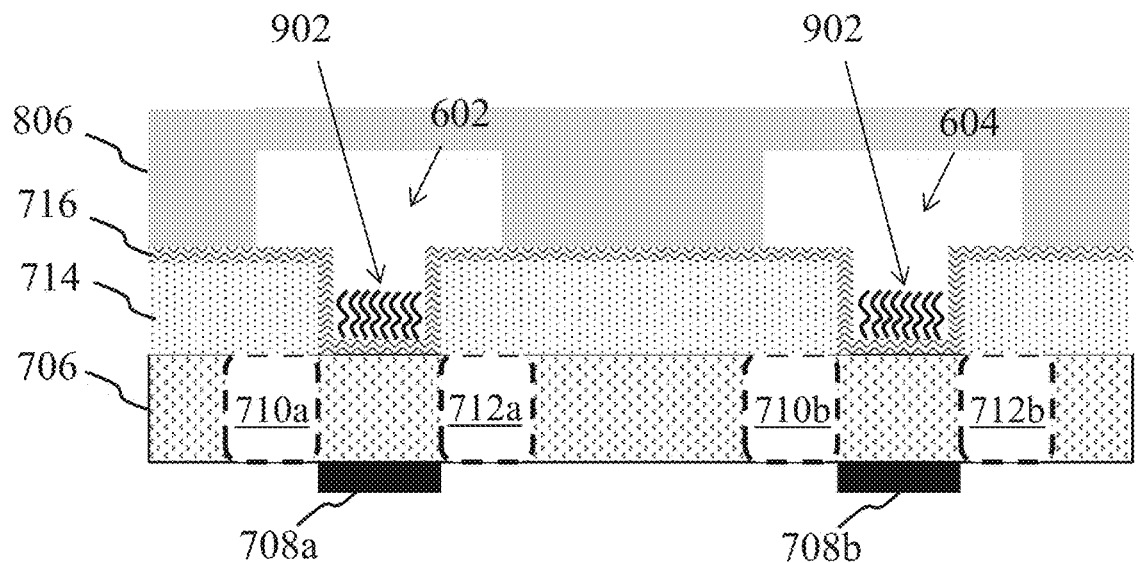

FIGS. 9A and 9B illustrate a top-down view and cross-section view, respectively, of semiconductor device 700 having a microfluidic network where a surface treatment is flown down each channel, according to an embodiment. The same surface treatment may flow through each of first channel 802 and second channel 804, such that the same treatment is applied to the bioFET sensors present at sensing region 702 and sensing region 704.

In some embodiments, the surface treatment includes capture reagents 902 that bind to interface layer 716. Capture reagents 902 are illustrated in FIG. 9B as binding to interface layer 716 within the openings over bioFET sensors 602 and 604. However, it should be understood that capture reagents 902 may bind to any exposed surface of interface layer 716, including any surfaces outside of the openings. The same concentration and type of capture reagents are flown through each of first channel 802 and second channel 804 to ensure consistency between the fabrication of bioFET sensors 602 or 604, according to an embodiment. Examples of capture reagents may include one or more of an enzyme, antibody, ligand, peptide, nucleotide, cell of an organ, organism, or piece of tissue.

After disposing capture reagents 902, an additional surface treatment may be introduced into both first channel 802 and second channel 804 to block any exposed portions of interface layer 716 in an effort to reduce non-specific binding of target analytes, according to an embodiment. Blocking treatments are well known in the art and include, for example, 6-mercaptohexanl and bovine serum albumin (BSA).

At this stage, each of bioFET sensor 602 and bioFET sensor 604 have been fabricated using the same methods and same materials. Ideally, each of bioFET sensor 602 and bioFET sensor 604 has the same device characteristics and response to an applied voltage to gates 708a/708b or to a fluid gate (not shown).

Figure 10A:
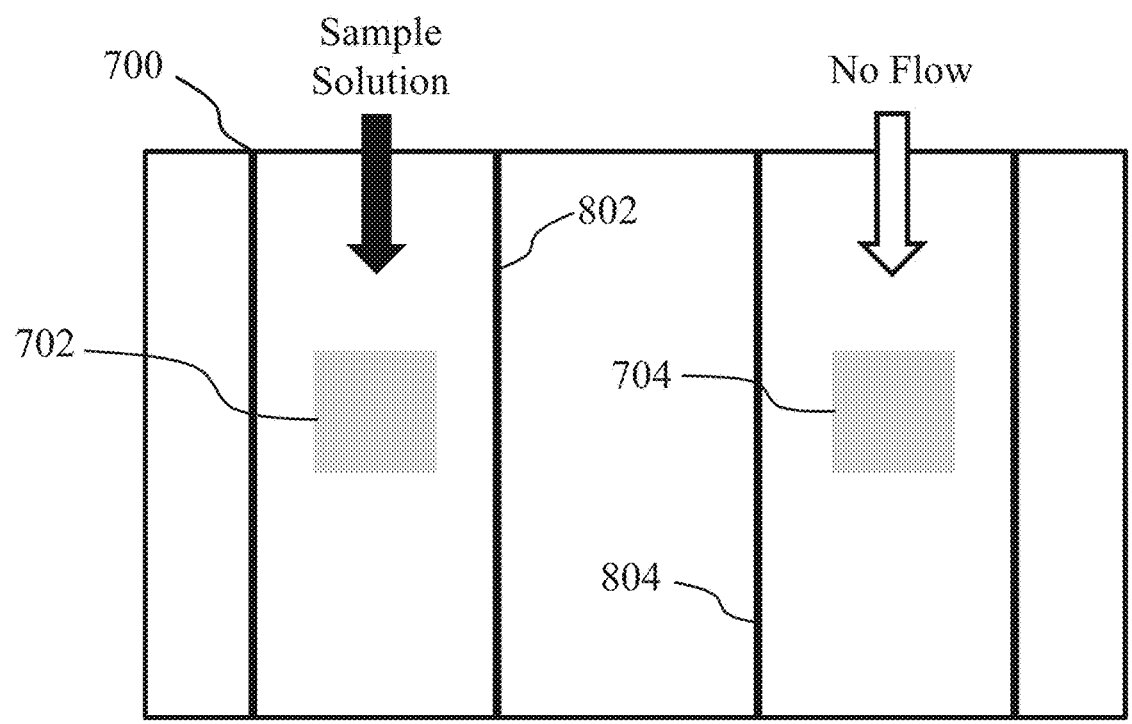
FIGS. 10A and 10B illustrate an arrangement of bioFET sensors with fluidic channels, according to some embodiments.
Figure 10B:
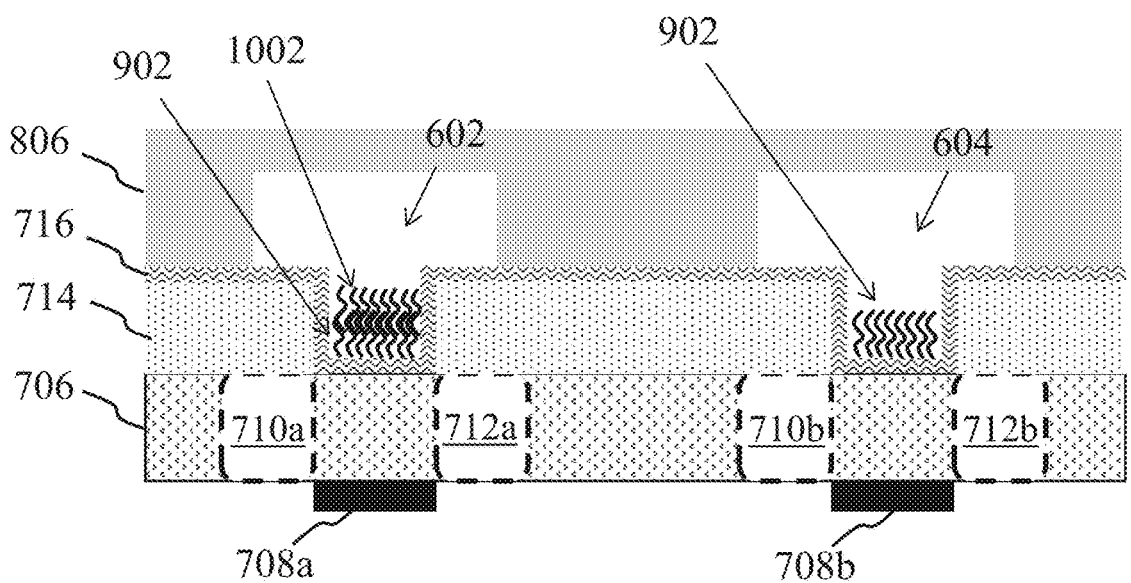

FIGS. 10A and 10B illustrate a top-down view and cross-section view, respectively, of semiconductor device 700 having a microfluidic network where a sample solution is selectively introduced, according to an embodiment, A sample solution containing target analytes 1002 is introduced only into first channel 802. Second channel 804 does not receive the sample solution, however, in some embodiments, a buffer solution not containing target analytes 1002 is introduced into second channel 804 while the sample solution is introduced into first channel 802.

Target analytes 1002 present within the sample solution bind to capture reagents 902 provided over sensing region 702. The binding of the target analytes changes the accumulated charge at the backside surface of bioFET sensor 602 and in turn changes the threshold voltage of bioFET sensor 602. The threshold voltage of bioFET sensor 604 remains unchanged as no target analytes are introduced to sensing region 704. In this way, bioFET sensor 604 acts like a "control" sensor whose output is compared with the output of bioFET sensor 602 (the "actual" sensor.) Examples of target analytes may include one or more of DNA, RNA, antibody, polypeptide, cell, tissue, protein, or tumor marker.

Figure 11A:
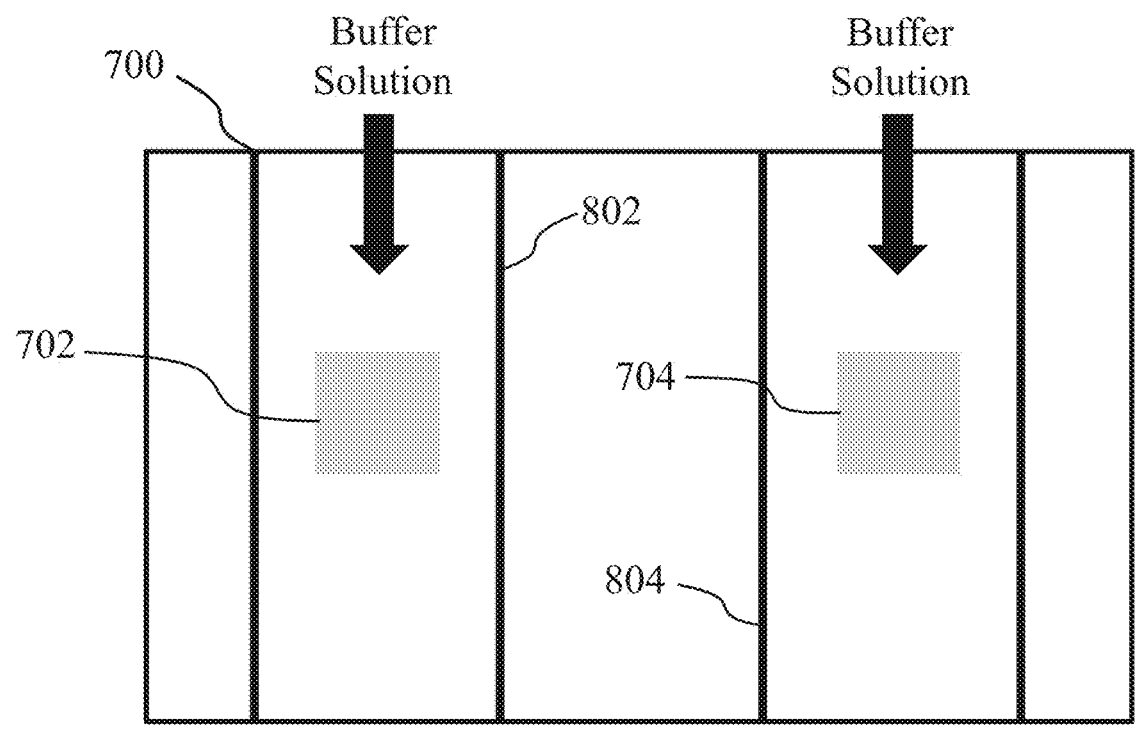
FIGS. 11A and 11B illustrate an arrangement of bioFET sensors with fluidic channels, according to some embodiments.
Figure 11B:
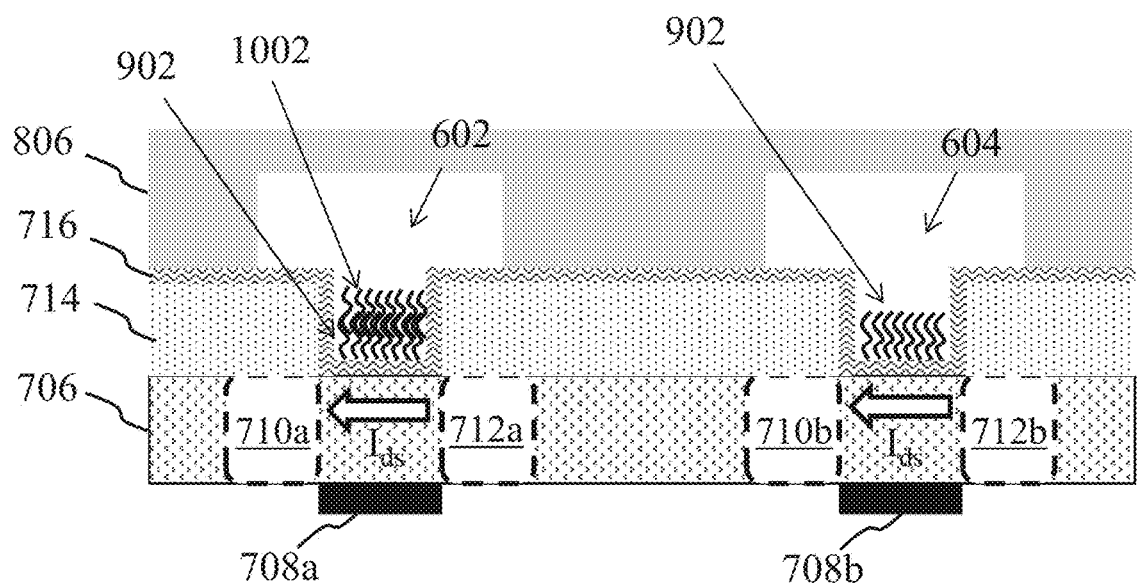

FIGS. 11A and 11B illustrate a top-down view and cross-section view, respectively, of semiconductor device 700 having a microfluidic network where a buffer solution is introduced into each channel for performing a measurement, according to an embodiment. Preferably, the same buffer solution is introduced into each of first channel 802 and second channel 804. In some embodiments, the buffer solution may be preceded by a washing solution introduced into both channels to wash away any unbound material from the channels.

The buffer solution may be any solution having a stable pH value. The same buffer solution is introduced to both first channel 802 and second channel 804 to ensure that the fluid environment around sensing region 702 is the same as the fluid environment around sensing region 704 during the time that measurements are taken from bioFET sensors 602 and 604. The current ($I_{ds}$) from each bioFET sensor 602 and 604 is measured using a differential circuit scheme such as the one illustrated in FIG. 6.

Figure 12A:
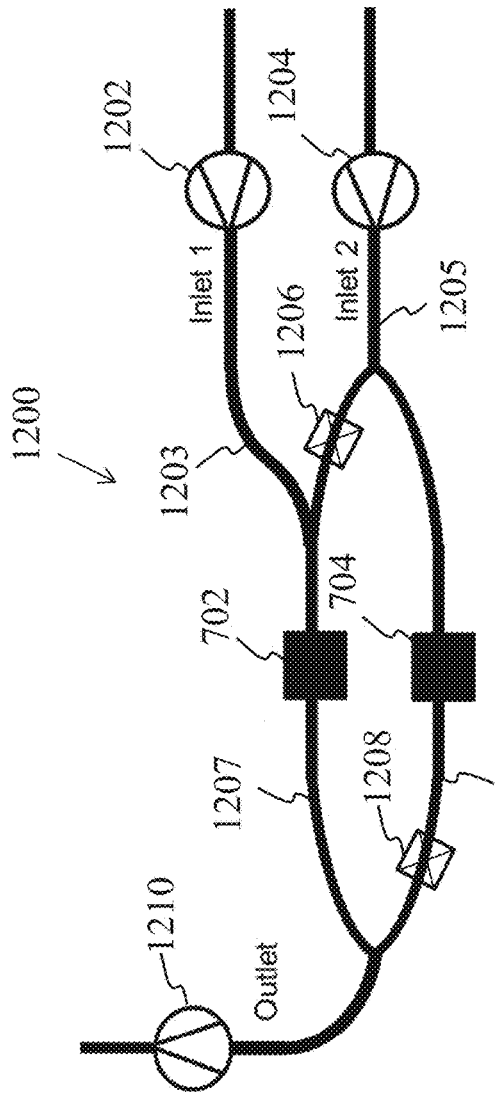
FIGS. 12A and 12B illustrate fluidic layouts for delivering fluids to multiple bioFET sensors, according to some embodiments.
Figure 12B:
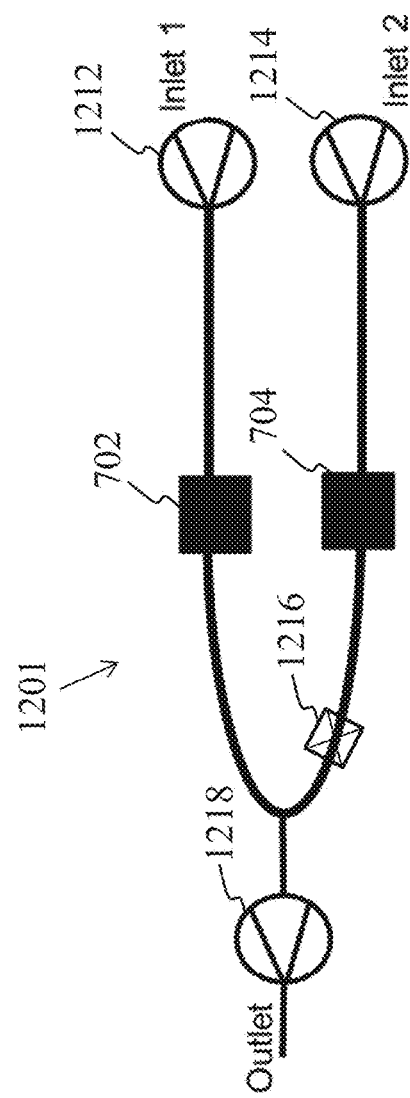

FIGS. 12A and 12B illustrate examples of fluidic networks used to deliver fluid to sensing regions 702 and 704, according to some embodiments. As shown in FIG. 12A, a fluidic network 1200 includes a first fluidic inlet 1202 and a second fluidic inlet 1204 used to deliver fluids to fluidic channel 1203 and fluidic channel 1205, respectively. Fluidic network 1200 also includes a fluidic outlet 1210 which may be a waste reservoir or may include a pressure source to draw fluids through fluidic network 1200. The fluidic inlets may be wells containing a certain amount of fluid, or ports connected with tubing or a syringe needle to introduce fluid. Fluidic network 1200 may include other integrated components such as micropumps or micromixers designed to move and/or disrupt the fluid flow through any of the channels. As would be understood to a person skilled in the relevant art, the micropumps and micromixers may be piezoelectrically or pneumatically actuated.

Fluidic channel 1205 branches into two channels (1207 and 1209) that deliver fluid to each of first sensing region 702 and second sensing region 704, according to an embodiment. As such, fluids that are to be delivered to each of first sensing region 702 and second sensing region 704 may be introduced via second fluidic inlet 1204.

Fluidic channel 1203 joins with fluidic channel 1207 that delivers fluid to first sensing region 702. Due to the geometry of how fluidic channel 1203 joins with fluidic channel 1207, fluid introduced into fluidic inlet 1202 only flows over sensing region 702, but not over sensing region 704. According to an embodiment, to provide better control over the fluid flow, a first valve 1206 and a second valve 1208 may be included to cut off any fluid flow through the valve when it is closed. For example, first valve 1206 and second valve 1208 may each be closed such that a fluid path between first fluidic inlet 1202 and fluidic outlet 1210 is created only through first sensing region 702. First valve 1206 and second valve 1208 may be opened when fluid is delivered over each of first sensing region 702 and second sensing region 704 via second fluidic inlet 1204.

Each of first valve 1206 and second valve 1208 may be any known valve to one skilled in the art. For example, the valves may be piezoelectrically actuated, pneumatically, actuated, or magnetically actuated.

FIG. 12B illustrates another fluidic network 1201 that includes a first fluidic inlet 1212 and a second fluidic inlet 1214 used to deliver fluids to first sensing region 702 and second sensing region 704, respectively. Fluidic network 1201 also includes a fluidic outlet 1218 which may be a waste reservoir or may include a pressure source to draw fluids through fluidic network 1201. The fluidic inlets may be wells containing a certain amount of fluid, or ports connected with tubing or a syringe needle to introduce fluid. Fluidic network 1201 may include other integrated components such as micropumps or micromixers designed to move and/or disrupt the fluid flow through any of the channels. As would be understood to a person skilled in the relevant art, the micropumps and micromixers may be piezoelectrically or pneumatically actuated.

Fluidic network 1201 includes two distinct channels for delivering fluids to first sensing region 702 and second sensing region 704. Thus, the same fluid would be introduced to each of first fluidic inlet 1212 and second fluidic inlet 1214 in order to be received over each of first sensing region 702 and second sensing region 704. In order to deliver fluid only to first sensing region 702, fluid may be delivered only through first fluidic inlet 1212. A valve 1216 may be included to provide better control and ensure, when closed, that fluid meant to be delivered over only first sensing region 702 does not flow back towards second sensing region 704.

According to an embodiment, another fluid delivery mechanism includes patterning an array of electrodes to use in a technique known as electrowetting-on-dielectric (EWOD). Further details regarding the design of EWOD devices and the mechanism behind controlling the movement of fluid droplets using an applied E-field may be found in U.S. Pat. Nos. 9,254,485 and 9,366,647. Briefly, fluid droplets are manipulated in an EWOD environment by generating an electric field between patterned electrodes and a common electrode typically provided along the top of the fluidic channel. The application of the applied E-field modifies the wetting properties of the dielectric surface upon which the droplet rests, which can cause the droplet to move in a given direction depending on which electrodes are activated for applying the E-field.

Figure 13:
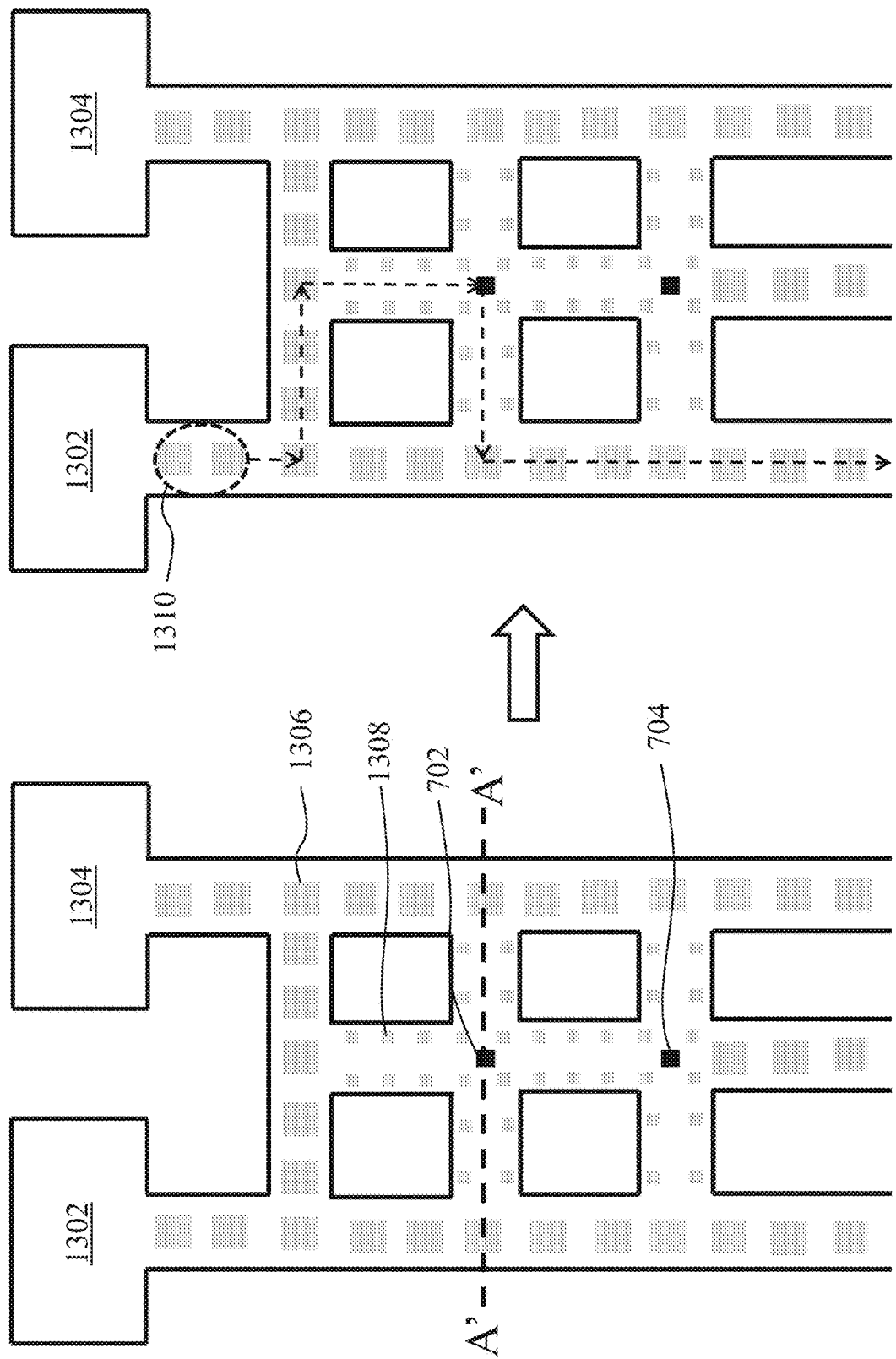
FIG. 13 illustrates a fluidic layout having a plurality of electrodes, according to some embodiments.

FIG. 13 illustrates a top-down view of a channel and electrode arrangement for performing fluid droplet manipulation via. EWOD, according to an embodiment. A first fluid reservoir 1302 and a second fluid reservoir 1304 may be connected to a grid-like arrangement of fluidic channels having patterned major electrodes 1306 and minor electrodes 1308. First sensing area 702 and second sensing area 704 may be provided at different fluidic intersections in the grid. The major electrodes 1306 may be used to provide coarse movement of a fluid droplet while minor electrodes 1308 provide finer and more controlled movement of the fluid droplet. By applying a potential to a series of linked electrodes, a droplet may be moved along a particular path through the fluidic network grid. For example, a fluid droplet 1310 pulled from fluid reservoir 1302 may follow the path shown by the dotted line and arrows by successively applying a potential to the various electrodes along the path. In this way, fluidic droplets can be carefully controlled to move over either, or both, first sensing area 702 and second sensing area 704.

Figure 14:
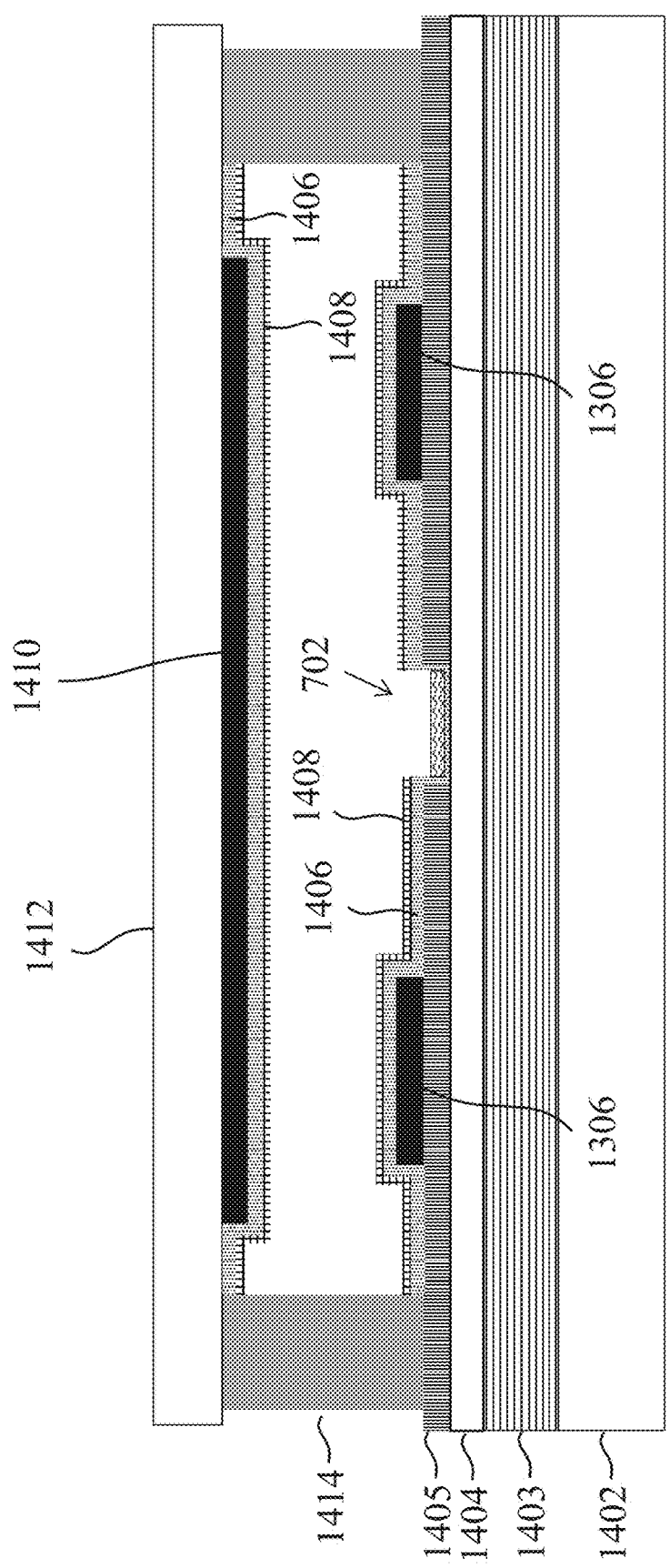
FIG. 14 illustrates a cross-section view of a fluidic layout, according to some embodiments.

FIG. 14 illustrates a cross-section view of an EWOD arrangement for manipulating fluid droplets taken across plane A'-A' illustrated in FIG. 13, according to an embodiment. A carrier substrate 1402 may be provided under a multi-level interconnect structure (MLI) 1403 to give further support to each of the above layers and also to potentially provide a substrate upon which additional circuitry can be fabricated. MLI 1403 may be used to electrically connect the various bioFET sensors provided in first sensing region 702 to at least one of other circuitry, power and ground planes, and bonding pads.

The bioFET sensors of first sensing region 702 are patterned on a substrate 1404 similar to dual gate back-side sensing FET sensor 500 illustrated in FIG. 5. An isolation layer 1405 is provided over substrate 1404 and patterned to form an opening (or plurality of openings) to expose channel region(s) of the bioFET sensors within first sensing region 702.

The EWOD environment includes a top plate 1412 that encloses the fluid channels below. Top plate 1412 may be a glass or silicon substrate. A common electrode 1410 is patterned on an inner surface of top plate 1412. Common electrode 1410 may be any conductor material. In some embodiments, common electrode 1410 is a substantially transparent conductor material to allow for visual inspection of the fluidic channels during operation. Examples of transparent conductors include indium tin oxide (ITO) and aluminum-copper (AlCu). A polymer material may be used to form walls 1414 to enclose the fluidic channel between top plate 1412 and the substrate 1404.

A dielectric layer 1406 is disposed over isolation layer 1405, and also over major electrodes 1306. Dielectric layer 1406 may be a high-K dielectric material, such as hafnium oxide, to name one example. Dielectric layer 1406 is also deposited over the inside of top plate 1412 and over common electrode 1410.

A hydrophobic layer 1408 is disposed over dielectric layer 1406 on both the top and bottom surfaces of the channel. Hydrophobic layer 1408 may generally be any material that exhibits a high hydrophobicity such that a fluid droplet contacting hydrophobic layer 1408 would maintain a high contact angle (e.g., greater than 90 degrees) on hydrophobic layer 1408. Some examples of hydrophobic layer 1408 include Teflon and certain surface assembled monolayers (SAMs) such as 6-mercapto-hexanol.

With this EWOD design, a fluid droplet sandwiched between hydrophobic layer 1408 along the top and bottom of the channel will maintain its position due to the hydrophobic nature of hydrophobic layer 1408. The droplet can then be moved in a given direction by applying an E-field between a corresponding electrode (e.g., major electrode 1306) and common electrode 1410.

Figure 15:
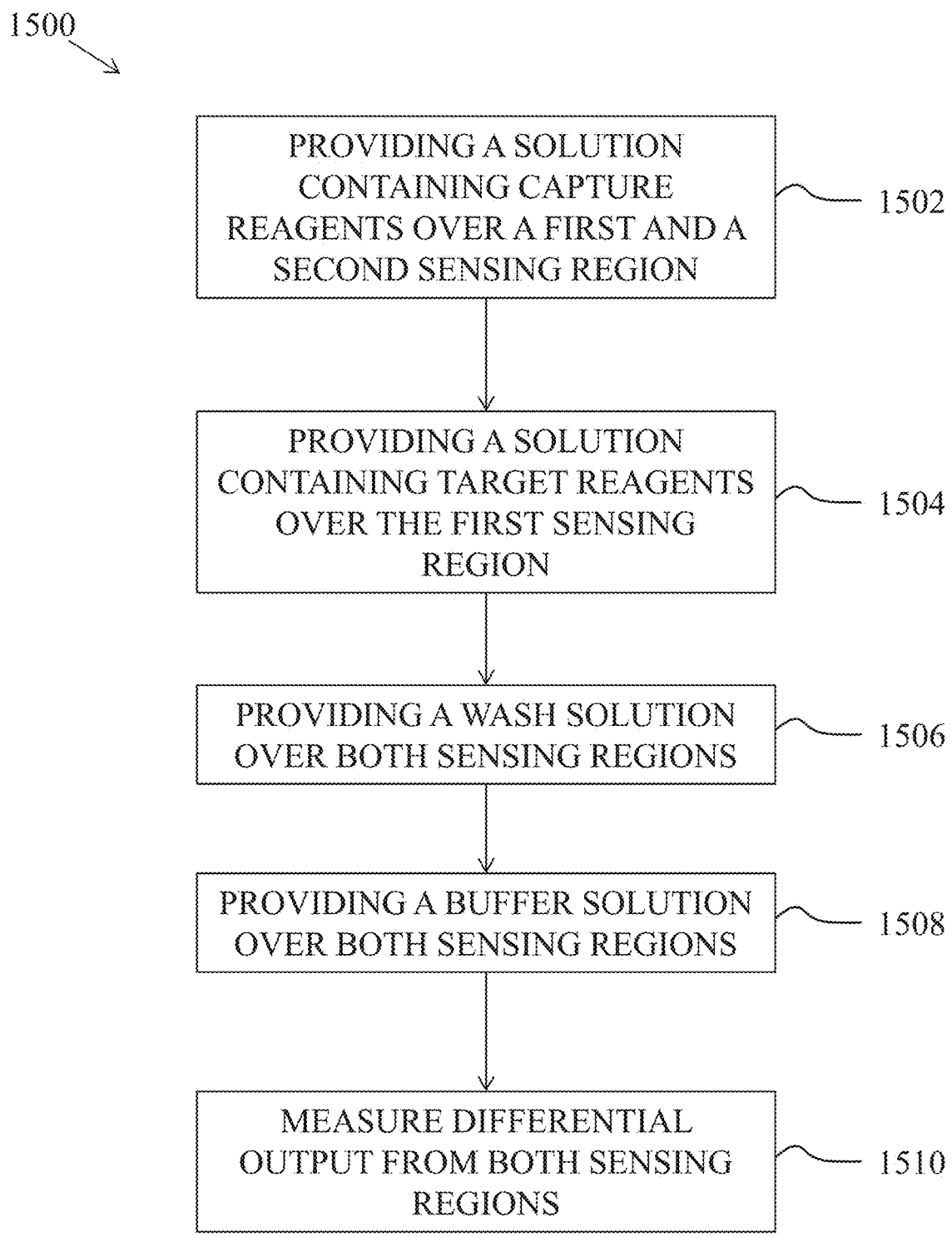
FIG. 15 illustrates a flow diagram of an exemplary method of performing sensing with a plurality of bioFET sensors, according to some embodiments.

FIG. 15 illustrates an example method 1500 for delivering fluid between different sensing regions, according to some embodiments. The different sensing regions may each include one or more (e.g., an array) of bioFET sensors, such as the example dual gate back-side FET sensor illustrated in FIG. 5. It is understood that additional operations can be provided before, during, and after method 1500, and some of the steps described below can be replaced or eliminated, for additional embodiments of the method. In some embodiments, the various operations of method 1500 are illustrated in FIGS. 7-11.

Method 1500 begins at block 1502 where a solution containing capture reagents is introduced over a first and a second sensing region, according to an embodiment. The capture reagents may be suspended in a buffer solution that flows down a single fluidic channel that branches into two fluidic channels with one channel going to the first sensing region and the other channel going to the second sensing region. In another example, the capture reagents are suspended in a buffer solution that flows down two distinct channels, with each channel corresponding to a different sensing region. In yet another example, the capture reagents are suspended in a droplet of buffer solution that is moved over both the first and second sensing regions using an EWOD technique.

The capture reagents bind to the exposed interface layer in each of the first and second sensing regions. The solution containing the capture reagents may be held over each of the first and second sensing regions for a given period of time to ensure sufficient binding of the capture reagents. Example capture reagents may include antibodies, polypeptides, DNA, RNA, cells, viruses, proteins, or enzymes. The capture reagents may be a part of self-assembled monolayer (SAM) of molecules. The SAM may have head groups of silane groups, silyl groups, silanol groups, phosphonate groups, amine groups, thiol groups, alkyl groups, alkene groups, alkyne groups, azido groups, or expoxy groups. The capture reagents are attached to the head groups of the SAM.

Method 1500 then proceeds to block 1504 where a solution containing target analytes is provided over the first sensing region, according to an embodiment. The target analytes may be provided in a buffer solution. The solution may be provided in a way that blocks access to the second sensing region, such that the target analytes are only introduced to the first sensing region. For example, fluidic valves may be used to block off certain channels in a channel network, or separate channels may be used to deliver fluids to either first sensing region or second sensing region. In other examples, an EWOD arrangement may be used to control the movement of a droplet of solution containing the target analytes to only move over the first sensing region, and not move over the second sensing region.

The target analytes bind to the capture reagents present in the first sensing region. The solution containing the target analytes may be held over the first sensing region for a given period of time to ensure sufficient binding of the target analytes. Example target analytes may include antibodies, polypeptides, DNA, RNA, cells, viruses, proteins, or enzymes.

Method 1500 proceeds to block 1506 where a wash solution is provided over both the first and second sensing region, according to an embodiment. Block 1506 is optional and may be performed to help wash away any unbound material from the first sensing region that could distort or disrupt the signal measurement. The same wash solution is also provided to the second sensing region to ensure consistency between the two sensing regions (except for the introduction of the target analytes) up until both sensing regions are used for measurement.

Method 1500 proceeds to block 1508 where a buffer solution is provided over both the first and second sensing regions, according to an embodiment. The buffer solution may be provided to create a liquid environment having a stable pH in order to perform a measurement with the bioFET sensor(s) in each of the first and second sensing regions.

Method 1500 proceeds to block 1510 where a differential output is measured from the bioFET sensor(s) in each of the first and second sensing regions, according to an embodiment. The differential output may be measured using a differential amplifier circuit, such as differential read out circuit 600 illustrated in FIG. 6. Because the bioFET sensor(s) in each of the first and second sensing regions are fabricated at the same time and with the same materials, their output response to a same applied gate voltage should be substantially the same, with any difference only being caused by the presence of the target analytes in the first sensing region. Because of this, differential measurement between the bioFET sensor(s) of the first and second sensing regions will cancel out any environmental noise or noise due to drift that similarly effect each of the bioFET sensors. The resulting differential measurement is thus a cleaner signal that can be used to detect lower concentrations of target analytes compared to prior methods.

Figure 16:
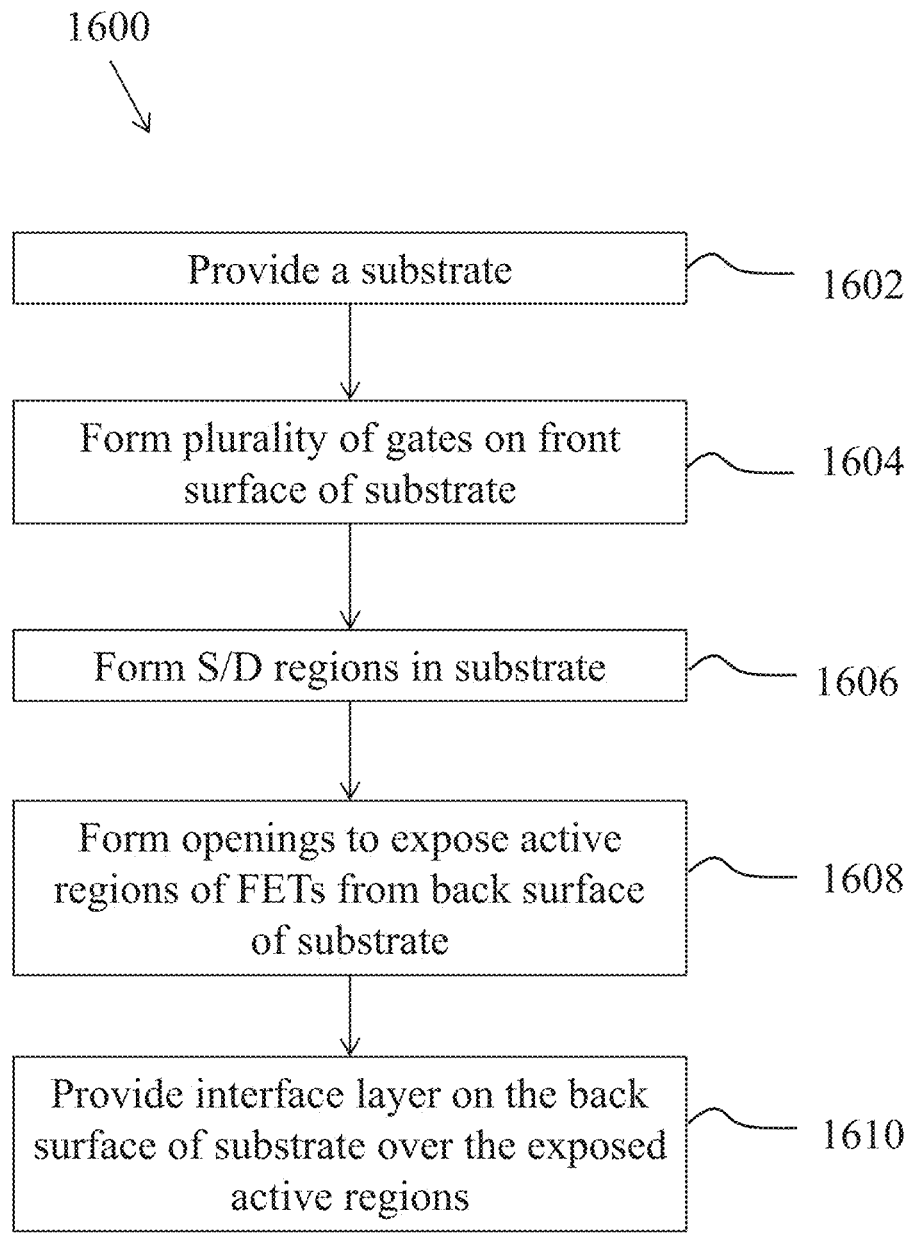
FIG. 16 illustrates a flow diagram of an exemplary method of fabricating a plurality of dual gate back-side sensing FET sensors, according to some embodiments.

FIG. 16 illustrates an example method 1600 for fabricating a plurality of dual gate back-side FET sensors such as the one illustrated in FIG. 5, according to some embodiments. The plurality of dual gate back-side FET sensors may be provided in the first and second sensing regions discussed herein for performing differential sensing between the bioFET sensors. Method 1600 may include forming the dual gate back-side FET sensors using one or more process steps compatible with or typical to a complementary metal-oxide-semiconductor (CMOS) process. It is understood that additional operations can be provided before, during, and after method 1600, and some of the steps described below can be replaced or eliminated, for additional embodiments of the method. Further, it is understood that method 1600 includes operations having features of a typical CMOS technology process flow and thus, are only described briefly herein. Typical CMOS technology processes may include photolithography; ion implantation; diffusion; deposition including physical vapor deposition (PVD), metal evaporation or sputtering, chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), atomic layer CVD (ALCVD), spin on coating; and etching including wet etching, dry etching, and plasma etching. Reference may be made to certain elements illustrated in FIG. 5.

Method 1600 begins at block 1602 where a substrate is provided. The substrate may be a semiconductor substrate. The semiconductor substrate may be a silicon substrate. Alternatively, the substrate may include another elementary semiconductor, such as germanium; a compound semiconductor including silicon carbide; an alloy semiconductor including silicon germanium; or combinations thereof. In some embodiments, the substrate is a semiconductor on insulator (SOI) substrate. The substrate may include doped regions, such as p-wells and n-wells. In the present disclosure, a wafer is a workpiece that includes a semiconductor substrate and various features formed in and over and attached to the semiconductor substrate. The wafer may be in various stages of fabrication and is processed using the CMOS process. After the various stages of fabrication are completed, the wafer is separated into individual dies that are packaged into an integrated chip.

Method 1600 then proceeds to block 1604 where a plurality of gates are formed on a front surface of the substrate. A first set of the plurality of gates may act as gates of dual gate back-side FET sensors present in the first sensing region while a second set of the plurality of gates may act as gates of dual gate back-side FET sensors present in the second sensing region. According to some embodiments, the gates are polysilicon. Other exemplary gate materials include metals such as, copper (Cu), tungsten (W), titanium (Ti), tantalum (Ta), chromium (Cr), platinum (Pt), silver (Ag), gold (Au); suitable metallic compounds like titanium nitride (TiN), tantalum nitride (TaN), nickel silicide (NiSi), cobalt silicide (CoSi); combinations thereof; and/or other suitable conductive materials.

A gate dielectric is provided between the plurality of gates and the front surface of the substrate. In some embodiments, the gate dielectric is silicon oxide. Other exemplary gate dielectrics include silicon nitride, silicon oxynitride, a dielectric with a high dielectric constant (high k), or combinations thereof. Examples of high k materials include hafnium silicate, hafnium oxide, zirconium oxide, aluminum oxide, tantalum pentoxide, hafnium dioxide-alumina ($HfO_2$—$Al_2O_3$) alloy, or combinations thereof.

Method 1600 proceeds to block 1606 where S/D regions are formed in the substrate on either side of each of the plurality of gates. The S/D regions may include n-type dopants or p-type dopants depending on the FET configuration (i.e., n-channel or p-channel.) S/D regions of the dual gate back-side FET sensors may be formed at the same time. Additional interconnect layers may be formed to create electrical connections to each of the plurality of gates and S/D regions, such as metal interconnects 502 illustrated in FIG. 5.

In some embodiments, a carrier substrate may also be attached to the interconnect layers to allow for various subsequent operations to the back side of the substrate without affecting the structural integrity of the semiconductor substrate. In some embodiments, the carrier substrate is bonded to a last metal interconnect layer of the interconnect layers. In some embodiments, the carrier substrate is bonded to a passivation layer formed on the interconnect layers. The carrier substrate may be attached to the device substrate using fusion, diffusion, eutectic, and/or other suitable bonding methods. Exemplary compositions for the carrier substrate include silicon, glass, and quartz. In some embodiments, the carrier substrate may include other functionality such as interconnect features, bonding sites, defined cavities, and/or other suitable features. The carrier substrate may be removed during subsequent processing (e.g., after thinning).

Method 1600 proceeds to block 1608 where openings are formed through a dielectric layer on the back side of the substrate, according to some embodiments. For example, openings may be etched through isolation layer 714 (as shown in FIG. 7B) to expose the back side of substrate 706 within a first sensing region 702 and a second sensing region 704. A single large opening in each of first sensing region 702 and a second sensing region 704 may encompass more than one dual gate back-side FET sensor, according to some embodiments. In some other embodiments, openings are formed over each individual dual gate back-side FET sensor.

The openings may be formed by first performing a dry etch such as a reactive ion etch (RIE) or any plasma etch to thin the dielectric layer on the back side of the substrate. Afterwards, the thin remaining portion of the dielectric layer within the opening may be removed using a wet etch, such as a buffered oxide etch (BOE) or hydrofluoric acid (HF).

Method 1600 proceeds to block 1610 where an interface layer (e.g. layer 716 illustrated in FIG. 7B) is disposed on the back surface of the substrate over the exposed channel regions within the openings, according to some embodiments. The interface layer is compatible for biomolecule or bio-entity binding. For example, the interface layer may provide a binding interface for biomolecules or bio-entities. The interface layer may include a dielectric material, a conductive material, and/or other suitable material for holding a receptor. Exemplary interface materials include high-k dielectric films, metals, metal oxides, dielectrics, and/or other suitable materials. As a further example, exemplary interface layer materials include: hafnium oxide ($HfO_2$), tantalum oxide ($Ta_2O_5$), Pt, Au, W, Ti, aluminum (Al), Cu; oxides of such metals such as, for example, silicon dioxide ($SiO_2$), silicon nitride ($Si_3N_4$), aluminum oxide ($Al_2O_3$), titanium oxide ($TiO_2$), TiN, zirconium oxide ($ZrO_2$), tin (II) oxide (SnO), tin dioxide ($SnO_2$); and/or other suitable materials. The interface layer may be formed using CMOS processes such as, for example, physical vapor deposition (PVD) (sputtering), chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), or atomic layer CVD (ALCVD). In some embodiments, the interface layer includes a plurality of layers.

Chemistry, Biology, and Interface

An example operation of dual gate back-side FET sensor 502 as a pH sensor will now be described with reference to FIG. 5. Although the opening over dual gate back-side FET sensor 500 is illustrated as only being over channel region 208, it should be understood that the opening may stretch further to expose other dual gate back-side FET sensors, and that the size of the opening does not change the bio-sensing operations described herein.

Briefly, a fluid gate 510 is used to provide an electrical contact to the "back gate" of dual gate back-side FET sensor 500. A solution 512 is provided over the reaction site of dual gate back-side FET sensor 500, and fluid gate 510 is placed within solution 512. The pH of the solution is generally related to the concentration of hydrogen ions [$H^+$] in the solution. The accumulation of the ions near the surface of interface layer 508 above channel region 208 affects the formation of the inversion layer within channel region 208 that forms the conductive pathway between S/D regions 204 and 206. In some embodiments, a current $I_{ds}$ flows from one S/D region to the other.

The current $I_{ds}$ may be measured to determine the pH of solution 512. In some embodiments, fluid gate 510 is used as the gate of the transistor during sensing while gate 202 remains floating. In some embodiments, fluid gate 510 is used as the gate of the transistor during sensing while gate 202 is biased at a given potential. For example, gate 202 may be biased at a potential between –2V and 2V depending on the application, while fluid gate 510 is swept between a range of voltages, or is held at a constant voltage. In some embodiments, fluid gate 510 is biased at a given potential (or grounded) while the voltage applied to gate 202 is swept across a range of potentials, or is held at a constant voltage, during sensing. Fluid gate 510 may be formed from platinum or may be formed from any other commonly used material(s) for reference electrodes in electrochemical analysis. An example of a reference electrode is a silver/silver chloride (Ag/AgCl) electrode, which has a stable potential value of about 0.230 V.

Figure 17B:
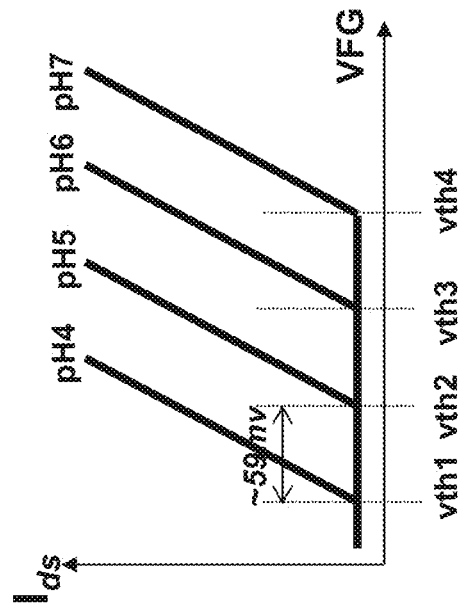
FIGS. 17A and 17B illustrate using the dual gate back-side sensing FET sensor as a pH sensor, according to some embodiments.
Figure 17A:
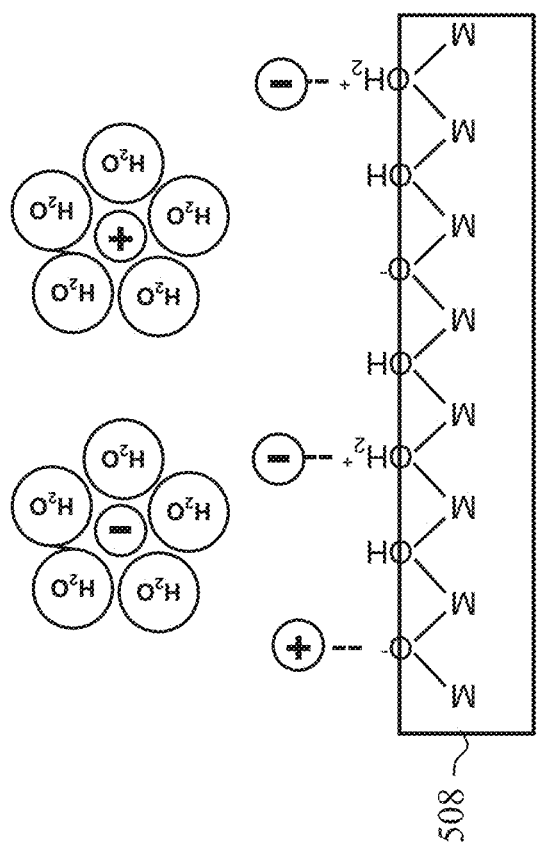

FIG. 17A shows ions in solution binding to a surface of interface layer 508. A top-most atomic layer of interface layer 508 is depicted as the various dangling [$O^-$], [OH], and [$OH_2^+$] bonds. As the ions accumulate on the surface, the total surface charge affects the threshold voltage of the transistor. As used herein, the threshold voltage is the minimum potential between the gate and the source of a FET sensor that is required to form a conductive path of carriers between the source and the drain of the FET sensor. The total charge also directly relates to a pH of the solution, as a higher accumulation of positive charge signifies a lower pH while a higher accumulation of negative charge signifies a higher pH.

FIG. 17B illustrates an example change in threshold voltage that results due to different pH values in an n-channel FET sensor. As can be observed in this example, a 59 mV increase in threshold voltage roughly signifies an increase of one in the pH of the solution. In other words, one pH change results in total surface charge equivalent of 59 mV when measured as the voltage required to turn ON the transistor.

Changing the threshold voltage of dual gate back-side FET sensor 500 also changes a time it takes to form a conductive path between SA) regions 204 and 206 for a given voltage input to either fluid gate 510 or gate 202. This time delay in "turning ON" the FET sensor may be quantified using digital circuitry and used to determine an analyte concentration, according to some embodiments.

The apparatus, systems, and methods described in this application can be used to monitor interactions between various entities. These interactions include biological and chemical reactions to detect target analytes in a test sample. As an example, reactions, including physical, chemical, biochemical, or biological transformations, can be monitored to detect generation of intermediates, byproducts, products, and combinations thereof. In addition, the apparatus, systems, and methods of the present disclosure can be used to detect these reactions in various assays as described herein, including, but not limited to, circulating tumor cell assays used in liquid biopsies and chelation assays to detect the presence of heavy metals and other environmental pollutants. Such assays and reactions can be monitored in a single format or in an array format to detect, for example, multiple target analytes.

Figure 18:
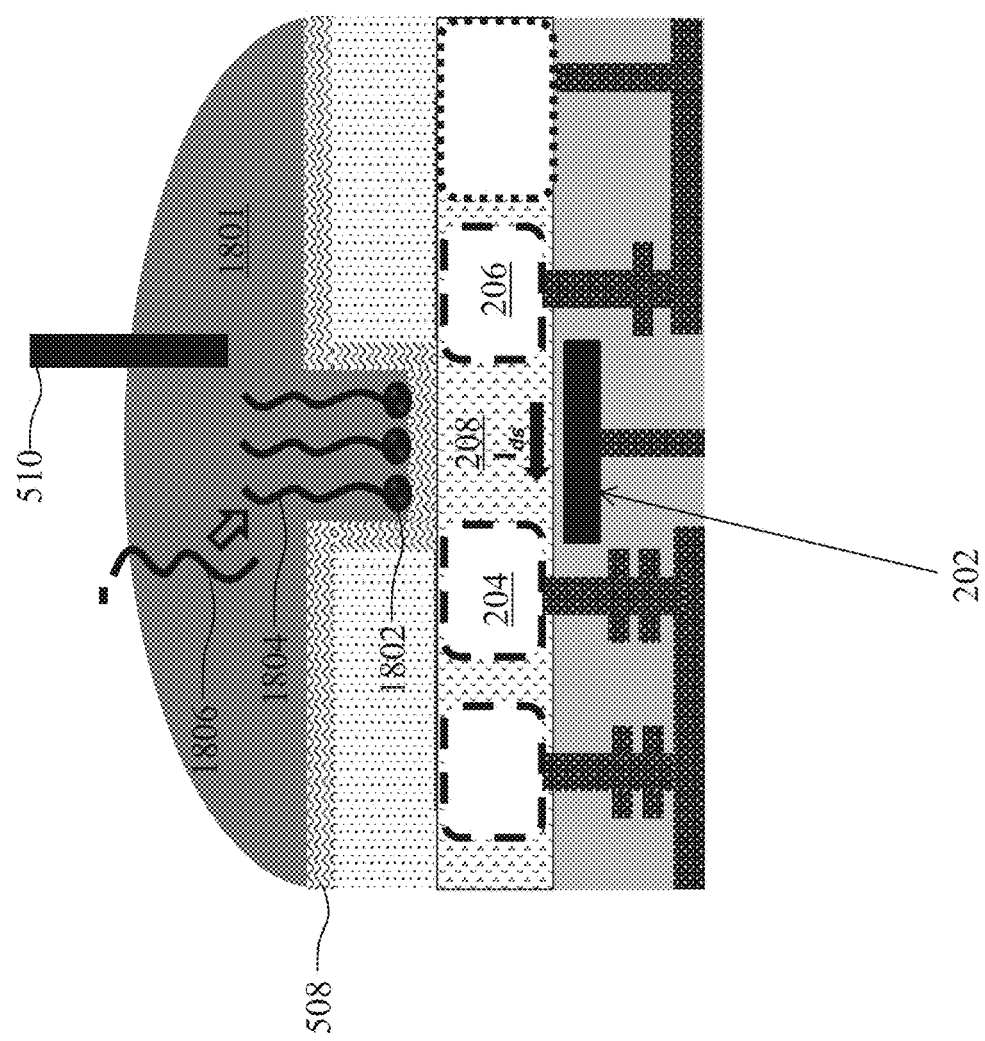
FIG. 18 illustrates a cross-sectional view of an exemplary dual gate back-side sensing bioFET detecting DNA, according to some embodiments.

Referring to FIG. 18, an example biosensing test is performed using a dual gate back-side sensing FET sensor. Probe DNA 1804 (an example of a capture reagent) is bound to interface layer 508 via a linking molecule 1802. Linking molecule 1802 may have a reactive chemical group that binds to a portion of interface layer 508. An example of linking molecules include thiols. Linking molecules may also be formed via silanization of the surface of interface layer 508, or by exposing the surface of interface layer 508 to ammonia ($NH_3$) plasma, to form reactive $NH_3$ groups on the surface. The silanization process involves sequentially exposing the surface of interface layer 508 to different chemicals to build up covalently-bound molecules on the surface of interface layer 508, as would be generally understood by a person skilled in the relevant art. Probe DNA 1804 represents single stranded DNA. The dual gate backside sensing FET sensor illustrated in FIG. 18 may be one bioFET sensor within a sensor array that would exist on a chip.

Probe DNA 1804 may be immobilized on interface layer 508 prior to subjecting the FET sensor to fluid sample 1801. Fluid sample 1801 may include the matching single stranded DNA sequence 1806 that binds strongly to its matching probe DNA 1804. The binding of additional DNA increases the negative charge present on interface layer 508 and directly above channel region 208 of the FET sensor.

Figures 19A, 19B:
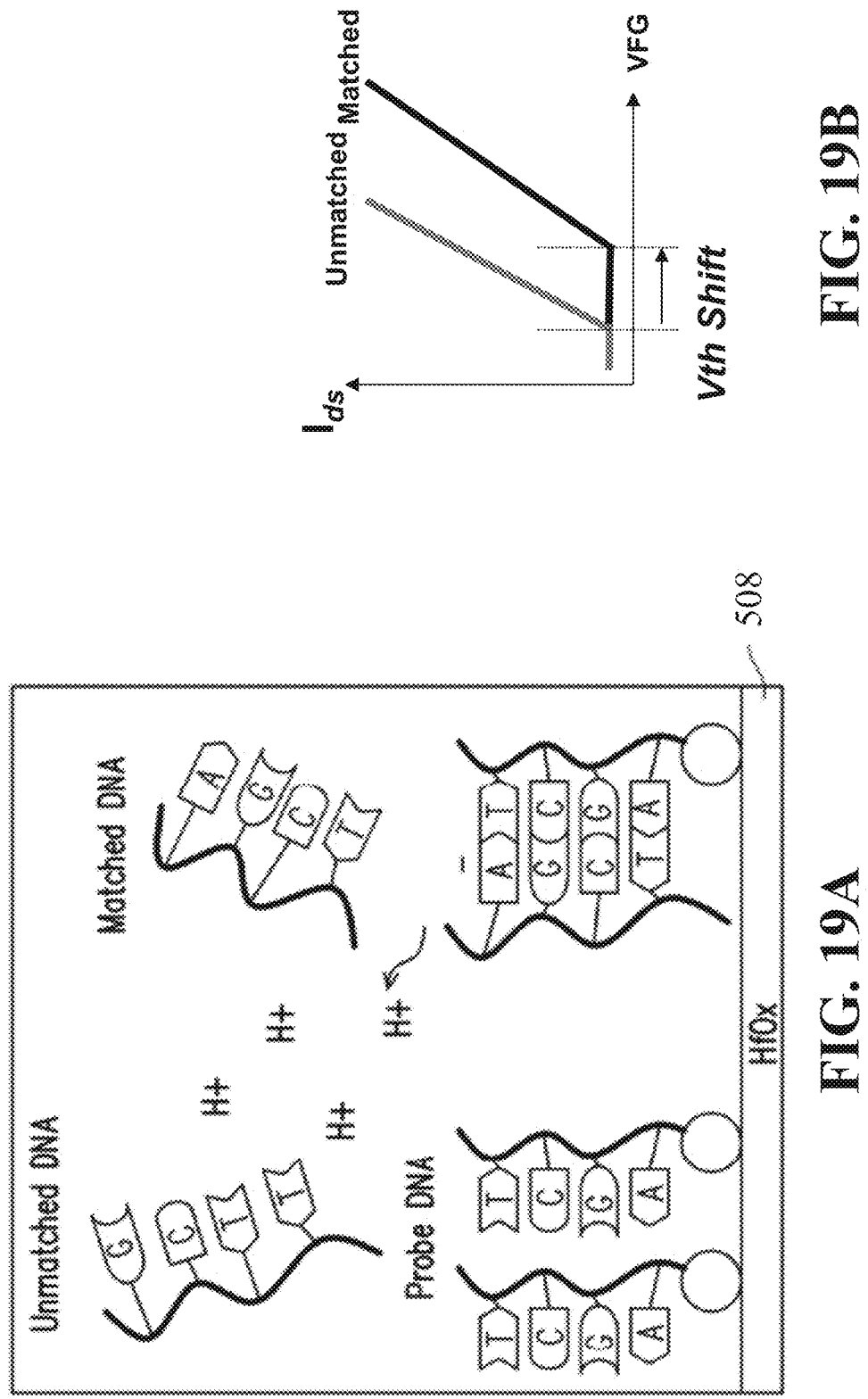
FIG. 19A illustrates binding mechanics of DNA on a receptor surface, according to some embodiments.
FIG. 19B illustrates a change in threshold voltage for an exemplary dual gate back-side sensing bioFET based on matched analyte binding, according to some embodiments.

The DNA binding is illustrated conceptually in FIG. 19A. Here, probe DNA having nucleic acid sequence TOGA binds to its complementary matched strand having nucleic acid sequence AGCT. Any unmatched sequences does not hybridize with the probe DNA sequences. The binding of the matching DNA increases the negative charge built up at the interface of interface layer 508. In the example illustrated in FIG. 19A, interface layer 508 is hafnium oxide.

FIG. 19B illustrates a shift in the threshold voltage of the dual gate back-side sensing FET sensor when matching DNA is bound to the surface of interface layer 508, Briefly, voltage may be applied to fluid gate 510 until the FET sensor "turns on" and current flows between S/D regions 204 and 206. In another example, voltage is applied to gate 202 to turn ON the FET sensor while fluid gate 510 is biased at a given potential. When more negative charge is present at interface layer 508 due to complementary DNA binding, a higher voltage is required to form the conductive inversion layer within channel region 208. Thus, according to some embodiments, a higher voltage may be applied to fluid gate 510, or gate 202, before the FET sensor conducts and $I_{ds}$ current flows. This difference in threshold voltage may be measured and used to determine not only the presence of the target matching DNA sequence, but also its concentration. It should be understood that a net positive accumulated charge at interface layer 508 would cause the threshold voltage to decrease rather than increase. Additionally, the change in threshold voltage will have the opposite sign for an n-channel FET as compared to a p-channel FET.

Figure 20:
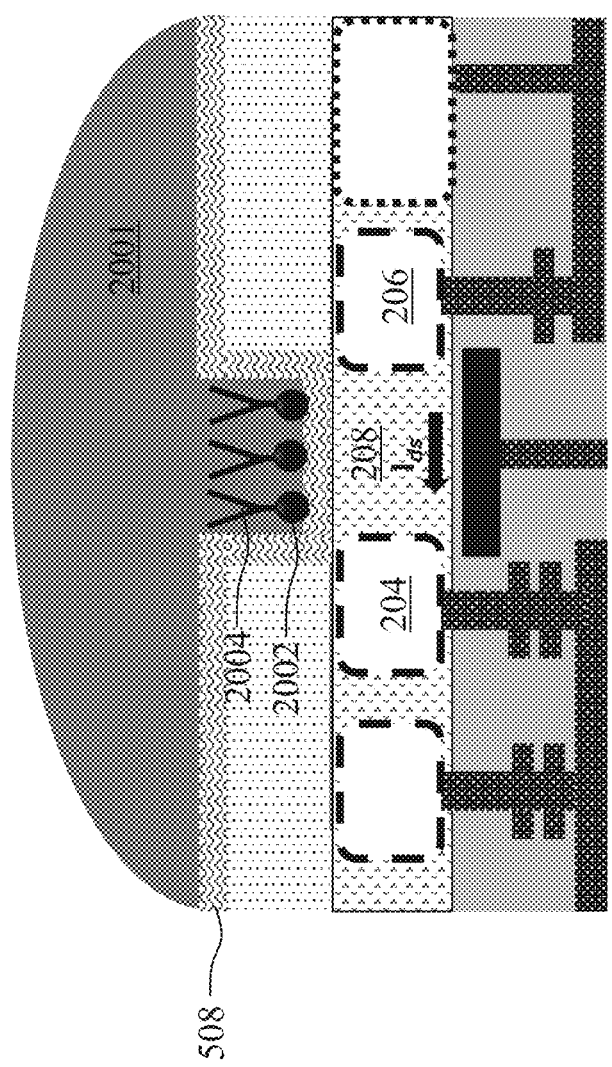
FIG. 20 illustrates a cross-sectional view of an exemplary dual gate back-side sensing bioFET having antibodies immobilized on its sensing layer, according to some embodiments.

Referring to FIG. 20, another example biosensing test is performed using a dual gate back-side FET sensor. Probe antibodies 2004 (another example of capture reagents) are bound to interface layer 508 via linking molecules 2002. Linking molecules 2002 may have a reactive chemical group that binds to a portion of interface layer 508. A sample solution 2001 may be provided over probe antibodies 2004 to determine if the matching antigens are present within sample solution 2001.

Figure 21:
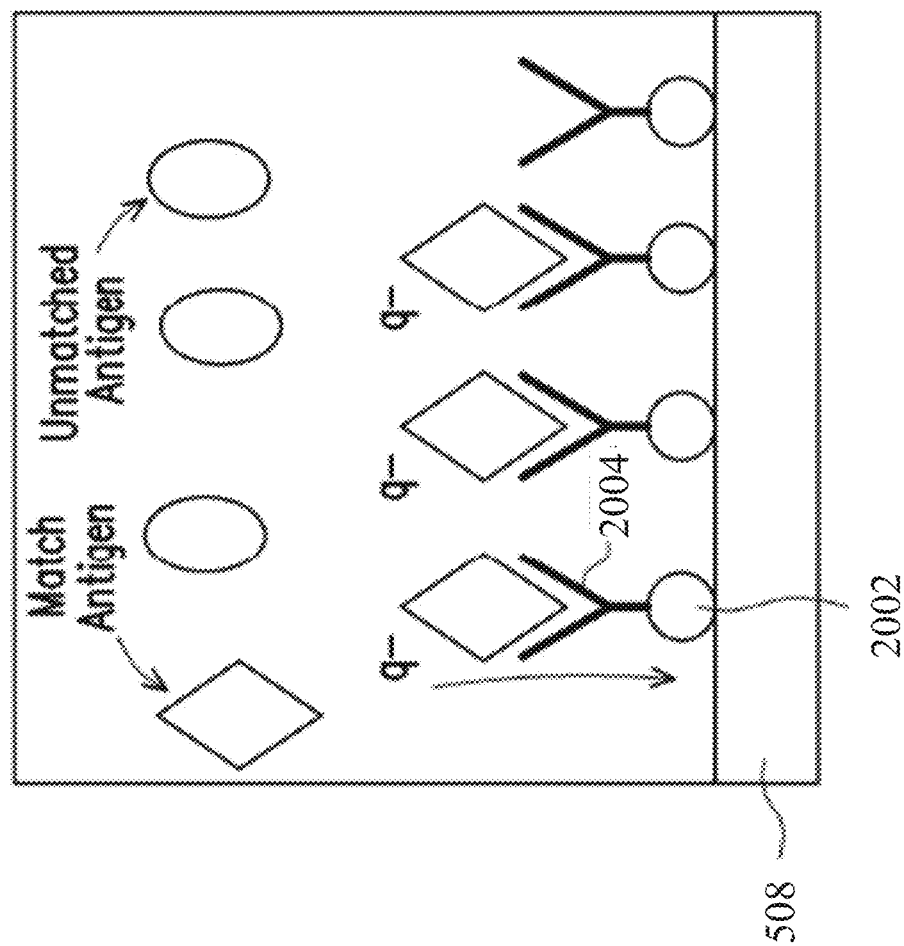
FIG. 21 illustrates binding mechanics of antigens and antibodies on a receptor surface, according to some embodiments.

Referring to FIG. 21, the binding process of matching antigens to probe antibodies 2004 is illustrated. Here, matching antigens will bind to the immobilized probe antibodies 2004 while unmatched antigens will not bind. Similar to the DNA hybridization process described above, the matching antigens will change the accumulated charge present at interface layer 508. The shift in threshold voltage due to the accumulated charge from matching antibodies binding to the probe antibodies is measured in substantially the same way as discussed above with reference to FIG. 19B.

General Biological Applications

BioFETs of the present disclosure may be used to determine the presence or absence of a target analyte. In some aspects, the bioFETs may detect and measure absolute or relative concentrations of one or more target analytes. The bioFETs may also be used to determine static and/or dynamic levels and/or concentrations of one or more target analytes, providing valuable information in connection with biological and chemical processes. The bioFETs may further be used to monitor enzymatic reactions and/or non-enzymatic interactions including, but not limited to, binding. As an example, the bioFETs may be used to monitor enzymatic reactions in which substrates and/or reagents are consumed and/or reaction intermediates, byproducts, and/or products are generated. An example of a reaction that can be monitored using a bioFET of the present disclosure is nucleic acid synthesis to, for example, ascertain nucleic acid sequence.

Types of target analytes for use in the embodiments of the present disclosure may be of any nature provided there exists a capture reagent that binds to it selectively and in some instances specifically. Target analytes may be present in the test sample or, for example, generated following contact of the test sample with the sensing layer of a dual gate back-side sensing bioFET or with other reagents in the solution in contact with the sensing layer of a dual gate back-side sensing bioFET. Thus, types of target analytes include, but are not limited to, hydrogen ions (protons) or other ionic species, non-ionic molecules or compounds, metals, metal coordination compounds, nucleic acids, proteins, lipids, polysaccharides, and small chemical compounds such as sugars, drugs, pharmaceuticals, chemical combinatorial library compounds, and the like. Target analytes may be naturally occurring or may be synthesized in vivo or in vitro. Target analytes may indicate that a reaction or interaction has occurred, or indicate the progression thereof. Target analytes measured by a bioFET according to the present disclosure are not, however, limited and may include any of a variety of biological or chemical substances that provide relevant information regarding a biological or chemical process (e.g., binding events such as nucleic acid hybridization and other nucleic acid interactions, protein-nucleic acid binding, protein-protein binding, antigen-antibody binding, receptor-ligand binding, enzyme-substrate binding, enzyme-inhibitor binding, cell stimulation and/or triggering, interactions of cells or tissues with compounds such as pharmaceutical candidates, and the like). It is to be understood that the present disclosure further contemplates detection of target analytes in the absence of a receptor, for example, detection of PPi and Pi in the absence of PPi or Pi receptors. Any binding or hybridization event that causes a change to the transconductance of the dual gate back-side sensing bioFET changes the current that flows from the drain to the source of the sensors described herein and can be detected according to some embodiments.

For detection of various target analytes, the sensing surfaces of the dual gate back-side sensing bioFETs of the present disclosure may be coated with a capture reagent for the target analyte that binds selectively to the target analyte of interest or in some instances to a genus of analytes to which the target analyte belongs. A capture reagent that binds selectively to a target analyte is a molecule that binds preferentially to that analyte (i.e., its binding affinity for that analyte is greater than its binding affinity for any other analyte). Binding affinities for the analyte of interest may be at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 40-fold, at least about 50-fold, at least about 100-fold, at least about 500-fold, or at least about 1000-fold more than its binding affinity for any other analyte. In addition to relative binding affinity, the capture reagent has an absolute binding affinity that is sufficiently high to efficiently bind the target analyte of interest (i.e., it has a sufficient sensitivity). Capture reagents for use in the methods and systems of the present disclosure may have binding affinities in the femto-molar, picomolar, nanomolar, or micromolar ranges and may be reversible.

The capture reagent may be of any nature (e.g., a chemical, a nucleic acid, a peptide, a lipid, or a combination thereof). The present disclosure contemplates capture reagents that are ionophores, which bind selectively to an ionic species, whether anionic or cationic. In some embodiments, an ionophore is the capture reagent and the ion to which it binds is the target analyte. Ionophores include art-recognized carrier ionophores (i.e., small lipid-soluble molecules that bind to a particular ion) derived from, for example, a microorganism. In some embodiments, the capture reagent is polysiloxane, valinomycin, or salinomycin and the ion to which it binds is potassium. In some embodiments, the capture reagent is monensin, nystatin, or SQI-Pr, and the ion to which it binds is sodium. And in other embodiments, the capture reagent is ionomycin, calcimycine (A23187), or CA 1001 (ETH 1001), and the ion to which it binds is calcium. In other aspects, the present disclosure contemplates capture reagents that bind to more than one ion. For example, beauvericin can be used to detect calcium and/or barium ions, nigericin can be used to detect potassium, hydrogen and/or lead ions, and gramicidin can be used to detect hydrogen, sodium, and/or potassium ions.

Test samples may be from a naturally occurring source or may be non-naturally, occurring. Naturally-occurring test samples include, without limitation, bodily fluids, cells, or tissues to be analyzed for diagnostic, prognostic and/or therapeutic purposes. The test sample may include any of cells, nucleic acids, proteins, sugars, lipids, and the like. In various embodiments, test samples may include chemical or biological libraries to be screened for the presence of agents with particular structural or functional attributes. Samples may be a liquid or dissolved in a liquid and of small volume and, as such, are amenable to high-speed, high-density analysis such as analyte detection using microfluidics.

Examples of bioFETs contemplated by various embodiments discussed herein include, but are not limited to, chemical FETS (chemFETs), ion sensitive FETs (ISFETs), immunologic FETs (ImmunoFETs), genetic FETs (GenFETs or DNA-FETs), enzyme FETs (EnFETs), receptor FETs, cell-based FETs, cell-free FETs, and liquid biopsy FETs. Thus, the bioFETs described herein can be used to detect target analytes with capture reagents and, as such, define the bioFET type that are not mutually exclusive. As a non-limiting example, a liquid biopsy FET may detect cell-free DNA and may also be referred to as a cell-free PET or a DNA-FET. See, e.g., Sakata et al. "Potentiometric Detection of Single Nucleotide Polymorphism by Using a Genetic Field-effect transistor," *Chembiochem* 6 (2005): 703-10; Uslu et al. "Labelfree fully electronic nucleic acid detection system based on a field-effect transistor device," *Biosens Bioelectron* 19 (2004): 1723-31; Sakurai et al. "Real-time monitoring of DNA polymerase reactions by a micro ISFET pH sensor," *Anal Chem* 64.17 (1992): 1996-1997.

For example, some embodiments provide a method for detecting a nucleic acid that includes contacting probe nucleic acids bound to a surface of a back-side sensing layer of a dual gate back-side sensing bioFET with a sample; and detecting binding of a nucleic acid from the sample to one or more regions of the probe nucleic acids. Such a nucleic acid detecting bioFET may also be referred to as a GenFET or DNA-PET.

In other aspects, some embodiments provide a method for detecting a protein that includes contacting probe protein molecules bound to a surface of a back-side sensing layer of a dual gate back-side sensing bioFET with a sample; and detecting binding of a protein from the sample to one or more regions of the probe protein molecules. GenFETs and DNA-FETs may be used to detect the protein.

In other aspects, some embodiments provide a method for detecting a nucleic acid that includes contacting probe protein molecules bound to a surface of a back-side sensing layer of a dual gate back-side sensing bioFET with a sample and detecting binding of a nucleic acid from the sample to one or more regions of the probe protein molecules. In yet other aspects, some embodiments provide a method for detecting an antigen that includes contacting probe antibodies bound to a back-side sensing layer of a dual gate back-side sensing bioFET with a sample and detecting binding of an antigen from the sample to one or more regions of the probe antibodies. Such protein or antibody binding bioFETs may also be referred to as ImmunoFETs.

In other aspects, some embodiments provide a method for detecting an enzyme substrate or inhibitor that includes contacting probe enzymes bound to a surface of a back-side sensing layer of a dual gate back-side sensing bioFET with a sample and detecting binding of an entity from (or generation of an enzymatic product in) the sample to one or more regions of the probe enzymes. In yet other aspects, some embodiments provide a method for detecting an enzyme that includes contacting enzyme substrates or inhibitors bound to a surface of a back-side sensing layer of a dual gate back-side sensing bioFET with a sample and detecting binding of an entity from (or generation of an enzymatic product in) the sample to one or more of the enzyme substrates or inhibitors. Such an enzyme based bioFET may also be referred to as an EnFET.

In other aspects, some embodiments provide a method for detecting protein-small molecule (e.g., organic compound) interactions that includes contacting small molecules bound to a surface of a back-side sensing layer of a dual gate back-side sensing bioFET with a sample and detecting binding of proteins from the sample to one or more regions of the probe small molecules. In yet other aspects, some embodiments provide a method for detecting nucleic acid-small-molecule (e.g., organic compound) interactions that includes contacting small molecules bound to a surface of a back-side sensing layer of a dual gate back-side sensing bioFET with a sample and detecting binding of nucleic acids from the sample to one or more regions of the probe small molecules. In either detection method, the sample may include small molecules and the capture reagents bound to the surface of the back-side sensing layer may be either nucleic acids or proteins. In other aspects, the target analytes of interest are heavy metals and other environmental pollutants, and/or the bioFET arrays are specifically configured to detect the presence of different pollutants. Such small molecule or chemical-sensing bioFETs may also be referred to as chemFETs.

In other aspects, some embodiments provide a method for detecting hydrogen ions and/or changes in H+ concentration (i.e., changes in pH). Such ion-sensing bioFETs may also be referred to as ISFETs.

The systems and methods described herein can also be used to aid in the identification and treatment of disease. For example, some embodiments provide a method for identifying a sequence associated with a particular disease or for identifying a sequence associated with a response to a particular active ingredient or treatment or prophylactic agent that includes contacting a capture reagent (e.g., a nucleic acid probe) bound to a surface of a back-side sensing layer of a dual gate back-side sensing bioFET with a sample, and detecting binding of nucleic acids (e.g., including a variant or lacking nucleic acids otherwise contained in a corresponding wild-type nucleic acid sequence) from the sample to one or more regions of the capture reagent. Such bioFETs may also be referred to as GenFETs, DNA-FETs, or liquid biopsy FETs.

Arrays

The assays and reactions using the bioFETs described herein to detect target analytes can be monitored in an array format to detect, for example, multiple target analytes. In some embodiments, an array of dual gate back-side sensing bioFETs can be configured so that each individual dual gate back-side sensing bioFET of the array is capable of detecting targets in a multiplex format, including, for example, analyte presence (or absence), target analyte levels (or amounts) and/or concentration, or a product of chemical and/or biological processes (e.g., chemical reactions, cell cultures, nucleic acid sequencing processes, etc.). The target analytes may be, for example, a genomic DNA sample, an miRNA or siRNA sample, a cDNA sample from a cell, a tissue or a mass (e.g., a tumor), cell-free DNA obtained from bodily fluid, or a population of cells grown on the array or potentially in a two dimensional array, and may be analyzed for, among other things, type and quantity.

In various embodiments, the array may include multiple biological and/or chemical capture reagents, including, but not limited to, multiple proteins, multiple nucleic acids, or a mixture of proteins and nucleic acids. The multiple biological or chemical capture reagents may be homogenous biological or chemical capture agents. In other embodiments, the multiple biological or chemical capture reagents is not homogeneous. In yet other embodiments, multiple biological or chemical capture reagents is homogeneous in quadrants of the array but not quadrant to quadrant.

The assays and reactions using the bioFETs described herein contemplate the attachment whether covalent or non-covalent and whether direct or indirect of chromosomal nucleic acids, shorter nucleic acids such as oligonucleotides (including oligodeoxyribonucleotides and oligoribonucleotides), nucleic acids such as DNA, RNA, PNA, LNA, or nucleic acids that include any combination and/or level of these various constituents, peptides, proteins including glycoproteins, carbohydrates, oligosaccharides, polysaccharides, and other molecules of interest regardless of nature. Any of these can be applied to the sensing of the dual gate back-side sensing bioFET arrays in a microarray without limiting the binding chemistries.

In various embodiments, the array may be coupled to one or more fluidic structures that form one or more wells or microwells over individual dual gate back-side sensing bioFETs or groups of such bioFETs. In some embodiments, the array can be coupled to an apparatus that delivers samples to, and removes samples from, the wells. In other embodiments, the volume above the dual gate back-side sensing bioFETs is continuous, and thus, the array may be coupled to one or more fluidic structures for the delivery of target analytes or capture reagents and for removal of test samples, capture reagents and/or target analytes. In some embodiments, the continuous flow includes a "closed" system, for example, where the flow of reagents and wash solutions and the like is automated. In some embodiments, the use of multiple flow chambers allows multiple, preferably different, target analytes to be analyzed simultaneously. The arrays may include 2, 3, 4, 5, 6, 7, 8, 9, 10, or more flow chambers. Such configuration applies to a number of dual gate back-side sensing bioFET arrays including, but not limited to, nucleic acid arrays, protein arrays, antibody arrays, enzyme arrays, chemical compound arrays, and the like.

Nucleic Acid Arrays

In various aspects, some embodiments provide for the detection and/or identification of target nucleic acids on oligonucleotide arrays of dual gate back-side sensing bioFETs. In some embodiments, the target nucleic acids are immobilized on the arrays and known capture reagents, substrates, and/or hybridization probes are used to identify the target nucleic acids. In some embodiments, capture reagents are immobilized on the arrays and target nucleic acids are added, for example, to identify the presence of target nucleic acids. Thus, for example, nucleic acids in the form of short nucleic acids e.g., oligonucleotides) or longer nucleic acids (e.g., full length cDNAs) can be provided on the sensing layer of dual gate back-side sensing bioFET arrays described herein.

The nucleic acid arrays described herein contemplate the attachment whether covalent or non-covalent, and whether direct or indirect of target nucleic acids or capture reagents including, but not limited to, chromosomal nucleic acids, shorter nucleic acids such as oligonucleotides (including oligodeoxyribonucleotides and oligoribonucleotides), nucleic acids such as DNA, RNA, PNA, LNA, or nucleic acids that include any combination and/or level of these various components, to the sensing layer of the dual gate back-side sensing bioFETs. Capture reagents may also include, but are not limited to, peptides, proteins including glycoproteins, carbohydrates, oligosaccharides, polysaccharides, and other molecules of interest, so long as they bind to or otherwise aid in the detection of target nucleic acids. In various embodiments, any of these can be applied to the sensing layer of the dual gate back-side sensing bioFET arrays in a manner used for nucleic acid arrays or in any other way without limitation on the binding chemistries.

In embodiments where the nucleic acid arrays use multiple capture reagents of the sort discussed above, such arrays may include identical or non-identical capture reagents and may or may not be heterogeneously dispersed on the array. By way of example, a nucleic acid array may include multiple identical nucleic acid capture reagents, where, for example, more than one dual gate back-side sensing bioFET sensing layer, and optionally the entire sensing surface of the array, has identical nucleic acids conjugated to it. The identical nucleic acids may be uniformly distributed on the array surface or they may be organized into discrete regions (or cells) on that surface. Alternatively, the nucleic acid arrays may include multiple non-identical nucleic acid capture reagents. Such arrays may then include non-identical nucleic acids heterogeneously dispersed on the surface of the array, or the multiple non-identical nucleic acids may be organized into discrete regions (or cells) on the surface of the array where, for example, identical nucleic acids are distributed in one discrete region, another discrete region contains different non-identical nucleic acids, and so forth, such that the array includes multiple non-identical nucleic acids dispersed into discrete regions of identical nucleic acids.

The capture reagents may vary depending on any number of factors including, but not limited to, target nucleic acid type, sequence, modification, target nucleic acid length, or method used to attach the capture reagent to the sensing layer of the dual gate back-side sensing bioFET. For example, the array may have any number of discrete regions including, but not limited to, at least 10, $10^2$, $10^3$, $10^4$, $10^5$, $10^6$, $10^7$, or more, including capture reagents. The capture reagents may be distributed or attached to the array such that multiple target nucleic acids including, but not limited to, at least 10, 50, 100, 500, $10^3$, $10^4$, $10^5$, $10^6$, or more nucleic acids are captured. Where, for example, nucleic acids are used as capture reagents, the multiple nucleic acid capture reagents have a length of less than 100 bases in length (including about 10, 15, 20, 25, 30; 40, 50, 60, 70, 80, or 90 bases in length), or the multiple nucleic acid capture reagents have an average length of less than 100 bases in length (including about 10, 15, 20, 25, 30, 40, 50, 60, 70, 80, or 90 bases in length). In some embodiments, the nucleic acid capture reagent is, or the multiple nucleic acid capture reagents are, single stranded. In other embodiments, the nucleic acid capture reagent is, or the multiple nucleic acid capture reagents are, double stranded. [Remark: How can the nucleic acid capture reagent be double-standed? Does it have other functional groups that can capture things?] Where, for example, the capture reagents are proteins, such as antibodies for example; or any other capture reagents described herein, the capture reagents may be similarly optimized to detect the target nucleic acids. See, e.g., U.S. Pat. No. 8,349,167 (Col. 17, lines 1-54).

Methods for attaching capture reagents, including nucleic acids, proteins, molecules, and the like, to solid supports, particularly in the context of an array, have been discussed elsewhere, including in Lipshutz et al., "High density synthetic oligonucleotide arrays." *Nat. Genet.* (supplement) 21 (1999): 20-24; Li, Cheng, and Wing Hung Wong, "Model-based analysis of oligonucleotide arrays: expression index computation and outlier detection." *Proceedings of the National Academy of Sciences* 98.1 (2001): 31-6; Lockhart, David J., et al., "Expression monitoring by hybridization to high-density oligonucleotide arrays." *Nature Biotechnology* 14.13 (1996): 1675-1680; Wodicka, Lisa, et al., "Genome-wide expression monitoring in *Saccharomyces cerevisiae.*" *Nature Biotechnology* 15.13 (1997): 1359-1367; Chen, Yidong, Edward R. Dougherty, and Michael L. Bittner, "Ratio-based decisions and the quantitative analysis of cDNA microarray images," *Journal of Biomedical Optics* 2.4 (1997): 364-374; Duggan, David J., et al., "Expression profiling using cDNA microarrays." *Nature Genetics* 21 (1999) Page 10-12; Marton, Matthew J., et al., "Drug target validation and identification of secondary drug target effects using DNA microarrays." *Nature Medicine* 4.11 (1998): 1293-1301; Kononen, Juha, et al., "Tissue microarrays for high-throughput molecular profiling of tumor specimens." *Nature Medicine* 4.7 (1998): 844-847; MacBeath, Gavin, and Stuart L. Schreiber, "Printing proteins as microarrays for high-throughput function determination." *Science* 289.5485 (2000): 1760-1763; Haab, Brian B., Maitreya J. Dunham, and Patrick O. Brown, "Protein microarrays for highly parallel detection and quantitation of specific proteins and antibodies in complex solutions." *Genome Biology* 2.2 (2001): research0004-1; Pollack, Jonathan R., et al., "Genome-wide analysis of DNA copy-number changes using cDNA microarrays." *Nature Genetics* 23.1 (1999): 41-46; Wang, David G., et al., "Large-scale identification, mapping, and genotyping of single-nucleotide polymorphisms in the human genome." *Science* 280.5366 (1998): 1077-1082; Fodor, Stephen P A, et al., "Light-directed, spatially addressable parallel chemical synthesis." *Science* 251 (1991): 767-773; Fodor, Stephen, et al., "Multiplexed biochemical assays with biological chips." *Nature* 364 (1993): 555-556; Pease, Ann Caviani, et al., "Light-generated oligonucleotide arrays for rapid DNA sequence analysis," *Proceedings of the National Academy of Sciences* 91.11 (1994): 5022-5026; Fodor, Stephen P A., "Massively parallel genomics." *Science* 277.5324 (1997): 393-95; Southern, E. M., U. Maskos, and J. K. Elder, "Analyzing and comparing nucleic acid sequences by hybridization to arrays of oligonucleotides: evaluation using experimental models." *Genomics* 13.4 (1992): 1008-1017; Schena, Mark, et al., "Quantitative monitoring of gene expression patterns with a complementary DNA microarray." *Science* 270 (1995): 467-470; Shalon, Dari, Stephen J. Smith, and Patrick O. Brown, "A DNA microarray system for analyzing complex DNA samples using two-color fluorescent probe hybridization." *Genome Research* 6.7 (1996): 639-645; Jongsma, Maarten A., and Ralph H G M Litjens, "Self-assembling protein arrays on DNA chips by auto-labeling fusion proteins with a single DNA address." *Proteomics* 6.9 (2006): 2650-2655; Sakata, Toshiya, and Yuji Miyahara, "Direct transduction of allele-specific primer extension into electrical signal using genetic field effect transistor." *Biosensors and Bioelectronics* 22.7 (2007): 1311-1316. And any of the binding chemistries used to generate microarrays on substrates, such as glass, plastic, nylon, nitrocellulose and activated gels, may be used to immobilize nucleic acids on the sensing layer of the dual gate back-side sensing bioFET array. See, e.g. Zammatteo, Nathalie, et al., "Comparison between different strategies of covalent attachment of DNA to glass surfaces to build DNA microarrays." *Analytical Biochemistry* 280.1 (2000): 143-150. Several non-limiting examples are discussed below.

The nucleic acid capture reagents may be immobilized or attached covalently or non-covalently (e.g., ionic) on the sensing layer of dual gate back-side sensing bioFETs. Covalent attachment may be direct or indirect (e.g., through a linker, such as a bifunctional linker). In the context of nucleic acid arrays, ionic binding can employ the interaction of negatively charged species, such as DNA, with a positively charged surface, such as glass slides coated with poly-lysine. See Schena, Mark, et al., "Quantitative monitoring of gene expression patterns with a complementary DNA microarray." *Science* 270 (1995): 467-470. Hydrophobic interactions have also been used to attach nucleic acids to various surfaces. See Allemand, J. F., Bensimon, D., Jullien, L., Bensimon, A., & Croquette, V., "pH-dependent specific binding and combing of DNA." *Biophysical Journal* 73(4) (1997): 2064-2070. Similar non-covalent attachment strategies may be used to immobilize or attach nucleic acid capture reagents to the sensing layer of dual gate back-side sensing bioFETs.

In addition, non-covalent immobilization or attachment of nucleic acid capture reagents may be achieved through non-covalent deposition of the capture reagent onto the surface, involving, for example, the use of a polymer matrix or similar technology. The polymer may be naturally occurring or non-naturally occurring. The capture reagent may be adsorbed onto and/or entrapped within the polymer matrix. The nature of the polymer will depend on the nature of the capture reagent used and/or target analyte detected. Examples of polymers that can be used can be found in U.S. Pat. No. 7,948,015 (Col. 33, lines 34-67), U.S. Pat. No. 6,063,637 (Col. 15, lines 11-26), and U.S. Pub. Appl. No. 2010/0137143 (Paragraphs [0375], [0377]). Polymer matrices may also be used for covalent deposition of the nucleic acid capture reagents. In some embodiments, the nucleic acid capture reagent may be covalently conjugated or cross-linked to the polymer (e.g., "grafted" onto a functionalized polymer).

Covalent binding of nucleic acid capture reagents, for example, may be achieved through a variety of methods. UV radiation may be used to cross-link nucleic acids (such as DNA) to amino group containing substances, for example, by forming covalent bonds between positively charged amino groups and thymidine residues present along the length of the nucleic acid strand. See, e.g., Duggan et al. "Expression profiling using cDNA microarrays,". *Nature Genetics* 21, 10-14 (1999). Additionally, dendrimeric linker molecules as a substrate for covalent attachment of Peptide Nucleic Acids (PNAs), PCR products or oligonucleotides, to glass or polypropylene supports may also be used. See, e.g., Beier, Markus, and Jorg D. Hoheisel, "Versatile derivatisation of solid support media for covalent bonding on DNA-microchips." *Nucleic Acids Research* 27.9 (1999): 1970-1977.

In further embodiments, nucleic acid capture reagents may be attached to the solid support by their 5' or 3' ends, particularly where such ends are carboxylated or phosphorylated. See, e.g., Joos et al., "Covalent attachment of hybridizable oligonucleotides to glass supports," *Anal Biochem* 247 (1997): 96-101. Such nucleic acid capture reagents can be coupled on aminated supports, or the nucleic acids themselves may be aminated and then attached to carboxylated, phosphorylated, epoxide-modified, isothiocyanate-activated, or aldehyde-activated supports or surfaces. See, e.g., Ghosh et al., "Covalent attachment of oligonucleotides to solid supports," *Nucl. Acids Res.* 15 (1987): 5353-5372; Lamture et al. "Direct detection of nucleic acid hybridization on the surface of a charge coupled device," *Nucleic Acids Res.* 22 (1994): 2121-2125; Guo et al., "Direct fluorescence analysis of genetic polymorphisms by hybridization with oligonucleotide arrays on glass supports." *Nucleic Acids Res.* 22 (1994): 5456-5465; Schena et al., "Parallel human genome analysis: microarray-based expression monitoring of 1000 genes," *PNAS* 93 (1996): 10614-10619. By way of example, nucleic acids may be synthesized with reaction groups such as amine or thiol groups to provide a point of attachment for a bifunctional linker or nucleic acids may be synthesized by incorporating conjugation-competent reagents such as Uni-Link Amino-Modifier, 5-DMS(O)MT-Amino-Modifier-C6, 5-Amino-Modifier-C3-TFA, 5-Amino-Modifier-C12, 5-Amino-Modifier-C6-TFA, 5'-Amino-dT, 5'-Amino-Modifier-5; Amino-Modifier-C2-dT, Amino-Modifier-C6-dT, 3'-Amino-Modifier-C7-CPG, 5'-Thiol-Modifier C6 S-S. 3'-Thiol-Modifier-C3 S-S.

A bifunctional linker is a compound having at least two reactive groups to which two entities may be bound. In some embodiments, the reactive groups are located at opposite ends of the bifunctional linker. In some embodiments, the bifunctional linker is a universal bifunctional linker, which is a linker that can be used to link a variety of entities. Examples of bifunctional linkers include those discussed in U.S. Pub. Appl. No. 2010/0282617 A1 (Paragraph [0249], [0250]).

The bifunctional linker may be a homo-bifunctional linker or a hetero-bifunctional linker, depending upon the nature of the molecules to be conjugated. Homo-bifunctional linkers have two identical reactive groups. Hetero-bifunctional linkers have two different reactive groups. Various types of linkers are reactive with one or more of the following groups: primary amines, secondary amines, sulfhydryls, carboxyls, carbonyls, and carbohydrates. Non-limiting examples of such linkers can be found in U.S. Pat. No. 7,948,015 (Col. 32, lines 58-67, Col. 33, lines 1-17); U.S. Pub. Appl. No. 2010/0137143 (Paragraphs [0373]-[0374]); Boncheva et al., "Design of Oligonucleotide Arrays at Interfaces," *Langmuir* 15 (1999): 4317-4320 (thiol- or disulfide-modified oligonucleotides attachment to gold); Chrisey et al, "Covalent attachment of synthetic DNA to self-assembled monolayer films," *Nucl. Acids Res.* 24.15 (1996): 3031-3039 (attachment to aminosilane-modified glass surfaces); Rogers et al., "Immobilization of oligonucleotides onto a glass support via disulfide bonds: A method for preparation of DNA microarrays," *Analytical Biochemistry* 266 (1999): 23-30 (3-mercaptopropylsilane-modified glass surfaces).

In addition to, or in combination with, the attachment of preformed nucleic acids to the sensing layers of dual gate back-side sensing bioFETs in arrays, the present disclosure includes synthesis of nucleic acids onto the sensing layers (e.g., in situ synthesis). A non-comprehensive list of examples includes in situ synthesis via ink-jet printing delivery of phosphoramidites (Blanchard et al., "High-density oligonucleotide arrays," *Biosensors and Bioelectronics* 11 (1996): 687-690); parallel synthesis (Egeland, Ryan D., and Edwin M. Southern, "Electrochemically directed synthesis of oligonucleotides for DNA microarray fabrication," *Nucleic Acids Research* 33.14 (2005): e125-e125); maskless photo-generated acid (PGA) controlled synthesis (LeProust et al., "Digital light-directed synthesis. A microarray platform that permits rapid reaction optimization on a combinatorial basis," *J Comb Chem* 2.4 (2000): 349-354; Gao et al., "A flexible light-directed DNA chip synthesis gated by deprotection using solution photogenerated acids," *Nucleic Acids Res* 29 (2001): 4744-4750); mask directed synthesis utilizing photolithography (PLPG) (Fodor et al., "Light-directed, spatially addressable parallel chemical synthesis,"

*Science* 251 (1991): 767-773); and maskless PLPG parallel in situ synthesis (Singh-Gasson et al., "Maskless fabrication of light-directed oligonucleotide microarrays using a digital micromirror array," *Nat Biotechnol* 17 (1999): 974-78). See also Nuwaysir, Emile F., et al., "Gene expression analysis using oligonucleotide arrays produced by maskless photo-lithography." *Genome Research* 12.11 (2002): 1749-1755.

Additional methods to attach or immobilize target nucleic acids or capture reagents to an array include spotting onto a surface by piezoelectrical deposition; UV cross-linking of nucleic acids to polymer layers such as, but not limited to, poly-L-lysine or polypyrrole; direct conjugation to silicon coated $SiO_2$ (U.S. Pub. Appl. No. 2003/0186262 (Paragraphs [0026], [0045], [0055], [0083]); direct conjugation to a silanised bioFET surface (e.g., a surface treated with 3-aminopropyltriethoxysilane (APTES) (Uslu, F., et al, "Labelfree fully electronic nucleic acid detection system based on a field-effect transistor device." *Biosensors and Bioelectronics* 19.12 (2004): 1723-1731)). See also Pease, Ann Caviani, et al., "Light-generated oligonucleotide arrays for rapid DNA sequence analysis." *Proceedings of the National Academy of Sciences* 91.11 (1994): 5022-5026. By way of further example, several non-limiting approaches to attach or immobilize target nucleic acids or capture reagents to an array include but are not limited to mechanical spotting (for example pin-type spotters), piezo or print-head printing (including ink jet or drop-on-demand), or in situ synthesis or application through attachment from a solution, such as limiting dilution or dipping. These techniques may be compatible with application to the dual gate back-side sensing bioFET sensing layer for the bioFETs described herein.

Binding or hybridization of the target nucleic acids to the capture reagents, for example, nucleic acids, is performed, for example, under stringent hybridization conditions, moderate stringency hybridization conditions, or under high stringency hybridization conditions. Calculations regarding hybridization conditions for attaining particular degrees of stringency are discussed in, e.g., Sambrook, Joseph, Edward F. Fritsch, and Tom Maniatis, *Molecular Cloning: A Laboratory Manual*. $4^{th}$ Ed. Cold Spring Harbor Laboratory Press (2012.) Vol. 1, Ch. 2, 6, 10; Nucleic Acid Hybridization—A Practical Approach, Eds. Hames, B. D. and Higgins, S. J., IRL Press, 1985; Ausubel, F. M., et al, "Current Protocols in Molecular Biology" John Wiley & Sons, Inc. (2017) Units 19.6, 21.25, and U.S. Pat. No. 8,357,488 (Col. 9, lines 36-45). Example hybridization stringency conditions include (in order of increasing stringency), but are not limited to, the following: incubation temperatures of 25° C., 37° C., 50° C., and 68° C.; buffer concentrations of 10×SSC, 6×SSC, 4×SSC, 1× SSC, 0.1×SSC (where SSC (Saline Sodium Citrate) is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water.

It is to be understood that, like the protein arrays contemplated herein, the readout from the nucleic acid arrays may be a change in current through the bioFET and thus no additional step of labeling and/or label detection is required in these array methods, although labeling and/or label detection may be used in the apparatus, systems, and methods described herein.

Protein Arrays

In various aspects, some embodiments provide for the detection and/or identification of target proteins on protein arrays of dual gate back-side sensing bioFETs. In some embodiments, the target proteins are immobilized on the arrays and known capture reagents are used to identify the target proteins. In some embodiments, capture reagents are immobilized on the arrays and target proteins are added, for example, to identify the presence of target proteins. Thus, for example, proteins in the form of proteins, peptides, or other amino acid including biological moiety can be provided on the sensing layer of dual gate back-side sensing bioFET arrays described herein.

The protein arrays described herein contemplate the attachment, whether covalent or non-covalent, and whether direct or indirect, of target proteins or capture reagents including, but not limited to, enzymes, antibodies and antibody fragments or antibody mimics (e.g., single chain antibodies) to the sensing layer of the dual gate back-side sensing bioFETs. Capture reagents may also include, but are not limited to, nucleic acids, peptides, proteins including glycoproteins, carbohydrates, oligosaccharides, polysaccharides, and other molecules of interest, so long as they bind to or otherwise aid in the detection of target proteins. In various embodiments, any of these can be applied to the sensing layer of the dual gate back-side sensing bioFET arrays in a manner used for protein arrays or in any other way without limitation on the binding chemistries.

In embodiments where the protein arrays use multiple capture reagents of the sort discussed above, such arrays may include identical or non-identical capture reagents and may or may not be heterogeneously dispersed on the array. By way of example, a protein array may include multiple identical protein capture reagents, where, for example, more than one dual gate back-side sensing bioFET sensing layer, and optionally the entire sensing surface of the array, has identical proteins conjugated to it. The identical proteins may be uniformly distributed on the array surface or they may be organized into discrete regions (or cells) on that surface. Alternatively, the protein arrays may include multiple non-identical protein capture reagents. Such arrays may then include non-identical proteins heterogeneously dispersed on the surface of the array, or multiple non-identical proteins may be organized into discrete regions (or cells) on the surface of the array where, for example, identical proteins are distributed in one discrete region, another discrete region contains a different non-identical proteins, and so forth, such that the array includes multiple non-identical proteins dispersed into discrete regions of identical proteins.

The multiple capture reagents may vary depending on any number of factors including, but not limited to, target protein type, sequence, modification, target protein length, or method used to attach the capture reagent to the sensing layer of the dual gate back-side sensing bioFET. For example, the array may have any number of discrete regions including, but not limited to, at least 10, $10^2$, $10^3$, $10^4$, $10^5$, $10^6$; $10^7$, or more, including capture reagents. The capture reagents may be distributed or attached to the array such that multiple target proteins including, but not limited to, at least 10, 50, 100, 500, $10^3$; $10^1$, $10^5$; $10^6$ or more proteins are captured. Where, for example, proteins are used as capture reagents, such as antibodies for example, or any other capture reagents described herein, the capture reagents may be similarly optimized to detect the target proteins, See, e.g., U.S. Pat. No. 8,349,167 (Col. 99, line 45-67; Col. 100, line 1-3). Methods for attaching capture reagents, including nucleic acids, proteins, molecules, and the like, to solid supports, particularly in the context of an array, have been described above with respect to nucleic acid arrays. Additional references related to protein arrays include: Zhu, Heng, and Michael Snyder; "Protein arrays and microarrays." *Curr Opin Chem Biol* 5.1 (2001): 40-45; Schweitzer et al., "Measuring proteins on microarrays," *Curr Orrin Biotechnol* 13 (2002): 14-19; Schweitzer et al., "Multiplexed protein profiling on microarrays by rolling-circle amplification," *Nat Biotechnol* 20 (2002), 359-365; Eppinger et al., "Enzyme microarrays: On-chip determination of inhibition constants based on affinity-label detection of enzymatic activity," *Angew Chem Int Ed Engl* 43 (2004): 3806-3810; Funeriu et al., "Enzyme family-specific and activity-based screening of chemical libraries using enzyme microarrays," *Nat Biotechnol* 23 (2005): 622-7; Schweitzer, Barry, et al., "Immunoassays with rolling circle DNA amplification: a versatile platform for ultrasensitive antigen detection." *Proceedings of National Academy of Sciences* 97.18 (2000): 10113-10119, 10114-10116; Gao, Xiaolian, et al., "High density peptide microarrays. In situ synthesis and applications." *Molecular Diversity* 8.3 (2004): 177-187.

The protein capture reagents may be immobilized or attached covalently or non-covalently ionic) on the sensing layer of dual gate back-side sensing bioFETs. Many techniques for immobilizing or attaching protein capture reagents on the sensing layer of dual gate back-side sensing bioFETs are similar to those described above for nucleic acid capture reagents. For example, covalent and non-covalent (e.g., ionic, including a streptavidin-biotin interaction) attachment of peptides, proteins, antibodies, or fragments thereof to the sensing layer of dual gate back-side sensing bioFETs may be performed using an applied solution, direct printing of peptides or proteins; self-assembly of peptides or proteins on the array using for example oligonucleotide tags, immobilization of high affinity nucleic acid aptamers, and various methods of in situ peptide synthesis. See, e.g., U.S. Pat. No. 8,349,167 (Col. 100, lines 38-67; Col. 101, lines 1-16); Li et al., *Science in China Series B: Chemistry* 51 (2008): 193-204 (aptamers have been shown to be successful sensors when coupled to individual ISFETs); see also U.S. Pat. No. 9,329,173 B2 (Col. 7, lines 24-46; Col. 9, lines 27-61).

Where the protein capture reagent includes antibodies, a species specific antibody (e.g., anti-mouse, anti-rabbit, anti-goat, anti-guinea pig, anti-rat, anti-llama, anti-camel) may be used and immobilized onto the sensing layer of dual gate back-side sensing bioFETs. Antigen-specific polyclonal and monoclonal primary antibodies raised in, for example, mouse, rabbit, goat, guinea pig, rat, llama, or camel, may be added and recognized by the secondary antibody immobilized to the sensor surface or other surface. To stabilize the interaction, chemical bifunctional cross linkers may be used to irreversibly connect both antibodies. See; e.g., U.S. Pub. Appl. Nos. 2016/0041157; 2016/0184477 (Paragraphs [0238], [0248], [0249], [0250], [0251], [0252]); 2013/0178587 (Paragraph [0003]); U.S. Pat. No. 4,676,980 (Col. 1, lines 45-68); Brennan, Maureen, Peter F, Davison, and Henry Paulus, "Preparation of bispecific antibodies by chemical recombination of monoclonal immunoglobulin G1 fragments." *Science* 229 (1985): 81-84.

In addition to, or in combination with, the attachment of preformed proteins to the sensing layers of dual gate back-side sensing bioFETs in arrays, the present disclosure includes synthesis of proteins onto the sensing layers (e.g., in situ synthesis), as discussed above for nucleic acid arrays. For example, proteins may be synthesized using cell-free DNA expression or chemical synthesis. See, e.g., MacBeath, Gavin, and Stuart L. Schreiber, "Printing proteins as microarrays for high-throughput function determination." *Science* 289.5485 (2000): 1760-1763; Todd, John A., et al., "Robust associations of four new chromosome regions from genome-wide analyses of type 1 diabetes." *Nature Genetics* 39.7 (2007): 857-864; U.S. Pat. No. 6,919,211 (Col. 62, lines 53-65); U.S. Pub. Appl. No. 2003/0113835 (Paragraphs [0003], [0007], [0008], [0013]).

It is to be understood that, like the nucleic acid arrays contemplated herein, the readout from the protein arrays may be a change in current through the bioFET and thus no additional step of labeling and/or label detection is required in these array methods, although labeling and/or label detection may be used in the apparatus, systems, and methods described herein. See, e.g., Schasfoort, Richardus B M, et al., "Modulation of the ISFET response by an immunological reaction." *Sensors and Actuators* 17.3-4 (1989): 531-535; "Modulation of the ISFET response by an immunological reaction," *Sens. Actuators* 17, 531-535 (1989); Schasfoort Richardus B M, et al., "Possibilities and limitations of direct detection of protein charges by means of an immunological field-effect transistor," *Analytica Chimica Acta* 238 (1990): 323-329; Besselink, G. A. J., Richardus B M Schasfoort, and Piet Bergveld, "Modification of ISFETs with a monolayer of latex beads for specific detection of proteins." *Biosensors and Bioelectronics* 18.9 (2003): 1109-1114.

Chemical Compound Arrays in various aspects, some embodiments provide for the detection and/or identification of target chemical compounds on chemical compound arrays of dual gate back-side sensing bioFETs. In some embodiments, the target chemical compounds are immobilized on the arrays and known capture reagents are used to identify the target chemical compounds. In some embodiments, capture reagents are immobilized on the arrays and target chemical compounds are added, for example, to identify the presence of target chemical compounds. Thus, for example, chemical compounds in any form can be provided on the sensing layer of dual gate back-side sensing bio ET arrays described herein.

The chemical compound arrays described herein include the attachment, whether covalent or non-covalent, and whether direct or indirect, of target chemical compounds or capture reagents, to the sensing layer of the dual gate back-side sensing bioFETs. Capture reagents may also include, but are not limited to, nucleic acids, shorter nucleic acids such as oligonucleotides (including oligodeoxyribonucleotides and oligoribonucleotides), DNA, RNA, PNA, LNA, or nucleic acids that include any combination and/or level of these various components, peptides, proteins including glycoproteins, carbohydrates, oligosaccharides, polysaccharides, and other molecules of interest, so long as they bind to or otherwise aid in the detection of target chemical compounds. In various embodiments, any of these can be applied to the sensing layer of the dual gate back-side sensing bioFET arrays in a manner used for chemical compound arrays or in any other way without limitation on the binding chemistries.

In embodiments where the chemical compound arrays use multiple capture reagents of the sort discussed above, such arrays may include identical or non-identical capture reagents and may or may not be heterogeneously dispersed on the array. By way of example, a chemical compound array may include multiple identical capture reagents, where, for example, more than one dual gate back-side sensing bioFET sensing layer, and optionally the entire sensing surface of the array, has identical capture reagents conjugated to it. The identical capture reagents may be uniformly distributed on the array surface or they may be organized into discrete regions (or cells) on that surface. Alternatively, the chemical compound arrays may include multiple non-identical capture reagents. Such arrays may then include non-identical capture reagents heterogeneously dispersed on the surface of the array, or multiple non-identical capture reagents may be organized into discrete regions (or cells) on the surface of the array where, for example, identical capture reagents are distributed in one discrete region, another discrete region contains different non-identical capture reagents, and so forth, such that the array includes multiple non-identical capture reagents dispersed into discrete regions of identical capture reagents.

The multiple capture reagents may vary depending on any number of factors including, but not limited to, target chemical compound type, modification, size, or method used to attach the capture reagent to the sensing layer of the dual gate back-side sensing bioFET. For example, the array may have any number of discrete regions including, but not limited to, at least 10, $10^2$, $10^3$, $10^4$, $10^5$, $10^6$, $10^7$, or more, including capture reagents. The capture reagents may be distributed or attached to the array such that multiple target chemical compounds including, but not limited to, at least 10, 50, 100, 500, $10^3$, $10^4$, $10^5$, $10^6$ or more chemical compounds that are captured. Where, for example, the capture reagents are for nucleic acid and protein arrays (as discussed above), in which the capture reagents may be similarly optimized to detect the target chemical compounds. See, U.S. Pat. No. 8,349,167 (Col. 13).

Methods for immobilizing or attaching capture reagents, including nucleic acids, proteins, molecules, and the like, to solid supports, particularly in the context of an array, are discussed above in reference to the nucleic acid and protein arrays. Chemical compound arrays may be made using similar immobilization and attachment strategies. For example; chemical compound capture reagents may be immobilized or attached covalently or non-covalently (e.g., ionic) on the sensing layer of dual gate back-side sensing bioFETs. Covalent attachment may be direct or indirect (e.g., through a linker, such as a bifunctional linker). Examples of chemical compound array immobilization or attachment strategies and formats include those described in, for example, U.S. Pub. Appl. Nos. 2003/0032203 (small molecule microarray; Paragraph [0093]); 2004/0171053 (small molecule microarray; Paragraphs [0036]-[0047]); Singh, V., et al., "Small molecule microarray screening methodology based on surface plasmon resonance imaging," Arabian J. Chem. (2015); Freiberg, Gail, et al., "Utilization of microarrayed compound screening (μARCS) to identify inhibitors of p56lck tyrosine kinase." *Journal of Biomolecular Screening* 9.1 (2004): 12-21; Uttamchandani, Mahesh, et al., "Small molecule microarrays: recent advances and applications." *Curr Opin Chemical Biology* 9.1 (2005): 4-13; Walsh, D, P., and Y. T. Chang, "Recent advances in small molecule microarrays: applications and technology." Combinatorial Chemistry & High Throughput Screening 7.6 (2004): 557-564; Ma, Haiching, and Kurumi Y. Horiuchi, "Chemical microarray: a new tool for drug screening and discovery." *Drug Discovery Today* 11.13 (2006): 661-668.

The chemical compound arrays described herein may facilitate the detection of binding and/or activation events between the array compounds and biological macromolecules. Thus, the present disclosure includes methods for identifying small molecule partners for biological macromolecules of interest. The small molecule partners may be compounds that bind to particular macromolecules of interest and are capable of activating or inhibiting the biological macromolecules of interest. If the chemical compound array includes one or more different types of compounds, a method for encoding each of the specific compounds may be used such that a compound having a specific interaction can be identified. Specific encoding techniques, as well as other equivalent or improved techniques, include those described in Czarnik, Anthony W., "Encoding methods for combinatorial chemistry." *Curr Opin Chem Biol* 1.1 (1997): 60-66. Alternatively, where the array includes one type of chemical compound, a library of biological macromolecules may be contacted with this array to determine the ability of the chemical compound to interact with a variety of biological macromolecules.

Nucleic Acid Sequencing

In various aspects, some embodiments for sequencing of target analytes includes nucleic acids using dual gate back-side sensing bioFETs. In some embodiments, the sequencing of nucleic acids may include any nucleic acid such as, but not limited to, double-stranded or single-stranded, linear or circular nucleic acids (e.g., circular DNA), single stranded DNA hairpins, DNA/RNA hybrids, RNA with a recognition site for binding of the polymerase, RNA hairpins, or mitochondrial DNA. Some embodiments provide for sequencing complex nucleic acid structures, such as 5' or 3' non-translation sequences, tandem repeats, exons or introns, chromosomal segments, whole chromosomes or genomes, using the dual gate back-side sensing bioFETs. In some embodiments, sequencing using the dual gate back-side sensing bioFETs may be performed to determine partial or complete nucleotide sequence of a nucleic acid, to detect the presence or absence of a single nucleotide polymorphism in a nucleic acid, to determine insertions, deletions, and genomic rearrangements, to determine the haplotype, karyotype, and/or genotype of a target analyte, to determine nucleic acid expression profiles of two or more target analytes, including, for example, wild-type and mutant phenotypes, diseased and normal tissue, untreated tissue and tissue treated with drug, enzymes, radiation, or chemical treatment.

The target analyte with a nucleic acid may be from any source including naturally occurring sources or synthetic sources. For example, the nucleic acids include, but are not limited to, PCR products, cosmids, plasmids, or naturally occurring or synthetic libraries. The nucleic acids, as discussed above in the context of arrays, may be of any length. By way of example, the nucleic acids may be hundreds, thousands, or tens of thousands nucleotides in length. In some embodiments, the nucleic acids are about 20-10000, 30-7500, 40-5000, 50-2500, 100-2000, 200-1000, 300-800, or 400-700 base pairs in size. In some embodiments, the nucleic acids are about 20, about 30, about 40, about 50, about 60, about 70, about 80, about 90, about 100, about 150, about 200, about 250, about 300, about 350, about 400, about 450, about 500, about 550, about 600, about 650, about 700, about 750, about 800, about 850, about 900, about 950, about 1000, about 1500, about 2000, about 2500, about 5000, about 7500, about 10000, or more than 10000 base pairs in length.

For sequencing nucleic acids using the dual gate back-side sensing bioFETs, the target analytes including nucleic acids may be prepared using techniques known in the art. Such techniques include, but are not limited to, DNA fragmentation by mechanical, enzymatic, or chemical means, including shearing, sonication, nebulization, endonuclease (e.g., DNase digestion, amplification such as PCR amplification, or any other technique known in the art to produce nucleic acid fragments, whether or not of a desired length (see, e.g., Sambrook, Joseph, Edward F. Fritsch, and Tom Maniatis, *Molecular Cloning: A Laboratory Manual.*

4th Ed. Cold Spring Harbor Laboratory Press (2012) Vol. 1, Ch. 6, 7, Vol. 2, Ch. 10, 11). Fragmentation can be followed by size selection techniques to enrich or isolate fragments of a particular length or size. Such techniques include, but are not limited to, gel electrophoresis or solid phase reversible immobilization (SPRI). Additional techniques for isolating and/or enriching sequences such as exons prior to sequencing are described in, for example, Albert, Thomas J., et al., "Direct selection of human genomic loci by microarray hybridization." *Nature Methods* 4.11 (2007): 903-905; Porreca, Gregory J., et al., "Multiplex amplification of large sets of human exons." *Nature Methods* 4.11 (2007): 931-936; Okou, David T., et al., "Microarray-based genomic selection for high-throughput resequencing." *Nature Methods* 4.11 (2007): 907-909; U.S. Pat. No. 9,588,051.

Where desired, for example, when the nucleic acids in the target analytes are at low concentrations, such as nucleic acids encompassing somatic mutations occurring at frequencies of less than 10%, less than 5%, less than 4%, less than 3%, less than 2%, or less than 1% of the nucleic acids in the sample, the nucleic acids may be amplified prior to or after placement in the dual gate back-side sensing bioFET. Any techniques may be used to amplify nucleic acids including, but not limited to, bridge amplification, rolling circle amplification, isothermal or non-isothermal amplification techniques. See, e.g., U.S. Pat. No. 5,641,658 (Cols. 5-7); U.S. Pub. Appl. Nos. 2002/0055100 A1 (Paragraphs [0222], [0232]); U.S. Pat. No. 7,115,400 (Col. 5, line 30); 2004/0096853 A1 (Paragraphs [0005]-[0025], [0033]-[0038]); 2004/0002090 A1; 2007/0128624 A1 (Paragraphs [0005]-[0013]); and (Paragraphs [0010]-[0018]); U.S. Pat. No. 8,349,167 (Col. 27, lines 14-21); U.S. Pat. No. 9,588,051 (Col. 24, lines 36-67); Paez, J. Guillermo, et al., "Genome coverage and sequence fidelity of φ29 polymerase-based multiple strand displacement whole genome amplification." *Nucleic Acids Research* 32.9 (2004): e71-e71.

In some embodiments, the target nucleic acids are ligated to adaptor sequences, on the 5', the 3', or on both the 5' and 3' ends. In some embodiments, the adaptor sequences is a barcode or similar sequences to identify the nucleic acids. The adaptor sequences may, for example, include sequences complementary to amplification primers and/or include a moiety that facilitates attachment or binding of the nucleic acid to the dual gate back-side sensing bioFET. Such a moiety, includes but is not limited to, a biotin molecule or a double biotin moiety (see Diehl. Frank, et al., "BEAMing: single-molecule PCR on microparticles in water-in-oil emulsions." *Nature Methods* 3.7 (2006): 551-559) or NHS-ester and amine affinity pair.

In various embodiments, the dual gate back-side sensing bioFETs described herein are used for single molecule sequencing and in other embodiments for sequencing different nucleic acids in parallel. In embodiments where the target analyte includes multiple nucleic acids, the dual gate back-side sensing bioFETs may be in array format and include identical or non-identical nucleic acids, which may or may not be heterogeneously dispersed on the array. By way of example, a nucleic acid sequencing array may include multiple identical nucleic acids, where, for example, more than one dual gate back-side sensing bioFET sensing layer, and optionally the entire sensing surface of the array, has identical nucleic acids dispersed thereon. The identical nucleic acids may be uniformly distributed on the array surface or they may be organized into discrete regions (or cells) on that surface. Alternatively, the nucleic acid sequencing arrays may include multiple non-identical nucleic acids. Such arrays may then include non-identical nucleic acids heterogeneously dispersed on the surface of the array, or the multiple non-identical nucleic acids may be organized into discrete regions (or cells) on the surface of the array where, for example, identical nucleic acids are distributed in one discrete region, another discrete region contains different non-identical nucleic acids, and so forth, such that the array includes multiple non-identical nucleic acids dispersed into discrete regions of identical nucleic acids.

Knowledge of the sequence of the newly synthesized nucleic acid is derived by determining whether a known nucleotide has been incorporated into the newly synthesized nucleic acid and, if so, how many of such known nucleotides have been incorporated. To detect nucleotide incorporation in applications of the nucleic acid sequencing described herein, any, methods or techniques may be used that permit detection using a dual gate back-side sensing bioFET. In some embodiments, detection of nucleotide incorporation includes changes in the dual gate back-side sensing bioFET current and/or threshold voltage. Such changes may be the result of one or more of the following events either singly or some combination thereof: generation of PPi, generation of Pi (e.g., in the presence of pyrophosphatase), generation of hydrogen (and concomitant changes in pH for example in the presence of low strength buffer), reduced concentration of unincorporated dNTP at the sensing layer of a dual gate back-side sensing bioFET, or delayed arrival of unincorporated dNTP at the sensing layer of a dual gate back-side sensing bioFET. In some embodiments, detection may occur by capture reagents that bind selectively to PPi. Such PPi receptors include; but are not limited to, those discussed in U.S. Pub. Appl. No. 2010/028617 A1 (Paragraph [0245]); Lee, Dong Hoon, Soon Young Kim, and Jong-In Hong, "A fluorescent pyrophosphate sensor with high selectivity over ATP in water."*Angewandte Chemie international Edition* 43.36 (2004): 4777-4780; U.S. Pub. Appl. No. 2005/0119497 A1 (Paragraph [0113]); Lee, Dong Hoon, et al., "An azophenol-based chromogenic pyrophosphate sensor in water." *Journal of the American Chemical Society* 125.26 (2003): 7752-7753; Lee, Han Na, et al., "Simple but effective way to sense pyrophosphate and inorganic phosphate by fluorescence changes." *Organic Letters* 9.2 (2007): 243-246; Karymov, M. A.; et al., "Fixation of DNA directly on optical waveguide surfaces for molecular probe biosensor development." *Sensors and Actuators B: Chemical* 29.1-3 (1995): 324-327; Fabbrizzi, Luigi, et al., "Pyrophosphate detection in water by fluorescence competition assays: inducing selectivity through the choice of the indicator." *Angewandte Chemie International Edition* 41.20 (2002): 3811-3814; International Appl. Pub. No. WO 2007/002204 (Page 9, lines 30-34; Page 10, Page 11, Page 12 lines 1-12); McDonough, Matthew J., et al., "Selective recognition of pyrophosphate in water using a backbone modified cyclic peptide receptor." *Chemical Communications* 28 (2006): 2971-2973. Many of the techniques and conditions described above in the context of nucleic acid arrays, for example, attachment of nucleic acids to the dual gate back-side sensing bioFET, are equally applicable to the sequencing applications described herein, and reference may be made thereto.

Further Applications

Several additional applications of the dual gate back-side sensing bioFETs described herein are contemplated. For example, the sensing layer of a dual gate back-side sensing bioFET provides real-time, label-free quantification and analysis for a variety of biological, chemical, and other applications including, but not limited to, gene expression analysis, comparative genome hybridization (CGH), array-based exon enrichment processes, protein sequencing, tissue microarrays, and cell culture. In some embodiments, the dual gate back-side sensing bioFET may be used to screen samples including, but not limited to, bodily fluids and/or tissues such as blood, urine, saliva, CSF, or lavages or environmental samples such as water supply samples or air samples, for the presence or absence of a substance. For example, the arrays may be used to determine the presence or absence of pathogens (e.g., food-borne or infectious pathogens) such as viruses, bacteria, or parasites based on target genomic, proteomic, and/or other elements. The arrays may also be used to identify the presence or absence or characterize cancer cells or cells that are indicative of another condition or disorder, in a subject. Additional applications for use of the dual gate back-side sensing bioFETs described herein include those described in U.S. Pat. No. 8,349,167 (Gene expression analysis, comparative genome hybridization (CGH), array-based exon enrichment processes); U.S. Pat. No. 8,682,592 (Non-Invasive Prenatal Diagnosis (NIP D), DNA/RNA contamination, SNP identification); U.S. Pat. No. 9,096,899 (Method of amplifying and sequencing DNA within a flow cell is provided); U.S. Pat. No. 9,340,830 (Analyzing a tumor sample); U.S. Pat. No. 9,329,173 (Automated system for testing for *Salmonella enterica* bacteria); U.S. Pat. No. 9,341,529 (Method for manufacturing a pressure sensor); U.S. Pub. Appl. Nos. 2015/0353920; 2015/0355129 (Chemical and biological substances detection in bodily fluid); 2016/0054312 (Chemically differentiated sensor array for sample analysis); 2016/0040245 (Identification and molecular characterization of the CTCs associated with neuroendocrine prostate cancer (NEPC).

In some embodiments, the dual gate back-side sensing bioFETs may be used to obtain single cell gene expression profiles from one or more cells in a cellular sample of interest, for example, in heterogeneous cellular samples. Such samples often exhibit a high degree of variation in their gene/biomarker expression levels (e.g., due to the cell cycle, environment, and stochastic mechanism of transcription/translation), even among individual cells that have the same phenotype. The dual gate back-side sensing bioFETs enable interrogation of the expression profile of each cell in the sample. In certain aspects, the subject methods for single-cell molecular profiling obviate the need for separating cells of interest from a heterogeneous cellular sample with individual profiling available at each dual gate back-side sensing bioFET. Direct molecular profiling in heterogeneous cell samples is advantageous for clinical diagnostic and biomarker discovery applications. In certain aspects, the dual gate back-side sensing bioFETs are used in molecular profiling and cellular subtyping of heterogeneous original or enriched disease tissue and biological fluid samples, for example, biopsy tumor samples, endothelial cells from cardiovascular disease samples, bone marrow samples, lymph node samples, lymph, amniotic fluid, brain samples from different neurological disorders, lung pathological samples, and/or any other heterogeneous disease tissue sample of interest, Thus, for example, the dual gate back-side sensing bioFETs are used in the molecular profiling of normal biological tissue and biological fluid samples, to elucidate, for example, the mechanisms of differentiation, immune responses, cell-cell communication, or brain development.

In some embodiments, the dual gate back-side sensing bioFETs are used in obtaining single cell expression profiles in circulating tumor cells (CTCs). CTCs may derive from metastases and can recirculate through the bloodstream and lymph to colonize distinct organs and/or the primary tumor, giving rise to secondary metastasis, CTCs play a critical role in the metastatic spread of carcinomas. Therefore, detection of CTCs in blood (liquid biopsy) or disseminating tumor cells (DTC) in bone marrow may be used to monitor tumor staging and would improve the identification, diagnosis, and treatment of cancer patients at high risk of metastatic relapse, See, e.g., U.S. Pat. No. 9,340,830 (Col, 205, lines 61-64); U.S. Pat. No. 9,447,411 (Col. 21, lines 42-54); U.S. Pat. No. 9,212,977 (Col. 19, lines 56-67); U.S. Pat. No. 9,347,946 (Col. 9, lines 16-30). In some embodiments, the dual gate back-side sensing bioFETs are used to obtain expression and mutation profiles in a cellular sample that includes CTCs as well as non-target contaminating cell types (e.g., leukocytes). See, e.g., U.S. Pat. No. 9,340,830 (Col. 1, lines 41-67); U.S. Pat. No. 9,447,411 (Col. 2, lines 41-55); U.S. Pat. No. 9,212,977 (Col. 2, lines 48-67; Col, 3 lines 1-10); and U.S. Pat. No. 9,347,946 (Col. 9).

In other embodiments, the dual gate back-side sensing bioFETs described herein may provide point-of-care, portable, and/or real-time diagnostic tools. They may, for example, provide an electronic readout of an enzyme linked immunosorbent assay (ELISA) or other assays to detect various chemical or biological substances. The dual gate back-side sensing bioFETs may be configured to transduce or convert a biochemical binding event or reaction into an electrical signal, which may be read out. Indirect detection of a freely diffusing, electronically active species produced at the site of a bound chemical or biological substance may be performed utilizing the dual gate back-side sensing bioFETs. Electronic readout ELISA schemes where an enzyme capable of producing an electronically active species may be used. In some embodiments, riboswitches are used to detect metabolites. See, e.g., Mironov, Alexander S., et al., "Sensing small molecules by nascent RNA: a mechanism to control transcription in bacteria." *Cell* 111.5 (2002): 747-756; Winkler, Wade, Ali Nahvi, and Ronald R. Breaker, "Thiamine derivatives bind messenger RNAs directly to regulate bacterial gene expression." *Nature* 419.6910 (2002): 952-956. In some embodiments, the dual gate back-side sensing bioFET arrays are used to measure the kinetics of a reaction and/or compare the activities of enzymes, including substrates, a co-factor; or another moiety for readout.

Other applications for the dual gate back-side sensing bioFET arrays involve the use of molecular recognition sites; where molecules that specifically recognize particular target molecules are either identified or designed and applied to the surface of the array. Previous work with chemFETs has demonstrated the ability of single individual ISFETs to recognize ions such as potassium.

In some embodiments, the dual gate back-side sensing bioFET is used to monitor the presence and/or amount of specific molecules including, for example, environmental testing of specific toxins and important elements. Such testing may use molecular recognition sites to measure both pollution gases and particulate contamination, where molecules that specifically recognize particular target molecules are either identified or designed and applied to the surface of the array. See, e.g., Brzozka et al. "Enhanced performance of potassium CHEMFETs by optimization of a polysiloxane membrane," *Sensors and Actuators B. Chemical* 18, 38-41 (1994); Sibbald et al. "A miniature flow-through cell with a four-function ChemFET integrated circuit for simultaneous measurements of potassium, hydrogen, calcium and sodium ions," *Analytica Chimica Acta.* 159, 47-62 (1984); Cobben et al. "Transduction of selective recognition of heavy metal ions by chemically modified field effect transistors (CHEM-FETs)," *Journal of the American Chemical Society* 114, 10573-10582 (1992). In some embodiments, the dual gate back-side sensing bioFET can be used with a personal, portable, and wearable detector system. This system can act as an early warning device indicating to the user that the pollution levels in their current local environment is at a level that could cause the user some discomfort or even lead to breathing problems. This is particularly relevant to people suffering from respiratory or bronchial or asthma conditions, where the user needs to take necessary precautions. The dual gate back-side sensing bioFET has the capability of detecting individual gases such as, for example, NOx, $SO_2$ and or CO and/or monitoring temperature and humidity. See U.S. Pub. Appl. Nos. 2014/0361901; 2016/0116434 (Paragraph [0117]). The pollution sensors may; for example, be referred to as a gas field effective transistor (gasFET). A gasFET may contain, for example, an FET with a gate metallization exposed to the surrounding atmosphere. When a gas is absorbed on the surface, protons can diffuse to the metal gas interface. This results in a dipole layer which affects the threshold voltage of the device.

In some embodiments, the dual gate back-side sensing bioFET may be used in vivo by introduction into a subject (e.g., in the brain or other region that is subject to ion flux) and then analyzing for changes. For example, electrical activity of cells may be detected by ionic flow. Thus, a bioFET array can be integrated onto a novel ion-discriminating tissue probe. Other applications include, for example, cochlear prosthesis and retinal and cortical implants. See, e.g., Humayun et al. *Vision Research* 43, 2573-2581 (2003); Normann et al. *Vision Research* 39, 2577-2587 (1999).

Final Remarks

Described herein are embodiments of a bioFET device that includes commonly fabricated bioFET sensors connected to a readout circuit designed to measure a differential signal between the bioFET sensors, According to some embodiments, a bioFET device includes a semiconductor substrate having a first surface and an opposite, parallel second surface and first and second bioFET sensors on the semiconductor substrate. The first bioFET sensor includes a first gate formed on the first surface of the semiconductor substrate and a first channel region formed within the semiconductor substrate beneath the first gate and interposing first S/D regions in the semiconductor substrate, wherein the first channel region includes a portion of the second surface of the semiconductor substrate. The second bioFET sensor includes a second gate formed on the first surface of the semiconductor substrate, wherein the first gate and the second gate are the same material, and a second channel region formed within the semiconductor substrate beneath the second gate and interposing second S/D regions in the semiconductor substrate, wherein the second channel region includes a portion of the second surface of the semiconductor substrate. The bioFET device also includes an isolation layer on the second surface of the semiconductor substrate. The isolation layer has a first opening that exposes a portion of the second surface of the semiconductor substrate that includes the first channel region, and a second opening that exposes a portion of the second surface of the semiconductor substrate that includes the second channel region. An interface layer is disposed on each of the first channel region and the second channel region in the first opening and the second opening, respectively. The bioFET device also includes a readout circuit having a differential amplifier designed to measure a difference between signals associated with the first bioFET sensor and the second bioFET sensor.

According to some embodiments, a microfluidic system includes a semiconductor substrate having a first surface and an opposite, parallel second surface, a first bioFET sensor having a first gate on the first surface of the semiconductor substrate, and a second bioFET sensor having a second gate on the first surface of the semiconductor substrate. An isolation layer is disposed on the second surface of the semiconductor substrate and has a first opening over the first bioFET sensor and a second opening over the second bioFET sensor. An interface layer is disposed in at least each of the first opening and the second opening. The system includes a readout circuit having a differential amplifier designed to measure a difference between signals associated with the first bioFET sensor and the second bioFET sensor. The system also includes a microfluidic network designed to deliver fluid to the interface layer disposed in each of the first opening and the second opening. The microfluidic network includes a first inlet channel, and a second inlet channel upstream of the first bioFET sensor and the second bioFET sensor, respectively. The microfluidic network also includes an outlet channel downstream of the first bioFET sensor and the second bioFET sensor.

According to some embodiments, a method of using a bioFET device includes providing a first bioFET sensor having a first gate on a first surface of a semiconductor substrate and a second bioFET sensor having a second gate on the first surface of the semiconductor substrate. The first gate is the same material as the second gate, and each of the first bioFET sensor and the second bioFET sensor includes an interface layer that binds with capture reagents. The method also includes flowing a solution containing the capture reagents through a first microfluidic channel positioned over the first bioFET sensor and through a second microfluidic channel positioned over the second bioFET sensor. The method includes flowing a solution containing target analytes that bind to the capture reagents down the first microfluidic channel, but not the second microfluidic channel. The method includes flowing a buffer solution through the first microfluidic channel and the second microfluidic channel, and detecting a differential signal obtained from the first bioFET sensor and the second bioFET sensor.

It is to be appreciated that the Detailed Description section, and not the Abstract of the Disclosure section, is intended to be used to interpret the claims. The Abstract of the Disclosure section may set forth one or more but not all exemplary embodiments of the present disclosure as contemplated by the inventor(s), and thus, is not intended to limit the present disclosure and the subjoined claims in any way.

It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments but should be defined in accordance with the subjoined claims and their equivalents.

What is claimed is:

1. A bioFET device, comprising:
  a semiconductor substrate having a first surface and an opposite, parallel second surface;
  a first bioFET sensor on the semiconductor substrate, the first bioFET sensor comprising:
    a first gate formed on the first surface of the semiconductor substrate, and a first channel region formed within the semiconductor substrate beneath the first gate and interposing first S/D regions in the semiconductor substrate, wherein the first channel region includes a portion of the second surface of the semiconductor substrate;
a second bioFET sensor on the semiconductor substrate, the second bioFET sensor comprising:
  a second gate formed on the first surface of the semiconductor substrate, wherein the first gate and the second gate are the same material, and
  a second channel region formed within the semiconductor substrate beneath the second gate and interposing second S/D regions in the semiconductor substrate, wherein the second channel region includes a portion of the second surface of the semiconductor substrate;
an isolation layer on the second surface of the semiconductor substrate and having a first opening that exposes a portion of the second surface of the semiconductor substrate that includes the first channel region, and a second opening that exposes a portion of the second surface of the semiconductor substrate that includes the second channel region;
a continuous interface layer disposed on the first channel region and the second channel region in the first opening and the second opening; and
a readout circuit comprising a differential amplifier configured to measure a difference between signals associated with the first bioFET sensor and the second bioFET sensor.

2. The bioFET device of claim 1, further comprising a first array of bioFET sensors that includes the first bioFET sensor, and a second array of bioFET sensors that includes the second bioFET sensor.

3. The bioFET device of claim 2, wherein each bioFET sensor of the first array of bioFET sensors is electrically coupled to a positive input of the differential amplifier, and each bioFET sensor of the second array of bioFET sensors is electrically coupled to a negative input of the differential amplifier.

4. The bioFET device of claim 2, wherein a bioFET sensor of the first array of bioFET sensors is electrically coupled to a positive input of the differential amplifier, and a corresponding bioFET sensor of the second array of bioFET sensors is electrically coupled to a negative input of the differential amplifier.

5. The bioFET device of claim 1, further comprising a first microfluidic channel positioned over the first bioFET sensor and configured to deliver fluid into the first opening in the isolation layer, and a second microfluidic channel positioned over the second bioFET sensor and configured to deliver fluid into the second opening in the isolation layer.

6. The bioFET device of claim 1, further comprising capture reagents bound to portions of the continuous interface layer at least in each of the first opening and the second opening.

7. The bioFET device of claim 6, wherein the capture reagents bound to a portion of the continuous interface layer in the first opening have the same concentration and type as the capture reagents bound to a portion of the continuous interface layer in the second opening.

8. A microfluidic system, comprising:
a semiconductor substrate having a first surface and an opposite, parallel second surface;
a first bioFET sensor having a first gate on the first surface of the semiconductor substrate and a second bioFET sensor having a second gate on the first surface of the semiconductor substrate;
an isolation layer disposed on the second surface of the semiconductor substrate and having a first opening over the first bioFET sensor and a second opening over the second bioFET sensor;
a continuous interface layer disposed in the first opening and the second opening;
a readout circuit comprising a differential amplifier configured to measure a difference between signals associated with the first bioFET sensor and the second bioFET sensor; and
a microfluidic network configured to deliver fluid to the continuous interface layer disposed in the first opening and the second opening, the microfluidic network comprising:
  a first inlet channel fluidically coupled to the first bioFET sensor and a second inlet channel fluidically coupled to at least the second bioFET sensor, and
  an outlet channel downstream of the first bioFET sensor and the second bioFET sensor.

9. The microfluidic system of claim 8, further comprising a first array of bioFET sensors that includes the first bioFET sensor, and a second array of bioFET sensors that includes the second bioFET sensor.

10. The microfluidic system of claim 8, wherein the second inlet channel branches into a first sensing channel and a second sensing channel, wherein the first sensing channel delivers fluid to a portion of the continuous interface layer disposed in the first opening and the second sensing channel delivers fluid to a portion of the continuous interface layer disposed in the second opening.

11. The microfluidic system of claim 10, wherein the first inlet channel is fluidically coupled with the first sensing channel.

12. The microfluidic system of claim 11, further comprising a valve located in the first sensing channel between a location where the first inlet channel is fluidically coupled with the first sensing channel and a location where the second inlet channel branches into the first sensing channel and the second sensing channel.

13. The microfluidic system of claim 12, further comprising a second valve located in the second sensing channel downstream of the second bioFET sensor.

14. The microfluidic system of claim 8, wherein the first inlet channel is configured to deliver fluid to a portion of the continuous interface layer in the first opening, but not to a portion of the continuous interface layer in the second opening.

15. The microfluidic system of claim 8, further comprising an array of electrodes patterned within each of the first inlet channel, the second inlet channel, and the outlet channel, wherein the array of patterned electrodes are configured to move a droplet of solution through the microfluidic network.

16. A method of using a bioFET device, comprising:
providing a first bioFET sensor having a first gate on a first surface of a semiconductor substrate and a second bioFET sensor having a second gate on the first surface of the semiconductor substrate, wherein the first gate is the same material as the second gate;
binding capture reagents to a continuous interface layer disposed on channel regions of the first and second bioFET sensors;

flowing a solution containing the capture reagents through a first microfluidic channel positioned over the first bioFET sensor and through a second microfluidic channel positioned over the second bioFET sensor;

flowing a solution containing target analytes configured to bind to the capture reagents down the first microfluidic channel, but not the second microfluidic channel;

flowing a buffer solution through the first microfluidic channel and the second microfluidic channel; and detecting a differential signal obtained from the first bioFET sensor and the second bioFET sensor.

17. The method of claim 16, further comprising flowing a wash solution through the first microfluidic channel and the second microfluidic channel after flowing the solution containing the target analytes.

18. The method of claim 16, further comprising actuating a valve to cut off access to the second microfluidic channel during the flowing of the solution containing the target analytes down the first microfluidic channel.

19. The method of claim 16, wherein flowing the solution containing capture reagents comprises flowing a solution containing one or more of an enzyme, antibody, ligand, peptide, nucleotide, cell of an organ, organism, DNA, RNA, or piece of tissue.

20. The method of claim 16, wherein flowing the solution containing target analytes comprises flowing a solution containing one or more of DNA, RNA, antibody, polypeptide, cell, tissue, protein, or tumor marker.

* * * * *